US009051566B2

(12) United States Patent
Giordano et al.

(10) Patent No.: US 9,051,566 B2
(45) Date of Patent: Jun. 9, 2015

(54) POST-TRANSCRIPTIONAL GENE SILENCING USING EXPRESSED DOUBLE STRANDED RNA

(75) Inventors: Tony Giordano, Phoenixville, PA (US); Catherine Pachuk, Lansdale, PA (US); Chandrasekhar Satishchandran, Lansdale, PA (US)

(73) Assignee: ALNYLAM PHARMACEUTICALS, INC., Cambridge, MA (US)

( * ) Notice: Subject to any disclaimer, the term of this patent is extended or adjusted under 35 U.S.C. 154(b) by 1365 days.

(21) Appl. No.: 10/762,395

(22) Filed: Jan. 22, 2004

(65) Prior Publication Data

US 2004/0152117 A1 Aug. 5, 2004

Related U.S. Application Data

(62) Division of application No. 10/062,707, filed on Jan. 31, 2002, now abandoned.

(60) Provisional application No. 60/265,805, filed on Jan. 31, 2001, provisional application No. 60/339,260, filed on Oct. 26, 2001.

(51) Int. Cl.
*C12N 15/10* (2006.01)
*C12Q 1/68* (2006.01)

(52) U.S. Cl.
CPC ........ *C12N 15/1086* (2013.01); *C12N 15/1096* (2013.01); *C12Q 1/6897* (2013.01)

(58) Field of Classification Search
None
See application file for complete search history.

(56) References Cited

U.S. PATENT DOCUMENTS

| | | | |
|---|---|---|---|
| 3,931,397 A | 1/1976 | Harnden |
| 4,130,641 A | 12/1978 | Ts'o et al. |
| 4,283,393 A | 8/1981 | Field et al. |
| 4,469,863 A | 9/1984 | Ts'o et al. |
| 4,605,394 A | 8/1986 | Skurkovich |
| 4,766,072 A | 8/1988 | Jendrisak et al. |
| 4,897,355 A | 1/1990 | Eppstein et al. |
| 5,024,938 A | 6/1991 | Nozaki et al. |
| 5,034,323 A | 7/1991 | Jorgensen et al. |
| 5,107,065 A | 4/1992 | Shewmaker et al. |
| 5,173,410 A | 12/1992 | Ahlquist |
| 5,190,931 A | 3/1993 | Inouye |
| 5,208,149 A | 5/1993 | Inouye |
| 5,231,020 A | 7/1993 | Jorgensen et al. |
| 5,264,618 A | 11/1993 | Felgner et al. |
| 5,272,065 A | 12/1993 | Inouye et al. |
| 5,279,833 A | 1/1994 | Rose |
| 5,283,184 A | 2/1994 | Jorgensen et al. |
| 5,283,185 A | 2/1994 | Epand et al. |
| 5,365,015 A | 11/1994 | Grierson et al. |
| 5,453,566 A | 9/1995 | Shewmaker et al. |
| 5,459,127 A | 10/1995 | Felgner et al. |
| 5,514,546 A | 5/1996 | Kool |
| 5,578,716 A | 11/1996 | Szyf et al. |
| 5,583,021 A | 12/1996 | Dougherty et al. |
| 5,624,803 A | 4/1997 | Noonberg et al. |
| 5,631,148 A | 5/1997 | Urdea |
| 5,643,762 A | 7/1997 | Ohshima et al. |
| 5,683,985 A | 11/1997 | Chu et al. |
| 5,686,649 A | 11/1997 | Chua et al. |
| 5,691,140 A | 11/1997 | Noren et al. |
| 5,693,773 A | 12/1997 | Kandimalla et al. |
| 5,714,323 A | 2/1998 | Ohshima et al. |
| 5,739,309 A | 4/1998 | Dattagupta et al. |
| 5,747,338 A | 5/1998 | Giese et al. |
| 5,795,715 A | 8/1998 | Livache et al. |
| 5,798,265 A | 8/1998 | Springer et al. |
| 5,808,036 A | 9/1998 | Kool |
| 5,814,500 A | 9/1998 | Dietz |
| 5,850,026 A | 12/1998 | DeBonte et al. |
| 5,874,555 A | 2/1999 | Dervan et al. |
| 5,880,276 A | 3/1999 | Hammarskjold et al. |
| 5,908,779 A | 6/1999 | Carmichael et al. |
| 5,932,241 A | 8/1999 | Gorman |
| 5,972,704 A | 10/1999 | Draper et al. |
| 5,998,383 A | 12/1999 | Wright et al. |
| 6,010,908 A | 1/2000 | Gruenert et al. |
| 6,022,863 A | 2/2000 | Peyman |
| 6,054,299 A | 4/2000 | Conrad |
| 6,133,024 A | 10/2000 | Helene et al. |
| 6,291,504 B1 | 9/2001 | Nugiel et al. |
| 6,369,038 B1 | 4/2002 | Blumenfeld et al. |

(Continued)

FOREIGN PATENT DOCUMENTS

| | | |
|---|---|---|
| AU | 729454 | 2/2001 |
| AU | 743316 | 1/2002 |

(Continued)

OTHER PUBLICATIONS

Kenworthy et al., Nucleic Acids Research, 37(19):6587-6599 (2009).*
Bauer et al., Gene Ther., 16(1):142-147 (2009).*
Colby and Chamberlin, The specificity of interferon induction in chick embryo cells by helical RNA; Biochemistry, vol. 63, pp. 160-167, 1969.*
Der and Lau, Involvement of the double-stranded-RNA-dependent kinase PKR in interferon expression and interferon-mediated antiviral activity; PNAS, vol. 92, pp. 8841-8845, 1995.*
Torrence et al., Activation of human and mouse 2-5A synthetases and mouse protein P1Kinase by nucleic acids; FEBS Letters, vol. 130, No. 2, pp. 291-296, 1981.*
Robertson and Mathews, The regulation of the protein kinase PKR by RNA; Biochimie, vol. 78, pp. 909-914, 1996.*

(Continued)

*Primary Examiner* — Jennifer Dunston
*Assistant Examiner* — Addison D Ault
(74) *Attorney, Agent, or Firm* — Nixon Peabody LLP; Mark J. FitzGerald

(57) ABSTRACT

Described herein are methods for identifying nucleic acid sequences that modulate the function of a cell, the expression of a gene in a cell, or the biological activity of a target polypeptide in a cell. The methods involve the use of double stranded RNA expression libraries, double stranded RNA molecules, and post-transcriptional gene silencing techniques.

8 Claims, 3 Drawing Sheets

(56) References Cited

U.S. PATENT DOCUMENTS

| | | |
|---|---|---|
| 6,372,965 B1 | 4/2002 | Lightner et al. |
| 6,423,885 B1 | 7/2002 | Waterhouse et al. |
| 6,506,559 B1 | 1/2003 | Fire et al. |
| 6,531,647 B1 | 3/2003 | Baulcombe et al. |
| 6,573,099 B2 | 6/2003 | Graham |
| 6,635,805 B1 | 10/2003 | Baulcombe et al. |
| 2002/0086356 A1 | 7/2002 | Tuschl et al. |
| 2002/0114784 A1 | 8/2002 | Li et al. |
| 2002/0168707 A1 | 11/2002 | Graham |
| 2003/0018993 A1 | 1/2003 | Gutterson et al. |
| 2003/0027783 A1 | 2/2003 | Zernicka-Goetz |
| 2003/0036197 A1 | 2/2003 | Glassman et al. |
| 2003/0056235 A1 | 3/2003 | Fire et al. |
| 2003/0061626 A1 | 3/2003 | Plaetinck et al. |
| 2003/0074684 A1 | 4/2003 | Graham et al. |
| 2003/0159161 A1 | 8/2003 | Graham et al. |
| 2003/0165894 A1 | 9/2003 | Waterhouse et al. |
| 2004/0022748 A1 | 2/2004 | Ananthapadmanabhan et al. |
| 2004/0064842 A1 | 4/2004 | Graham et al. |
| 2004/0138168 A1 | 7/2004 | Satishchandran et al. |
| 2004/0180439 A1 | 9/2004 | Graham et al. |
| 2004/0237145 A1 | 11/2004 | Graham et al. |
| 2004/0266005 A1 | 12/2004 | Graham et al. |
| 2005/0250208 A1 | 11/2005 | Graham et al. |
| 2006/0014715 A1 | 1/2006 | Graham et al. |

FOREIGN PATENT DOCUMENTS

| | | |
|---|---|---|
| AU | 200195225 A1 | 1/2002 |
| CA | 2012312 C | 9/1990 |
| CA | 2 361 201 A1 | 8/2000 |
| CA | 2370628 A1 | 10/2000 |
| EP | 0 213 921 A2 | 3/1987 |
| EP | 0 281 380 A2 | 9/1988 |
| EP | 0 286 224 A2 | 10/1988 |
| EP | 0 300 680 A2 | 1/1989 |
| EP | 0 303 516 A2 | 2/1989 |
| EP | 0 306 347 A2 | 3/1989 |
| EP | 0 308 066 A2 | 3/1989 |
| EP | 0 318 281 A2 | 5/1989 |
| EP | 0 325 018 A2 | 7/1989 |
| EP | 0 347 501 A1 | 12/1989 |
| EP | 0 350 151 A2 | 1/1990 |
| EP | 0 213 921 B1 | 8/1990 |
| EP | 0 306 347 A3 | 10/1990 |
| EP | 0 318 281 A3 | 10/1990 |
| EP | 0 350 151 A3 | 10/1990 |
| EP | 0 308 066 A3 | 1/1991 |
| EP | 0 300 680 A3 | 6/1991 |
| EP | 0 242 016 B1 | 1/1992 |
| EP | 0 286 224 B1 | 11/1992 |
| EP | 0 350 151 B1 | 3/1994 |
| EP | 0 303 516 B1 | 7/1994 |
| EP | 0 306 347 B1 | 5/1995 |
| EP | 0 465 572 B1 | 6/1995 |
| EP | 0 281 380 B1 | 11/1995 |
| EP | 0 308 066 B1 | 12/1995 |
| EP | 0 300 680 B1 | 9/1996 |
| EP | 0 242 016 A1 | 10/1997 |
| EP | 0 921 195 A1 | 6/1999 |
| EP | 0 983 370 A1 | 3/2000 |
| EP | 1 229 134 A2 | 8/2002 |
| EP | 0 983 370 B1 | 9/2003 |
| EP | 1 229 134 A3 | 1/2004 |
| GB | 2353282 A | 2/2001 |
| GB | 2377221 A | 1/2003 |
| WO | WO 90/11682 A1 | 10/1990 |
| WO | WO 90/12094 A1 | 10/1990 |
| WO | WO 90/12488 A2 | 11/1990 |
| WO | WO 90/14090 A1 | 11/1990 |
| WO | WO 92/18522 A1 | 10/1992 |
| WO | WO 93/17098 A1 | 9/1993 |
| WO | WO 93/23551 A1 | 11/1993 |
| WO | WO 94/01550 A1 | 1/1994 |
| WO | WO 94/17194 A1 | 8/1994 |
| WO | WO 95/03406 A2 | 2/1995 |
| WO | WO 95/10607 A1 | 4/1995 |
| WO | WO 95/15378 A1 | 6/1995 |
| WO | WO 95/18854 A1 | 7/1995 |
| WO | WO 95/23225 A2 | 8/1995 |
| WO | WO 95/03406 A3 | 9/1995 |
| WO | WO 95/27783 A1 | 10/1995 |
| WO | WO 95/34668 A2 | 12/1995 |
| WO | WO 95/34668 A3 | 2/1996 |
| WO | WO 96/08558 A1 | 3/1996 |
| WO | WO 95/34668 A3 | 4/1996 |
| WO | WO 96/35706 A1 | 11/1996 |
| WO | WO 97/01952 A1 | 1/1997 |
| WO | WO 97/07668 A1 | 3/1997 |
| WO | WO 97/10360 A1 | 3/1997 |
| WO | WO 97/11170 A1 | 3/1997 |
| WO | WO 97/34638 A1 | 9/1997 |
| WO | WO 97/44450 A1 | 11/1997 |
| WO | WO 98/05770 A3 | 3/1998 |
| WO | WO 98/18811 A1 | 5/1998 |
| WO | WO 98/36083 A1 | 8/1998 |
| WO | WO 98/37213 A1 | 8/1998 |
| WO | WO 98/44138 A1 | 10/1998 |
| WO | WO 98/53083 A1 | 11/1998 |
| WO | WO 99/09045 A1 | 2/1999 |
| WO | WO 99/15682 A2 | 4/1999 |
| WO | WO 99/25853 A1 | 5/1999 |
| WO | WO 99/32619 A1 | 7/1999 |
| WO | WO 99/49029 A1 | 9/1999 |
| WO | WO 99/53050 A1 | 10/1999 |
| WO | WO 99/61631 A1 | 12/1999 |
| WO | WO 00/01846 A2 | 1/2000 |
| WO | WO 00/44914 | 8/2000 |
| WO | WO 00/63364 | 10/2000 |
| WO | WO 01/04313 A1 | 1/2001 |
| WO | WO 01/29058 A1 | 4/2001 |
| WO | WO 01/36646 A1 | 5/2001 |
| WO | WO 01/48183 A2 | 7/2001 |
| WO | WO 01/68836 A2 | 9/2001 |
| WO | WO 01/70949 A1 | 9/2001 |
| WO | WO 01/75164 A | 10/2001 |
| WO | WO 01/75164 A2 | 10/2001 |
| WO | WO 01/88114 A2 | 11/2001 |
| WO | WO 01/48183 A3 | 12/2001 |
| WO | WO 01/88114 A3 | 6/2002 |
| WO | WO 02/44321 A2 | 6/2002 |
| WO | WO 03/006477 A1 | 1/2003 |
| WO | WO 03/022052 A1 | 3/2003 |
| WO | WO 03/027298 A1 | 4/2003 |
| WO | WO 03/056012 A1 | 7/2003 |
| WO | WO 02/044321 A3 | 10/2003 |

OTHER PUBLICATIONS

Saunders and Barber, The dsRNA binding protein family: critical roles, diverse cellular functions; The FASEB Journel, vol. 17, pp. 961-993, 2003.*

Tian et al., The double-stranded RNA-binding motif: interference and much more; Nature Reviews, vol. 5, pp. 1013-1023, 2004.*

Bahramian et al., Transcriptional and Posttranscriptional Silencing of Rodent a1(I) Collagen by a Homologous Transcriptionally Self-Silenced Transgene; Molecular and Cellular Biology; vol. 19, No. 1, pp. 274-283, 1999.*

Billy et al., Specific interference with gene expression induced by long, double-stranded RNA in mouse embryonal teratocarcinoma cell lines; PNAS, vol. 98, No. 25, pp. 14428-14433, 2001.*

Yang et al., Specific Double-Stranded RNA Interference in Undifferentiated Mouse Embryonic Stem Cells; Mol Cell Biol, vol. 21, No. 22, pp. 7807-7816, 2001.*

Akashi et al., Escape from the interferon response associated with RNA interference using vectors that encode long modified hairpin-RNA; Molecular Biosystems, vol. 1, pp. 382-390, 2005.*

Chalupnikova et al., Production and application of long dsRNA in mammalian cells; siRNA Design: Methods and Protocols, Methods in Molecular biology, vol. 942, pp. 291-314, 2013.*

Geiss et al., Large-Scale Monitoring of Host Cell Gene Expression during HIV-1 Infection Using cDNA Microarrays; Virology, vol. 266, No. 8, pp. 8-16, 2000.*

(56) References Cited

OTHER PUBLICATIONS

U.S. Appl. No. 09/646,807, Graham et al., Not Published.
U.S. Appl. No. 60/117,635, Li et al., Not Published.
U.S. Appl. No. 60/130,377, Pachuk et al., Not Published.
Gohla et al., A Rapid and Sensitive Fluorometric Screening Assay Using YO-PRO-1 to Quantify Tumour Cell Invasion . . . , Clin. Exp. Metastasis, 1996, vol. 14, No. 5, pp. 451-458.
Kohn et al., Molecular Insights Into Cancer Invasion: Strategies for Prevention and Intervention, Perspectives in Cancer Research, 1995, pp. 1856-1862.
Sasaki et al., Identification of Anti-Invasive but Noncytotoxic Chemotherapeutic Agents Using the . . . , Cancer Research Techniques, 1998, vol. 24, No. 6, pp. 1038-1044.
Gatz, Christiane, Novel Inducible/Repressible Gene Expression Systems, Methods in Cell Biology, Chapter 30, 1995, vol. 50, pp. 411-424.
Liu et al., Lac/Tet Dual-Inducible System Functions in Mammalian Cell Lines, Short Technical Reports, BioTechniques, Apr. 1998, vol. 24, No. 4, pp. 624-632.
Habu et al., Development of an HIV-1-Dependent Expression Vector With the Cre/loxP System, Nucleic Acids Symposium Series, 1999, No. 42, pp. 295-296.
Fulks et al., Sequence Analysis of the Inversion Region Containing the Pilin Genes of Moraxella Bovis, Journal of Bacteriology. Jan. 1990, vol. 172, No. 1, pp. 310-316.
Lanzov et al., Recombinational Mechanism of Precise Excision of IS50 Mobile Element in . . . , Konstantinov Nuclear Physics Institute, 1994, vol. 28, No. 3, pp. 563-573.
"somatic cell," on-line medical dictionary, http://cancerweb.ncl.ac.uk/cgi-bin/ (Jan. 2006).
Agrawal et al., "Antisense therapeutics: is it as simple as complementary base recognition?" *Molecular Medicine Today* 6:72-81 (2000).
Agrawal et al., "RNA Interference: Biology, Mechanism, and Applications" *Microb. Mot. Biol. Rev.* 67:657-685 (2003).
Agrawal et al., "Self-Stabilized Oligonucleotides as Novel Antisense Agents," in *Delivery Strategies: antisense oligonucleotide therapeutics,* Akhtar et al., Eds., pp. 105-121 CRC Press, Inc., Boca Raton, Florida (1995).
Agrawal, "Antisense oligonucleotides: towards clinical trials," *TIBTECH* 14: 376-387 (1996).
Akgun et al., "Palindrome Resolution and Recombination in the Mammalian Germ Line", *Mol. Cell. Biol.* 17: 5559-5570 (Sep. 1997).
Akhtar et al., "Anti-HIV therapy with antisense oligonucleotides and ribozymes: realistic approaches or expensive myths?" *J. Antimicrob. Chemother.* 38: 159-165 (1996).
Ambion, "pT7/T3 18" and "pT7/T3 19" 4 pages (date unknown).
Anderson, "Human gene therapy," *Nature* 392:25-30 (1998).
Angell et al., "Consistent gene silencing in transgenic plants expressing a replicating potato virus X RNA," *EMBO J.* 16(12):3675-3684 (1997).
Annex B filed in EP 99 910 039.9 (Sep. 9, 2005).
Annex C filed in EP 99 910 039.9 (Sep. 9, 2005).
Annex D filed in EP 99 910 039.9 (Sep. 9, 2005).
Appeal against decision to refuse a European patent application issued Jul. 11, 2005, filed in EP 99 910 039.9 (Sep. 9, 2005).
Assaad et al., "Epigenetic repeat-induced gene silencing (RIGS) in *Arabidopsis,*" *Plant Molecular Biology* 22(6): 1067-1085 (1993).
Author unknown, "Breakthrough of the Year #4: Still hot," *Science* 302:2038-2045 (2003).
Bahner et al., "Transduction of Human CD34 $^+$ Hematopoietic Progenitor Cells by a Retroviral Vector Expressing an RRE Decoy Inhibits Human Immunodeficiency Virus Type I Replication in Myelomonocytic Cells Produced in Long-Term Culture," *J. Virol.* 70:4352-4360 (1996).
Bahramian et al. "Transcriptional and Posttranscriptional Silencing of Rodent α1(I) Collagen by a Homologous Transcriptionally Self-Silenced Transgene" *Mol. Cell. Biol.* 19(1):274-283 (1999).
Balandin et al., "Silencing of a β-1-3-glucanase transgene is overcome during seed formation," *Plant Molecular Biology* 34(1):125-137 (1997).

Barbeau et al., "Characterization of the human and mouse Fli-1 promoter regions," *Biochim. Biophys. Acta* 1307: 220-232 (1996).
Barlow et al., "Interferon synthesis in the early post-implantation mouse embryo," *Differentiation* 27:229-235 (1984).
Bass, "RNA Interference: The short answer," *Nature* 411:428-429 (2001).
Baulcombe, "RNA as a target and an initiator of post-transcriptional gene silencing in transgenic plants," *Plant Molecular Biology* 32(1-2):79-88 (1996).
Baum et al.,"Inhibition of Protein Synthesis in Reticulocyte Lysates by a Double-Stranded RNA Component in Hela mRNA," *Biochem. Biophys. Res. Commun* 114:41-49 (1983).
Beretta et al., "Expression of the protein kinase PKR is modulated by IRF-1 and is reduced in 5q-associated leukemias," *Oncogene* 12:1593-1596 (1996).
Betz, "RNAi: RNA Interference," Promega Notes Magazine, No. 83, pp. 33-36 (2003).
Bevec et al., "Constitutive Expression of Chimeric *Neo*-Rev Response Element Transcripts Suppresses HIV-1 Replication in Human CD4$^+$ T Lymphocytes," *Hum. Gene Ther.* 5:193-201 (1994).
Bevilacqua, et al., "Antisense RNA inhibits endogenous gene expression in mouse preimplantation embryos: Lack of double-stranded RNA "melting" activity," *Proc. Natl. Acad. Sci. USA* 85:831-835 (1988).
Bhan et al., "2',5'-Linked Oligo-3'-deoxyribonucleoside phosphorothiate chimeras: thermal stability and antisense inhibition of gene expression" *Nucl. Acids Res.* 1(16):3310-3317 (1997).
Bigler et al., "Novel location and function of a thyroid hormone response element," *EMBO J.* 14:5710-5723 (1995).
Billy et al. "Specific interference with gene expression induced by long, double stranded RNA in mouse embryonal teratocarcinoma cell lines," *Proc. Natl. Acad. Sci. USA* 98(25):14428-14433 (2001).
Bingham, "Cosuppression Comes to the Animals," *Cell* 90(3):385-387 (1997).
Birchler et al., "Making noise about silence: repression of repeated genes in animals" *Curr. Opin. Genet. Develop.* 10:211-216 (2000).
Bisat et al.., "Differential and cell type specific expression of murine alpha-interferon genes is regulated on the transcriptional level," *Nucl. Acids Res.* 13:6067-6083 (1988).
Boldin et al., "Involvement of MACH, a Novel MORT1/FADD-Interacting Protease, in Fas/APO-1- and TNF Receptor-Induced Cell Death" *Cell* 85:803-815 (1996).
Borecky et al., "Therapeutic Use of Double-Stranded RNAs in Man" *Tex. Rep. Biol. Med.* 14:575-581 (1981-1982).
Bosher and Labouesse, "RNA Interference: Genetic Wand and Genetic Watchdog," Nature Cell Biology 2:E31-E36 (2000).
Bradbrook, "European Search Report," From European patent appl. No. 02250681.0, 5 pages, European Patent Office, Munich Germany (mailed Dec. 15, 2003).
Braich et al., "Regiospecific Solid-Phase Synthesis of Branched Oligonucleotides. Effect of Vicinal 2',5'-(or 2',3'-) and 3',5' Phosphodiester Linkages on the Formation of Hairpin DNA" *Bioconjugate Chem.* 8:370-377 (1997).
Branch, "A good antisense molecule is hard to find," *Trends Biochem. Sci.* 23:45-50 (1998).
Brand et al., "The Tat Protein of Human Immunodeficieny Virus Type 1 Is a Substrate and Inhibitor of the Interferon-induced, Virally Activated Protein Kinase, PKR," *J. Biol. Chem.* 272:8388-8395 (1997).
Brigneti et al., "Viral pathogenicity determinants are suppressors of transgene silencing in *Nicotiana benthamiana,*" *EMBO J.* 17(22):6739-6746 (1998).
Brown et al., "Identification through Overexpression and Tagging of the Variant Type of the Mouse H1e and H1c Genes," *J. Biol. Chem.* 268:713-718 (1993).
Brummelkamp et al., "Stable suppression of tumorigenicity by virus-mediated RNA," *Cancer Cell* 2:243-247 (2002).
Brummelkamp et al., "A System for Stable Expression of Short Interfering RNAs in Mammalian Cells," *Science* 296:550-553 (2002).
Brummell et al., "Inverted repeat of a heterologous 3'-untranslated region for high-efficiency, high-throughput gene silencing" *Plant J.* 33:793-800 (2003).

(56) References Cited

OTHER PUBLICATIONS

Buchan et al., "Characterization of three non-peptide endothelin receptor ligands using human cloned $ET_a$ and $ET_b$ receptors," *Br. J. Pharmacol.* 112: 1251-1257 (1994).
Burke et al., "Appearance of Interferon Induciblility and Sensitivity During Differentiation of Murine Tetrocarcinoma Cells in Vitro," *Cell* 13(2):243-248 (1978).
Cameron et al., "Multiple Domains in a Ribozyme Construct Confer Increased Suppressive Activity in Monkey Cells" *Antisense Res. Develop.* 4:87-94 (1994).
Cameron et al., "Inhibition of gene expression by a short sense fragment," *Nucl. Acids Res.* 19(3):469-475 (1991).
Caplen et al., "dsRNA-mediated gene silencing in cultured *Drosophila* cells: a tissue culture model for the analysis of RNA interference," *Gene*252:95-105 (2000).
Caplen et al., "Specific inhibition of gene expression by small double-stranded RNAs in invertebrate and vertebrate systems," *Proc. Natl. Acad. Sci. USA* 98:9742-9747 (2001).
Carthew, "Gene silencing by double-stranded RNA" *Curr. Opin. Cell. Biol.* 13:244-248 (2001).
Chernajovsky et al., "Human Kinesin Light (β) Chain Gene: DNA Sequence and Functional Characterization of Its Promoter and First Exon," *DNA Cell Biol.* 15: 965-974 (1996).
Christy et al., "Functional Analysis of the Long Terminal Repeats of Intracisternal A-Particle Genes: Sequences within the U3 Region Determine Both the Efficiency and Direction of Promoter Activity," *Mol. Cell. Biol.* 8:1093-1102 (1988).
Chuah et al., "Inhibition of Human Immunodeficiency Virus Type-1 by Retroviral Vectors Expressing Antisense-TAR," *Human Gene Therapy* 5:1467-1475 (1994).
Clusel et al., "Ex vivo regulation of specific gene expression by nanomolar concentration of double-stranded dumbbell oligonucleotides," *Nucl. Acids Res.* 21:3405-3411 (1993).
Clusel et al., "Inhibition of HSV-1 Proliferation by Decoy Phosphodiester Oligonucleotides Containing ICP4 Recognition Sequences," *Gene Expression* 4:301-309 (1995).
Cogoni et al., "Suppression of gene expression by homologous transgenes," *Antonie Van Leeuwenhoek* 65(3):205-209 (1994).
Cogoni et al., "Transgene silencing of the *al-1* gene in vegetative cells of *Neurospora* is mediated by a cytoplasmic effector and does not depend on DNA-DNA interactions or DNA methylation," *EMBO J.* 15(12):3153-3163 (1996).
Cogoni et al., "Isolation of quelling-defective (*qde*) mutants impaired in posttranscriptional transgene-induced gene silencing in *Neurospora crassa*," *Proc. Natl. Acad. Sci. USA* 94(19):10233-10238 (1997).
Cogoni et al., "Post-transcriptional gene silencing across kingdoms" *Curr. Opin. Genet. Devel.* 10:638-643 (2000).
Cogoni et al., "Gene silencing in *Neurospora crassa* requires a protein homologous to RNA-dependent RNA polymerase," *Nature* 399:166-169 (1999).
Cogoni et al., "Posttranscriptional Gene Silencing in *Neurospora* by a RecQ DNA Helicase," *Science* 286:2342-2344 (1999).
Cohli et al., "Inhibition of HIV-1 Multiplication in a Human CD4+ Lymphocytic Cell Line Expressing Antisense and Sense RNA Molecules Containing HIV-1 Packaging Signal and Rev Response Element(s)," *Antisense Research and Development* 4:19-26 (1994).
Coleman et al., "The Use of RNAs Complementary to Specific mRNAs to Regulate the Expression of Individual Bacterial Genes" *Cell* 37:429-436 (1984).
European Register for DE 199 03 713.2.
European Register for WO 00/63364.
European Register for WO 00/44914.
Courtney-Gutterson et al., "Modification of Flower Color in Florist's Chrysanthemum: Production of White-Flowering Variety Through Molecular Genetics," *Biotechnology* 12(3):268-271 (1994).
Couzin, "Small RNAs Make Big Splash" *Science* 298:2296-2297 (2002).

Czauderna et al., "Structural variations and stabilising modifications of synthetic siRNAs in mammalian cells" *Nucl. Acids Res.* 31(11):1-12 (2003).
Dalmay et al., "An RNA-Dependent RNA Polymerase Gene in *Arabidopsis* Is Required for Posttranscriptional Gene Silencing Mediated by a Transgene but Not by a Virus," *Cell* 101:543-553 (2000).
de Carvalho et al., "Suppression of β-1,3-glucanase transgene expression in homozygous Plants," *EMBO J.* 11(7):2595-2602 (1992).
de Carvalho Niebel et al., "Post-Transscriptional Cosuppression of β-1,3-Glucanase Genes Does Not Affect Acculmulation of Transgene Nuclear mRNA," *Plant Cell* 7(3):347-358 (1995).
De Lange et al., "Suppression of Flavonoid Flower Pigmentation Genes in *Petunia hybrida* by the Introduction of Antisense and Sense Genes," *Current Topics in Microbiology and Immunology* 197:57-75 (1995).
Decision to refuse a European patent application dated Jul. 11, 2005, filed in EP 99 910 039.9, 13 pages.
DeCoy et al., "Anti sense DNA Down-regulates Protein Kinase C-ϵ and Enhances Vasopressin-stimulated Na+ Absorption in Rabbit Cortical Collecting Duct," *J. Clin. Invest.* 95:2749-2756 (1995).
Depicker et al., "Post-transcriptional gene silencing in plants," *Current Opinion in Cell Biology* 9(3):373-382 (1997).
Di Serio et al., "Sense- and antisense-mediated gene silencing in tobacco is inhibited by the same viral suppressors and is associated with accumulation of small RNAs," *Proc. Natl. Acad. Sci. USA* 98:6506-6510 (2001).
Ding, "RNA silencing," *Current Opinion in Biotechnology* 11:152-156 (2000).
Dobrikova et al., "T7 DNA-dependent RNA polymerase can transcribe RNA from tick-borne encephalitis virus (TBEV) cDNA with SP6 promoter," *FEBS Lett.* 382:327-329 (1996).
Doench et al., "siRNAs can function as miRNAs" *Genes Dev.* 17:438-442 (2003).
Dolnick, "Naturally Occurring Antisense RNA," *Pharm. Ther.* 75:179-184 (1997).
Domeier et al., "A Link Between RNA Interference and Nonsense-Mediated Decay in *Caenorhabditis elegans*," *Science* 289:1928-1930 (2000).
Dorer et al., "Expansions of Transgene Repeats Cause Heterochromatin Formation and Gene Silencing in *Drosophilia*," *Cell* 77:993-1002 (1994).
Dorer et al., "Transgene Repeat Arrays Interact with Distant Heterochromatin and Cause Silencing in *cis* and *trans*," *Genetics* 147(3):1181-1190 (1997).
Dougherty et al., "Transgenes and gene suppression: telling us something new?" *Curr. Opin. Cell Biol.* 7: 399-405 (1995).
Dougherty et al., "RNA-Mediated Virus Resistance in Transgenic Plants: Exploitation of a Cellular Pathway Possibly Involved in RNA Degradation," *Mol. Plant-Microbe Interactions* 7(5):544-552 (1994).
Dronkert et al., "Mouse RAD54 Affects DNA Double-Strand Break Repair and Sister Chromatid Exchange," *Mol. Cell. Biol.* 20:3147-3156 (2000).
Dykxhoorn et al., "Killing the Messenger: Short RNAs that Silence Gene Expression" *Nature Reviews Molecular Cell Biology* 4:457-467 (2003).
Elbashir et al., "Duplexes of 21-nucleotide RNAs mediate RNA interference in cultured mammalian cells" *Nature* 411(6836):494-498 (2001).
Elbashir et al., "Functional Anatomy of siRNAs for mediating efficient RNAi in *Drosophila melanogaster* embryo lysate" *EMBO J.* 20(23):6877-6888 (2001).
Elbashir et al., "Analysis of gene function in somatic mammalian cells using small interfering RNAs," *Methods* 26:199-213 (2002).
Elbashir et al., "RNA Interference is Mediated by 21- and 22-nucleotide RNAs," *Genes Dev.* 15:188-200 (2001).
Elroy-Stein et al., "Cytoplasmic expression system based on constitutive synthesis of bacteriophage T7 RNA polymerase in mammalian cells," *Proc. Natl. Acad. Sci. USA* 87:6743-6747 (1990).

(56) References Cited

OTHER PUBLICATIONS

Engdahl et al., "A two unit antisense RNA cassette test system for silencing of target genes," *Nucl. Acids Res.* 25(16):3218-3227 (1997).
English et al., "Suppression of Virus Accumulation in Transgenic Plants Exhibiting Silencing of Nuclear Genes," *Plant Cell* 8(2):179-188 (1996).
Escude et al., "Stable triple helices formed by oligonucleotide N3' → P5' phosphoramidates inhibit transcription elongation," *Proc. Natl. Acad. Sci. USA* 93:4365-4369 (Apr. 1996).
European Search Report mailed Jun. 3, 2005, for European patent application No. 04015041.9, filed Mar. 19, 1999, 4 pages.
Extract from Henderson's Dictionary of Biological Terms, 10$^{th}$ Edition, "blastomere," (1989).
Extract from Henderson's Dictionary of Biological Terms, 10$^{th}$ Edition, "somatic cells," (1989).
Extract from the New Oxford Dictionary of English, "somatic cells," (1998).
Extract from Henderson's Dictionary of Biological Terms, 10$^{th}$ Edition, "totipotent," (1989).
Faruqi et al., "IFN-γ Inhibits Double-Stranderd RNA-Induced E-Selectin Expression in Human Endothelial Cells," *J. Immunol.* 159:3989-3994 (1997).
Fiaschi et al., "The 5'-untranslated region of the human muscle acylphosphatase mRNA has an inhibitory effect on protein expression," *FEBS Lett.* 417:130-134 (1997).
Finkler et al., "Immunity and resistance to the KP6 toxin of *Ustilago maydis*," *Mol. Gen. Genet.* 233:395-403 (1992).
Fire et al., "Potent and specific genetic interference by double-stranded RNA in *Caenorhabditis elegans*," *Nature* 391:806-811 (1998).
Fire et al., "Production of antisense RNA leads to effective and specific inhibition of gene expression in *C. elegans* muscle," *Development* 113:503-514 (1991).
Fire, "RNA-triggered gene silencing," *Trends Genet.* 15(9):358-363 (1999).
Flavell, "Inactivation of gene expression in plants as a consequence of specific sequence duplication" *Proc. Natl. Acad. Sci.* 99:3490-3496 (1994).
Francis et al., "Control of β-Interferon Expression in Murine Embryonal Carcinoma F9 Cells," *Mol. Cell. Biol.* 9:3553-3556 (1989).
Fraser et al., "Effects of c-*myc* first exons and 5' synthetic hairpins on RNA translation in oocytes and early embryos of *Xenopus laevis*," *Oncogene* 12(6):1223-1230 (1996).
Fuerst et al., "Eukaryotic transient-expression system based on recombinant vaccinia virus that synthesizes bacteriophage T7 RNA polymerase," *Proc. Natl. Acad. Sci. USA* 83:8122-8126 (1986).
Gao et al., "Human genes encoding u3 SnRNA associate with coiled bodies in interphase cells and are clustered on chromosome 17p11.2 in a complex inverted repeat structure," *Nucl. Acids Res.* 25:4740-4747 (1997).
Garrick et al., "Repeat-induced gene silencing in mammals," *Nature Genetics* 18(1):56-59 (1998).
Gervaix et al., "Multigene Antiviral Vectors Inhibit Diverse Human Immunodeficiency Virus Type 1 Clades," *J. Virol.* 71(4):3048-3053 (1997).
Gessani et al., "Activators of Protein Kinase C Enhance Accumulation of interferon-β mRNA in Murine Cell Lines," *J. Interferon Res.* 9:543-550 (1989).
Gimmi et al., "alterations in the pre-mRNA topology of the bovine growth hormone polyadenylation region decrease poly(A) site efficiency," *Nucl. Acids Res.* 17:6983-6998 (1989).
Giordano et al., "RNAi Triggered by Symmetrically Transcribed Transgenes in *Drosophila melanogaster*" *Genetics* 160:637-648 (2000).
Giovannangeli et al., "Accessibility of nuclear DNA to triplex-forming oligonucleotides: the integrated HIV-1 provirus as a target," *Proc. Natl. Acad. Sci. USA* 94:79-84 (1997).
Gitlin et al., "Poliovirus Escape from RNA Interference: Short Interfering RNA-Target Recognition and Implications for Therapeutic Approaches," *J. Virol.* 79:1027-1035 (2005).
Goff et al., "Analysis of Hoxd-13 and Hoxd-11 Misexpression in Chick Limb Buds Reveals that Hox Genes Affect Both Bone Condensation and Growth," *Development* 124:627-636 (1997).
Good et al., "Expression of small, therapeutic RNAs in human cell nuclei," *Gene Ther.* 4(1): 45-54 (1997).
Grabarek et al., "Efficient Delivery of dsRNA into Zona-enclosed Mouse Oocytes and Preimplantation Embryos by Electroporation," *Genesis* 32(4):269-276 (2002).
Grabarek et al., "RNA Interference by Production of Short Hairpin dsRNA in ES Cells, Their Differentiated Derivatives, and in Somatic Cell Lines," *Biotechniques* 34(4):734-744 (Apr. 2003).
Graham et al., "A Rapid and Reliable Method to Create Tandem Arrays of Short DNA Sequences," *BioTech.* 13:780-789 (1992).
Graham et al., "RNA Transcripts of the Human Immunodeficiency Virus Transactivation Response Element Can Inhibit Action of the Viral Transactivator," *Proc. Natl. Acad. Sci. USA* 87:5817-5821 (1990).
Grant, "Dissecting the Mechanisms of Posttranscriptional Gene Silencing: Divide and Conquer" *Cell* 96:303-306 (1999).
Grasby et al., "Purine Functional Groups in Essential Residues of the Hairpin Ribozyme Required for Catalytic Cleavage of RNA" *Biochemistry* 34:4068-4076 (1995).
Griffey et al., "2'O-Aminopropyl Ribonucleotides: A Zwitterrionic Modification That Enhances the Exonuclease Resistance and Biological Activity of Antisense Oligonucleotides" *J. Med. Chem.* 39:5100-5109 (1996).
Groger et al., "Directional Antisense and cDNA Cloning Using Epstein-Barr Virus Episomal Expression Vectors," *Gene* 81:285-294 (1989).
Gryaznov et al., "Template Controlled Coupling and Recombination of Oligonucleotide Blocks Containing Thiophosphoryl Groups" *Nucl. Acids Res.* 21(6):1403-1408 (1993).
Gura, "A silence that speaks volumes," *Nature* 404:804-808 (2000).
Ha et al., "A Bulged lin-4/lin-14 RNA Duplex is Sufficient for *Caenorhabditis elegans* lin-14 Temporal Gradient Formation" *Genes Dev.* 10:3041-3050 (1996).
Hacker et al., "Expression of SRY, The Mouse Sex Determining Gene," *Development* 121:1603-1614 (1995).
Haggarty et al., "An embryonic DNA-binding protein specific for a region of the human IFNβ$_1$ promoter," *Nucl. Acids Res.* 16:10575-10592 (1988).
Haines et al., "Cellular Response to Double-Stranded RNA," *J. Cell. Biochem.* 46:9-20 (1991).
Hamilton et al., "A transgene with repeated DNA causes high frequency, post-transcriptional suppression of ACC-oxidase gene expression in tomato," *Plant J.* 15(6):737-746 (1998).
Hamilton et al., "A Species of Small Antisense RNA in Post-transcriptional Gene Silencing in Plants," *Science* 286:950-952 (1999).
Hammond et al., "An RNA-directed nuclease mediates post-transcriptional gene silencing in *Drosophila* cells," *Nature* 404:293-296 (2000).
Hannon, "RNA Interference" *Nature* 418:244-251 (2002).
Harada et al., "Absence of the Type I IFN System in EC Cells: Transcriptional Activator (IRF-1) and Repressor (IRF-2) Genes are Developmentally Regulated," *Cell* 63:303-312 (1990).
Harbinder et al., "Genetically Targeted Cell Disruption in *Caenorhabditis Elegans*," *Proc. Natl. Acad. Sci. USA* 94:13128-13133 (1997).
Harborth et al. "Sequence, Chemical, and Structural Variation of Small Interfering RNAs and SHort Hairpin RNAs and the Effect on Mammalian Gene Silencing" *Antisense and Nucleic Acid Drug Development* 13:83-105 (2003).
Harborth et al. "Identification of essential genes in cultured mammalian cells using small interfering RNAs," *J. Cell Science* 114:4557-4565 (2001).
Harcourt et al., "Ebola Virus Inhibits Induction of Genes by Double-Stranded RNA in Endothelial Cells," *Virology* 252:179-188 (1998).

(56) References Cited

OTHER PUBLICATIONS

Harfe et al., "Analysis of a *Caenorhabdits elegans* Twist Homolog Identifies Conserved and Divergent Aspects of Mesodermal Patterning," *Genes Dev.* 12:2623-2635 (1998).
Henderson et al., "Instability of a Plasmid-Borne Interved Repeat in *Saccharomyces cerevisiae*," *Genetics* 134:57-62 (1993).
Henry et al., "Mechanism of interferon action. Translational control and the RNA-dependent protein kinase (PKR): antagonists of PKR enhance the translational activity of mRNAs that include a 161 nucleotide region from reovirus S1 mRNA," *J. Biol. Regulators Homeostat. Agents* 8:15-24 (1994).
Hirashima et al., "Artificial Immune System against Viral Infection Involving Antisense RNA targeted to the 5'-Terminal Noncoding Region of Coliphage SP RNA," *J. Biochem.* 106:163-166 (1989).
Hirashima et al., "Engineering of the mRNA-interfering Complementary RNA Immune System Against Viral Infection," *Proc. Natl. Acad. Sci. USA* 83:7726-7730 (1986).
Hoke et al., "Effects of Phosporothioate Capping on Antisense Oligonucleotide Stability, Hybridization and Antiviral Efficacy Versus Herpes Simplex Virus Infection" *Nucl. Acids Res.* 19(20):5743-5748 (1991).
Holen et al., "Positional effects of short interfering RNAs targeting the human coagulation trigger Tissue Factor" *Nucl. Acids Res.* 30(8):1757-1766 (2002).
Hungarian Patent Office Search Report mailed Jul. 13, 2004 for Hungarian patent application No. P0101225, 1 page.
Imazeki et al., "Integrated Structures of Duck Hepatitis B Virus DNA in Hepatocellular Carcinoma," *J. Virol.* 62:861-865 (1988).
International Search Report mailed on May 10, 1999, for PCT patent application No. PCT/AU99/00195, filed on Mar. 19, 1999: 3 pages.
International Search Report mailed on May 10, 2001, for PCT patent application No. PCT/AU01/00297, filed on Mar. 16, 2001: 3 pages.
International Search Report mailed on Nov. 14, 2002, for PCT patent application No. PCT/AU02/01326, filed on Sep. 27, 2002: 5 pages.
Invitrogen, Map for pcDNAI, 1 page (date unknown).
James, "Towards gene-inhibition therapy: a review of progress and prospects in the field of antiviral antisense nucleic acids and ribozymes," *Antiviral Chem. & Chemother.* 2(4):191-214 (1991).
Jen et al., "Suppression of Gene Expression by Targeted Disruption of Messenger RNA: Available Options and Current Strategies," *Stem Cells* 18:307-319 (2000).
Jorgensen et al., "Do Unintended Antisense Transcripts Contribute to Sense Cosuppression in Plants," *TIG* 15:11-12 (1999).
Jorgensen, "Altered gene expression in plants due to trans interactions between homologous genes," *Trends Biotechnol.* 8(12):340-344 (1990).
Jorgensen et al., "Chalcone synthase cosuppression phenotypes in petunia flowers: comparison of sense vs. antisense constructs and single-copy vs. complex T-DNA sequences," *Plant Mol. Biol.* 31(5):957-973 (1996).
Kappel et al., "Regulating gene expression in transgenic animals," *Curr. Opin. Biotechnol.* 3:548-553 (1992).
Katsuki et al., "Conversion of Normal Behavior to Shiverer by Myelin Basic Protein Antisense cDNA in Transgenic Mice," *Science* 241(4865):593-595 (1988).
Kennerdell et al., "Heritable Gene Silencing in *Drosophila* Using Double-Stranded RNA" *Nat. Biotechnol.* 18:896-898 (2000).
Kennerdell et al., "Use of dsRNA-Mediated Genetic Interference to Demonstrate that frizzled and frizzled 2 Act in the Wingless Pathway," *Cell* 95:1017-1026 (1998).
Kibler et al., "Double-Stranded RNA is a Trigger for Apoptosis in Vaccinia Virus-Infected Cells." *J. Virol.* 71:1992-2003 (1997).
Kirchhoff et al., "IRF-1 induced cell growth inhibition and interferon induction requires the activity of the protein kinase PKR," *Oncogene* 11:439-445 (1995).
Kitabwalla et al., "RNA Interference—A New Weapon Against HIV and Beyond" *New Engl. J. Med.* 347(17):1364-1367 (2002).
Klaff et al., "RNA Structure and the Regulation of Gene Expression," *Plant Mol. Biol.* 32:89-106 (1996).
Klink et al., "The Efficacy of RNAi in the Study of the Plant Cytoskeleton" *J. Plant Growth Reg.* 19:371-384 (2000).
Knoester et al., "Modulation of stress-inducible ethylene biosynthesis by sense and antisense gene expression in tobacco," *Plant Science* 126:173-183 (1997).
Kook et al., "The effect of antisense inhibition of urokinase receptor in human squamous cell carcinoma on malignancy," *EMBO J.* 13(17):3983-3991 (1994).
Kowolik et al., "Locus Control Region of the Human CD2 Gene in a Lentivirus Vector Confers Position-Independent Transgene Expression" *J. Virol.* 75(10):4641-4648 (2001).
Kowolik et al., "Preferential Transduction of Human Hepatocytes with Lentiviral Vectors Pseudotyped by Sendai Virus F Protein" *Molecular Therapy* 5(6):762-769 (2002).
Kozak, "Influences of mRNA secondary structure on initiation by eukaryotic ribosomes," *Proc. Natl. Acad. Sci. USA* 83:2850-2854 (1986).
Kozak, "Circumstances and Mechanisms of Inhibition of Translation by Secondary Structure in Eucaryotic mRNAs," *Mol. Cell. Biol.* 9:5134-5142 (1989).
Kreutzer, "Specific inhibition of viral gene expression by double-stranded RNA in vitro" Fall Meeting S169.
Krystal et al., "Multiple Mechanisms for Transcriptional Regulation of the myc Gene Family in Small-Cell Lung Cancer," *Mol. Cell. Biol.* 8:3373-3381 (1988).
Krystal et al., "N-*myc* mRNA Forms an RNA-RNA Duplex with Endogenous Antisense Transcripts," *Mol. Cell. Biol.* 10:4180-4191 (1990).
Kumar et al., "Antisense RNA: Function and Fate of Duplex RNA in Cells of Higher Eukaryotes" *Microbiology and Molecular Biology Reviews* 62(4):1415-1434 (1998).
Kunz et al., "Developmentally regulated silencing and reactivaation of tobacco chitinase transgene expression," *Plant J.* 10(3):437-450 (1996).
Kurreck, "Antisense technologies. Improvement therough novel chemical modifications," *Eur. J. Biochem* 270:1628-1644 (2003).
Leach et al., "Viability of λ phages carrying a perfect palindrome in the absence of recombination nucleases," *Nature* 305:448-451 (1983).
Leach et al., Long DNA palindromes, cruciform structures, genetic instability and secondary structure repair, *BioEssays* 16:893-900 (1994).
Lee et al., "The *C. elegans* Heterochronic Gene *lin-4* Encodes Small RNAs with Antisense Complementarity to *lin-14*," *Cell* 75:843-854 (1993).
Lee et al., "The Hemagglutinin Genes *hagB* and *hagC* of *Porphyromonas gingivalis* Are Transcribed in Vivo as Shown by Use of a New Expression Vector," *Infect. Immun.* 64:4802-4810 (1996).
Lee et al., "Inhibition of Human Immunodeficiency Virus Type 1 in Human T Cells by a Potent Rev Response Element Decoy Consisting of 13-Nucleotide Minimal Rev-Binding Domain," *J. Virol.* 68(12):8254-8264 (1994).
Lee et al., "Post-transcriptional gene silencing of ACC synthase in tomato results from cytoplasmic RNA degradation," *Plant J.* 12(5):1127-1137 (1997).
Li et al., "Double-Stranded RNA Injections Produces Null Phenotype in Zebrafish" *Dev. Biol.* 217(2):394-405. Erratum in: *Dev. Biol.* 220(2):432 (2000).
Liehaber et al., "Translation Inhibition by an mRNA Coding Region Secondary Structure is Determined by Its Proximity to the *AUG* Initiation by Codon," *J. Mol. Biol.* 226:609-621 (1992).
Lin et al., "Policing Rogue Genes" *Nature* 402:128-129 (1999).
Lindbo et al., "Induction of a Highly Specific Antiviral State in Transgenic Plants: Implications for Regulation of Gene Expression and Virus Resistance," *Plant Cell* 5(12):1749-1759 (1993).
Lindbo et al., "Pathogen-Derived Resistance to a Potyvirus: Immune and Resistant Phenotypes in Transgenic Tobacco Expressing Altered Forms of a Potyvirus Coat Protein Nucleotide Sequence," *Mol. Plant-Microbe Interactions* 5(2):144-153 (1992).
Lingelbach et al., "An extended RNA/RNA duplex structure within the coding region of mRNA does not block translational elongation," *Nucl. Acids Res.* 16:3405-3414 (1988).

(56) References Cited

OTHER PUBLICATIONS

Lipinski et al., "Experimental and computational approaches to estimate solubility and permeability in drug discovery and development settings" *Advanced Drug Delivery Reviews* 23:3-25 (1997).
Lisziewicz et al., "Tat-Regulated Production of Multimerized TAR RNA Inhibits HIV-1 Gene Expression" *New Biologist* 3:82-89 (1991).
Lisziewicz et al., "Inhibition of human immunodeficiency virus type 1 replication by regulated expression of a polymeric Tat activation response RNA decoy as a strategy for gene therapy in AIDS," *Proc. Natl. Acad. Sci. USA* 90:8000-8004 (1993).
Lloyd et al., "Identification and Genetic Analysis of sbcC mutations in commonly used recBC sbcB strains of *Escherichia coli* K-12," *J. Bacteriol.* 164:836-844 (1985).
Longman et al., "Functional characterization of SR and SR-related genes in *Caenorhabditis elegans*," *EMBO J.* 19:1625-1637 (2000).
Loomis et al., "Antisense RNA Inhibition of Expression of a Pair of Tandemly Repeated Genes Results in a Delay in Cell-Cell Adhesion in *Dictyostelium*," *Antisense Res. Dev.* 1:255-260 (1991).
Ma et al., "Design and Synthesis of RNA Miniduplexes via a Synthetic Linker Approach" *Biochemistry* 32:1751-1758 (1993).
Mace et al., "Interferon-regulated viral replication in chronically HIV1-infected promonocytic U937 cells," *Res. Viral.* 142:213-220 (1991).
Majumdar et al., "Targeted Gene Knockout Mediated by Triple Helix Forming Oligonucleotides" *Nat. Genet.* 20:212-214 (1998).
Manche et al., "Interactions Between Double Stranded RNA Regulators and the Protein Kinase DAI," *Mol. Cell. Biol.* 12(11):5238-5248 (1992).
Marathe et al., "RNA virues as inducers, suppressors and targets of post-transcriptional gene silencing," *Plant Molecular Biology* 43:295-306 (2000).
Marcus et al., "The pGEM®-T and pGEM®-T Easy Vector Systems," *Promega Notes Magazine*, No. 58, 36-38 (1996).
Marx, "Interfering With Gene Expression," *Science* 288:1370-1372 (2000).
Matthieu et al., "Myelin-Deficient Mutant Mice: An in Vivo Model for Inhibition of Gene Expression by Natural Antisense RNA," *Ann. N.Y. Acad. Sci.* 660:188-192 (1992).
Matzke et al., "Epigenetic silencing of plant transgenes as a consequence of diverse cellular defence responses," *Cell. Mol. Life Sci.* 54(1):94-103 (1998).
Matzke et al., "How and Why Do Plants Inactivate Homologous (Trans)genes" *Plant Physiol.* 107:679-685 (1995).
Matzke et al., "RNAi Extends Its Reach" *Science* 301:1060-1061 (2003).
Mayne et al., "SV40-transformed normal and DNA-repair-deficient human fibroblasts can be transfected with high frequency but retain only limited amounts of integrated DNA," *Gene* 66:65 (1988).
McCormack et al., "Mechanism of Interferon Action: Identification of a RNA Binding Domain within the N-terminal Region of the Human RNA-Dependent P1/eIF-2α Protein Kinase," *Virology* 188:47-56 (1992).
McKenzie et al.., "Xenotransplantation," Eds. Ginns et al., in *Transplantation*, Science Inc., pp. 827-874 (1999).
McManus et al., "Gene Silencing in Mammals by Small Interfering RNAs" *Nat. Rev. Genet.* 3(10):737-747 (2002).
McManus et al., "Gene Silencing using micro-RNA designed hairpins" *RNA* 8:842-850 (2002).
McManus et al., "Small Interfering RNA-Mediated Gene Silencing in T Lymphocytes," *J. Immunol.* 169:5754-5760 (2002).
McNair et al., "Hepatitis delta virus replication in vitro is not affected by interferon-α or -γ despite intact cellular responses to the interferon and dsRNA," *J. Gen. Virol.* 75:1371-1378 (1994).
Mercola et al., "Antisense Approaches to Cancer Gene Therapy," *Cancer Gene Ther.* 2:47-59 (1995).
Mette et al., "Transcriptional Silencing and Promoter Methylation Triggered by Double-Stranded RNA," *EMBO J.* 19:5194-5201 (2000).
Metzlaff et al., "RNA-Mediated RNA Degradation and Chalcone Synthase A Silencing in Petunia," *Cell* 88:845-854 (1997).
Meyer, "Repeat-Induced Gene Silencing: Common Mechanisms in Plants and Fungi," *Biol. Chem. Hoppe-Seyler* 377(2):87-95 (1996).
Mikoshiba et al., "Chimeric and Molecular Genetic Analysis of Myelin-Deficient (Shiverer and Mld) Mutant Mice," *Ann. N.Y. Acad. Sci.* 605:166-182 (1990).
Mikoshiba et al., "Molecular biology of myelin basic protein: gene rearrangement and expression of anti-sense RNa in myelin-deficient mutants" *Comp. Biochem. Physiol.* 98:51-61 (1991).
Milhaud et al., "Free and Liposome-Encapsulated Double-Stranded RNAs as Inducers of Interferon, Interleukin-6, and Cellular Toxicity" *J. Interferon Res.* 11:261-265 (1991).
Minutes of Oral Proceeding dated Jul. 12, 2005, filed in EP 99 910 039.9.
Montgomery et al., "Double-stranded RNA as a mediator in sequence-specific genetic silencing and co-suppression," *TIG* 14(7):255-258 (1998).
Montgomery et al., "RNA as a target of double-stranded RNA-mediated genetic interference in *Caenorhabditis elegans*," *Proc. Natl. Acad. Sci. USA* 95:15502-15507 (1998).
Morishita et al., "Role of Transcriptional cis-Elements, Angiotensinogen Gene-Activating Elements, of Angiotensinogen Gene in Blood Pressure Regulation," *Hypertension* 27:502-507 (1996).
Moroni et al., "EGF-R Antisense RNA Blocks Expression of the Epidermal Growth Factor Receptor and Suppresses the Transforming Phenotype of a Human Carcinoma Cell Line," *J. Biol. Chem.* 267(4):2714-2722 (1992).
Morris et al., "Small Interfering RNA-Induced Transcriptional Gene Silencing in Human Cells," *Science* 305:1289-1292 (2004).
Moss et al., "The Cold Shock Domain Protein LIN-28 Controls Development Timing in *C. elegans* and is Regulated by the lin-4 RNA" *Cell* 88:637-646 (1997).
Mueller et al., "Homology-dependent resistance: transgenic virus resistance in plants related to homology-dependent gene silencing," *Plant J.* 7(6):1001-1013 (1995).
Muskins et al., "Role of inverted DNA repeats in transcriptional and post-transcriptional gene silencing," *Plant Mol. Biol.* 43:243-260 (2000).
Nagy et al., "Glyceraldehyde-3-phosphate Dehydrogenase Selectively Binds AU-rich RNA in the $NAD^+$-binding Region (Rossmann Fold)," *J. Biol. Chem.* 270:2755-2763 (1995).
Napoli et al., "Introduction of a Chimeric Chalcone Synthase Gene into Petunia Results in Reversible So-Suppression of Homologous Genes in trans," *Plant Cell* 2(4):279-289 (1990).
Nellen, et al., "What makes an mRNA anti-sense-itive?" *Trends in Biochemical Sciences* 18(11):419-423 (1993).
Ngo et al., "Double-Stranded RNA Induces mRNA Degradation in *Trypanosoma brucei*" *Proc. Natl. Acad. Sci. USA* 95:14687-14692 (1998).
Nielsen et al., "A novel class of conformationally restricted oligonucleotide analogues: synthesis of 2', 3'-bridged monomers and RNA-selective hybridisation" *Chem. Commun.* 9:825-826 (1997).
Nieth et al., "Modulation of the classical multidrug resistance (MDR) phenotype by RNA interference (RNAi)," *FEBS Letters* 545:144-150 (2003).
Nikiforov et al., "Oligodeoxynucleotides containing 4-thiothymidine and 6-thiodeoxyguanosine as affinity labels for the Eco RV restriction endonuclease and modification methylase," *Nucl. Acids Res.* 20(6):1209-1214 (1992).
Noguchi et al., "Characterization of an Antisense Inr Element in the eIF-2α Gene," *J. Biol. Chem.* 269:29161-29167 (1994).
Oates et al., "Too Much Interference: Injection of Double-Stranded RNA Has Nonspecific Effects in the Zebrafish Embryo," *Developmental Biology* 224:20-28 (2000).
Okano et al., "Myelin Basic Protein Gene and the Function of Antisense RNA in its Repression in Myelin-Deficient Mutant Mouse," *J. Neurochem.* 56:560-567 (1991).
Opalinska, et al., "Nucleic-Acid Therapeutics: Basic Principles and Recent Applications" *Nature Reviews* 1:503-514 (2002).

(56) References Cited

OTHER PUBLICATIONS

Paddison et al., "Short hairpin RNAs (shRNAs) induce sequence-specific silencing in mammalian cells" *Genes and Development* 16:948-958 (2002).
Paddison et al., "RNA interference: the new somatic cell genetics?" *Cancer Cell* 2:17-23 (2002).
Paddison et al., "Stable suppression of gene expression by RNAi in mammalian cells," *Proc. Natl. Acad. Sci. USA* 99:1443-1448 (2002).
Pal-Bhadra et al., "Cosuppression in *Drosophila:* Gene Silencing of Alcohol dehydrogenase by white-Adh Transgenes is Polycomb Dependent," *Cell* 90(3):479-490 (1997).
Palauqui et al., "Systemic acquired silencing: transgene-specific post-transcriptional silencing is transmitted by grafting from silenced stocks to non-silenced scions," *EMBO J.* 16:4738-4745 (1997).
Palaugui et al., "Transgenes are dispensable for the RNA degradation step of cosuppression," *Plant Biology* 95:9675-9680 (1998).
Palmiter et al., "Transmission Distortion and Mosaicism in an Unusual Transgenic Mouse Pedigree," *Cell* 36:869-877 (1984).
Pang et al., "Nontarget DNA sequences reduce the transgene length necessary for RNA-mediated tospovirus resistance in transgenic plants," *Proc. Natl. Acad. Sci. USA* 94(15):8261-8266 (1997).
Park et al., "Specific inhibition of HIV-1 gene expression by double-stranded RNA," *Nucl. Acids Res.* Suppl. No. 1:219-220 (2001).
Park et al., "Prevention of HIV-1 infection in human peripheral blood mononuclear cells by specific RNA interference," *Nucl. Acids Res.* 30(22):4830-4835 (2002).
Park et al., "Gene silencing mediated by promotor homology occurs at the level of transcription and results in meiotically heritable alterations in methylation and gene activity," *Plant J.* 9(2):183-194 (1996).
Pe'ery et al., "Synthesis and Purification of Single-Stranded RNA for Use in Experiments with PKR and in Cell-Free Translation Systems," *Methods* 11:371-381 (1997).
Pegram et al., "Phase II study of Receptor-Enhanced Chemosensitivity Using Recombinant Humanized Anti-p185$^{HER2neu}$ Monoclonal Antibody Plus Cisplatin in Patients With HER2/Neu-Overexpressing Metastatic Breast Cancer Refractory to Chemotherapy Treatment" *Journal of Clinical Oncology* 16(8):2659-2671 (1998).
Pelletier et al., "Insertion mutagenesis to increase secondary structure within the 5' noncoding region of a eukaryotic mRNA reduces translational efficiency," *Cell* 40:515-526 (1985).
Peng et al., "Development of an MFG-Based Retroviral Vector System for Secretion of High Levels of Functionally Active Human BMP4" *Molecular Therapy* 4(2):95-104 (2001).
Peyman et al., "Molecular Biology and The Vascular Surgeon," in *Basic Science of Vascular Disease*, Chapter 2, pp. 17-68 (1997).
Piccin et al., "Efficient and Heritable Functional Knock-out of an Adult Phenotype in *Drosophila* using a GAL4-Driven Hairpin RNA Incorporating a Heterologous Spacer," *Nucl. Acids Res.* 29(12) E55:1-5 (2001).
Plasterk et al., "The Silence of the Genes," *Curr. Opin. Gen. Dev.* 10:562-567 (2000).
Pratt et al., "Regulation of In Vitro Translation by Double-stranded RNA in Mammalian Cell mRNA Preparations," *Nucl. Acids Res.* 16:3497-3510 (1988).
Putlitz et al., "Specific Inhibition of Hepatitis B Virus Replication by Sense RNA," *Antisense & Nucleic Acid Drug Development* 9:241-252 (1999).
Que et al., "The Frequency and Degree of Cosuppression by Sense Chalcone Synthase Transgenes Are Dependent on Transgene Promoter Strength and Are Reduced by Premature Nonsense Codons in the Transgene Coding Sequence," *Plant Cell* 9:1357-1368 (1997).
Que et al., "Homology-Based Control of Gene Expression Patterns in Transgenic Petunia Flowers," *Developmental Genetics* 22(1):100-109 (1998).
Randall et al., "Clearance of replicating hepatitis C virus replicon RNAs in cell culture by small interfering RNAs," *Proc. Natl. Acad. Sci. USA* 100(1):235-240 (2003).
Raponi et al., "Double-stranded RNA-mediated Gene Silencing in Fission Yeast," *Nucl. Acids Res.* 31:4481-4489 (2003).
Ratcliff et al., "A Similarity Between Viral Defense and Gene Silencing in Plants," *Science* 276:1558-1560 (1997).
Regalado, "Turning Off Genes Sheds New Light on How They Work" *The Wall Street Journal*, 4 pages. (Aug. 2002).
Reply to Summons to attend Oral Proceeding filed May 13, 2005 in European Patent Application No. 99 910 039.9, 9 pages.
Request for correction of minutes filed Aug. 2, 2005 in EP 99 910 039.9, 3 pages.
Resnekov et al., "RNA Secondary Structure Is an Integral Part of the in Vitro Mechanism of Attenuation in Simian Virus 40," *J. Biol. Chem.* 264:9953-9959 (1989).
Reuben et al., "Cloning and Expression of The Rabbit Gastric CCK-A Receptor," *Biochim. Biophys. Acta* 1219:321-327 (1994).
Robertson et al., "Age-dependent silencing of globin transgenes in the mouse," *Nucl. Acids Res.* 24:1465-1471 (1996).
Rocheleau et al., "Wnt Signaling and an APC-Related Gene Specify Endoderm in Early *C. elegans* Embryos," *Cell* 90:707-716 (1997).
Rodriguez et al., "Regulated Expression of Nuclear Genes by T3 RNA Polymerase and lac Repressor, Using Recombinant Vaccinia Virus Vectors," *J. Virol.* 64:4851-4857 (1990).
Romano et al., "Quelling: transient inactivation of gene expression in *Neurospora crassa* by transformation with homologous sequences," *Mol. Microbiol.* 6(22):3343-3353 (1992).
Roy et al., "Effect of mRNA secondary structure on the efficiency of Translational Initiation by Eukaryotic Ribosomes," *Eur. J. Biochem.* 191:647-652 (1990).
Ruskin et al., "Mutations in POL1 Increase the Mitotic Instability of Tandem Inverted Repeats in *Saccharomyces cerevisiae*," *Genetics* 133:43-56 (1993).
Sabl et al., "Copy Number and Orientation Determine the Susceptibility of a Gene to Silencing by Nearby Heterochromatin in *Drosophila*," *Genetics* 142:447-458 (1996).
Sadiq et al., "Developmental Regulation of Antisense-Mediated Gene Silencing in *Dictyostelium*," *Antisense Research & Development* 4(4):263-267 (1994).
Sarver et al., "Ribozymes as Potential Anti-HIV-1 Therapeutics Agents" *Science* 247:1222-1225 (1990).
Schaefer et al., "Antisense RNA control of gene expression in bacteriophage P22. I. Structures of sar RNA and its target, ant mRNA," *RNA* 3(2):141-156 (1997).
Schaller, "The Role of Sterols in Plant Growth and Development," *Prog. Lipid Res.* 42:163-175 (2003).
Schmidt et al., "Cycloheximide Induction of Aflatoxin Synthesis in a Nontoxigenic Strain of *Aspergillus flavus*" *Bio/Technology* 1:794-795 (1983).
Schmidt, "RNA Interference Detected 20 years ago," *Nat. Biotechnol.* 22:267-268 (2004).
Schmidt et al., "Viral Influences on Aflatoxin Formation by *Aspergillus flavus*," *Appl. Microbiol. Biotechnol.* 24:248-252 (1986).
Schmitt et al., "Characterization of cloned sequences complementary to F9 cell double-stranded RNA and their expression during differentiation," *Differentiation* 30:205-210 (1986).
Schramke et al., "Hairpin RNAs and Retrotransposon LTRs Effect RNAi and Chromatin-Based Gene Silencing" *Science* 301:1069-1074 (2003).
Schwarz et al., "Evidence that siRNAs Function as Guides, Not Primers in the *Drosophila* and Human RNAi Pathways," *Molecular Cell* 10:537-548 (2002).
Selker, "Gene Silencing: repeats that count," *Cell* 97(2):157-160 (1999).
Shaffer, "RNAi Shakes up Bio CEO Investor Conference," *Biotech News* 24:30 (2004).
Sharp, "RNAi and Double-Strand RNA," *Genes Dev.* 13:139-141 (1999).
Shi et al., "A CBP/p300 Homolog Specifies Multiple Differentiation Pathways in *Caenorhabditis elegans*" *Genes Dev.* (12)7:943-955 (1998).
Shinagawa et al., "Generation of Ski-knockdown mice by expressing a long double-strand RNA from an RNA polymerase II promoter," *Genes Dev.* 17:1340-1345 (2003).
Sijen et al., "RNA-Mediated Virus Resistance: Role of Repeated Transgenes and Delineation of Targeted Regions," *Plant Cell* 8(12):2277-2294 (1996).

(56) References Cited

OTHER PUBLICATIONS

Silverman, "Role of Sequences Within the First Intron in the Regulation of Expression of Eukaryotic Initiation Factor 2α," *J. Biol. Chem.* 267:9738-9742 (1992).

Simons, "Naturally Occurring Antisense RNA Control—A Brief Review," *Gene* 72:35-44 (1988).

Singer et al., "Genetic and Epigenetic Inactivation of Repetitive Sequences in *Neurospora crassa:* RIP, DNA Methylation, and Quelling," *Current Topics in Microbiology and Immunology* 197:165-177 (1995).

Sinha, "Large-Scale Synthesis: Approaches to Large-Scale Synthesis of Oligodeoxynecleotides and their Analog" *Antisense From Technology to Therapy Lab Manual and Textbook* 6:30-58 (1997).

Skripkin et al., "Psoralen Crosslinking Between Human Immunodeficiency Virus Type 1 RNA and Primer tRNA$_3^{Lys}$," *Nucl. Acids Res.* 24(3):509-514 (1996).

Smardon et al., "EGO-1 is related to RNA-directed RNA polymerase an functions in germ-line development and RNA interference in *C. elegans,*" *Current Biology* 10(4):169-178 (2000).

Smith et al., "Total Silencing by Intron-spliced Hairpin RNAs," *Nature* 407:319-320 (2000).

Smith et al., "Transgenic plant virus resistance mediated by untranslatable sense RNAs: expression, regulation and fate of nonessential RNAs," *Plant Cell* 6(10):1441-1453 (1994).

Smolinski et al., "Double-Stranded RNA Induces Sickle Erythrocyte Adherence to Endothelium: A Potential Role for Viral Infection in Vaso-Occlusive Pain Episodes in Sickle Cell Anemia," *Blood* 85:2945-2950 (1995).

Smyth, "Gene Silencing: Cosuppression at a Distance," *Current Biology* 7(12):R793-795 (1997).

Smythe et al., "Gene Therapeutic agents: The Use of Ribozymes, Antisene, and RNA Decoys for HIV-1 Infection," *Inflamm. Res.* 44:11-15 (1995).

Sonoda et al., "Asymmetric deletion of the junction between the short unique region and the inverted repeat does not affect viral growth in culture and vaccine-induced immunity against Marek's disease," *Vaccine* 14:277-284 (1996).

Stam et al., "The Silence of Genes in Transgenic Plants," *Annals of Botany* 79(1):3-12 (1997).

Statement setting out the Grounds of Appeal dated Nov. 11, 2005, filed in EP 99 910 039.9, 11 pages.

Stein et al., "Absence of non-specific effects of RNA interference triggered by long double-stranded RNA in mouse oocytes," *Dev. Biol.* 286(2):464-471 (Sep. 2005).

Steinecke et al., "Expression of a Chimeric Ribozyme Gene Results in Endonucleolytic Cleavage of a Target mRNA and a Concomitant Reduction of Gene Expression in vivo" *Nucl. Acids Res.* 23:1525-1530 (1992).

Stewart et al., "Lentivirus-delivered stable gene silencing by RNAi in primary cells," *RNA* 9:493-501 (2003).

Strauss, "Candidate Gene Silencers Found" *Science* 286: 886 (1999).

Sullenger et al., "Overexpression of TAR Sequences Renders Cells Resistant to Human Immunodeficiency Virus Replication," *Cell* 63:601-608 (1990).

Sullenger et al., "Expression of Chimeric tRNA-Driven Antisense Transcripts Renders NIH 3T3 Cells Highly Resistant to Moloney Murine Leukemia Virus Replication," *Mol. Cell. Biol.* 10:6512-6523 (1990).

Sullenger et al., "Analysis of trans-Acting Response Decoy RNA-Mediated Inhibition of Human Immunodeficiency Virus Type 1 Transactivation," *J. Virology* 65(12):6811-6816 (1991).

Sullenger, "Tethering Ribozymes to a Retroviral Packaging Signal for Destruction of Viral RNA" *Science* 262:1566-1569 (1993).

Sun et al., "Ribozyme-mediated Suppression of Moloney Murine Leukemia Virus and Human Immunodeficiency Virus Type I Replication in Permissive Cell Lines," *Proc. Natl. Acad. Sci. USA* 91:9715-9719 (1994).

Sun et al., "Resistance to human immunodeficiency virus type 1 infection conferred by trnasduction of human peripheral blood lymphocytes with ribozyme, antisense, or polymeric trans-activation response element constructs," *Proc. Natl. Acad. Sci. USA* 92:7272-7276 (1995).

Svoboda et al., "Selective reduction of dormant maternal mRNAs in mouse oocytes by RNA interference," *Development* 127(19):4147-4156 (2000).

Svoboda et al., "RNAi in Mouse Oocytes and Preimplantation Embryos: Effectiveness of Hairpin dsRNA" *Biochem. Biophys. Res. Commun.* 287(5):1099-1104 (2001).

Sweetser et al., "Transgenic mice containing intestinal fatty acid-binding protein-human growth hormone fusion genes exhibit correct regional and cell-specific expression of the reporter gene in their small intestine," *Proc. Natl. Acad. Sci. USA* 85:9611-9615 (1988).

Symington, "Role of RAD52 Epistasis Group Genes in Homologous Recombination and Double-Strand Break Repair," *Microbiol. Mol. Biol. Rev.* 66:630-670 (2002).

Tabara et al., "RNAi in *C. elegans:* Soaking in the Genome Sequence," *Science* 282:430-431 (1998).

Tabara et al., "The rde-1 Gene, RNA Interference, and Transposon Silencing in *C. elegans,*" *Cell* 99:123-132 (1999).

Table describing sequences used to inhibit viral replication. Annex A filed in EP 99 910 039.9.

Tanaka et al., "Sequence-specific interaction of α β-anomeric double-stranded DNA with the p50 subunit of NFκB: application to the decoy approach," *Nucl. Acids Res.* 22:3069-3074 (1994).

Tanzer et al., "Characterization of Post-Transcriptionally Suppressed Transgene Expression that Confers Resistance to Tobacco Etch Virus Infection in Tobacco," *Plant Cell* 9(8):1411-1423 (1997).

Tavernarakis et al., "Heritable and inducible genetic interference by double-stranded RNA encoded by transgenes," *Nature Genetics* 24:180-183 (2000).

Thomis, et al., "Mechanism of interferon action: Autoregulation of RNA-dependent P1/eIF-2α protein kinase (PKR) expression in transfected mammalian cells," *Proc. Natl. Acad. Sci. USA* 89:10837-10841 (1992).

Tijsterman et al., "The Genetics of RNA Silencing," *Ann. Rev. Genet.* 36:489-519 (2002).

Timmons et al., "Specific Interference by Ingested dsRNA," *Nature* 395:854 (1998).

Tosic et al., "Post-transcriptional events are responsible for low expression of myelin basic protein in myelin deficient mice: role of natural antisense RNA," *EMBO J.* 9:401-406 (1990).

Touchette, "Gene Therapy: Not Ready for Prime Time," *Nat. Med.* 2(1):7-8 (1996).

Tuschl et al., "Targeted mRNA degradation by double-stranded RNA in vitro," *Genes Dev.* 13:3191-3197 (1999).

Uhlmann et al., "Antisense Oligonucleotides: A New Therapeutic Principle" *Chemical Reviews* 9(4):544-584 (1990).

Ui-Tei et al., "Sensitive assay of RNA interference in *Drosophila* and Chinese hamster cultured cells firefly luciferase gene as target," *FEBS Letters* 479:79-82 (2000).

Usdin et al., "SP6 RNA Polymerase containing vaccinia virus for rapid expression of cloned genes in tissue culture," *BioTech.* 14:222-224 (1993).

Vaucheret et al., "A Transciptionally Active State is Required for Post-Transcriptional Silencing (Cosuppresion) of Nitrate Reductase Host Genes and Transgenes," *Plant Cell* 9(8):1495-1504 (1997).

Van der Krol et al., "Flavonoid Genes in Petunia: Addition of a Limited Number of Gene Copies May Lead to a Suppression of Gene Expression," *Plant Cell* 2(4):291-299 (1990).

Van der Krol et al., "Inhibition of flower pigmentation by antisense CHS genes: promoter and minimal sequence requirements for the antisense effect," *Plant Molecular Biology* 14(4):457-466 (1990).

Van Steeg et al., "The translation in vitro of rat ornithine decarboxylase mRNA is blocked by its 5' untranslated region in a polyamine-independent way," *Biochem. J.* 274:521-526 (1991).

Verma et al., "Gene therapy—promises, problems and prospects," *Nature* 389:239-242 (1997).

Viville, "Mouse Genetic Manipulation via Homologous Recombination," in *Transgenic Animals,* Houdebine (eds), Harwood academic publishers, France: pp. 307-321 (1997).

(56) References Cited

OTHER PUBLICATIONS

Voinnet et al., "Systemic Spread of Sequence-Specific Transgene RNA Degradation in Plants Is Initiated by Localized Introduction of Ectopic Promoterless DNA," *Cell* 95:177-187 (1998).
Volloch et al., "Evolutionarily conserved elements in the 5' untranslated region of β globin mRNA mediate site-specific priming of a unique hairpin structure during cDNA synthesis," *Nucl. Acids Res.* 22:5302-5309 (1994).
Wagner et al., "Double-stranded RNA poses puzzle," *Nature* 391:744-745 (1998).
Wall, "Transgenic Livestock: Progress and Prospects for the Future," *Theriogenology* 45:57-68 (1996).
Wang et al., "An Unusual Nucleoporin-Related Messenger Ribonucleic Acid is Present in the Germ Cells of Rat Testis," *Biol. Reprod.* 51:1022-1030 (1994).
Wang et al., "A factor IX-deficient mouse model for hemophilia B gene therapy," *Proc. Natl. Acad. Sci. USA* 94:11563-11566 (1997).
Wargelius et al., "Double-Stranded RNA Induces Specific Developmental Defects in Zebrafish Embryos," *Biochem. Biophys. Res. Commun.* 263:156-161 (1999).
Warren et al., "Comparison of Physical and Genetic Properties of Palindromic DNA Sequences," *J. Bacteriol* 161:1103-1111 (1985).
Wassenegger et al., "Signalling in gene silencing," *Trends Plant Sci.* 4(6):207-209 (1999).
Waterhouse et al., "Virus resistance and gene silencing in plants can be induced by simultaneous expression of sense and antisense RNA," *Plant Biology* 95:13959-13964 (1998).
Watson, "A new revision of the sequence of plasmid pBR322," *Gene* 70:399-403 (1988).
Weaver et al., "Introduction by molecular cloning of artifactual inverted sequences at the 5' terminus of the sense strand of bovine parathyroid hormone cDNA" *Proc. Natl. Acad. Sci. USA* 78:4073-4077 (1981).
Wess et al., "Early days for RNAi" *BioCentury* 11(12):A1-23 (2003).
Wianny et al., "Specific interference with gene function by double-stranded RNA in early mouse development," *Nature Cell Biology* 2:70-75 (2000).
Williams et al., "A mouse locus at which transcription from both DNA strands produces mRNAs complementary at their 3' ends," *Nature* 322:275-279 (1986).
Wolffe, "Repressed repeats express themselves," *Current Biol.* 7:R796 (1997).
Written Opinion mailed on Apr. 17, 2004, for PCT application No. PCT/AU03/01177 filed Sep. 9, 2003: 7 pages.
Wu et al., "Interferon-Stimulated Response Element and NFκB Sites Cooperate to Regulate Double-Stranded RNA-Induced Transcription of the IP-10 Gene," *J. Interferon Res.* 14:357-363 (1994).
Wu et al., "Double-stranded (ds) RNA Binding and Not Dimerization Correlates with the Activation of the dsRNA-dependent Protein Kinase (PKR)," *J. Biol. Chem.* 271:1756-1763 (1996).
Xiong et al., "Signaling properties of mouse and human corticotropin-releasing factor (CRF) receptors: decreased coupling efficiency of human type II CRF receptor," *Endocrin.* 136:1828-1834 (1995).
Yam et al., "Design of HIV Vectors for Efficient Gene Delivery into Human Hematopoietic Cells," *Molecular Therapy* 5(4):479-484 (2002).
Yamamoto et al., "Double-Stranded *nef*RNA Interferes with Human Immunodeficiency Virus Type 1 Replication," *Microbiol. Immunol.* 46(11):809-817 (2002).
Yamamoto et al., "Inhibition of transcription by the TAR RNA of HIV-1 in a nuclear extract of HeLa cells," *Nucl. Acids Res.* 25(17):3445-3450 (1997).
Yang et al., "Specific Double-Stranded RNA Interference in Undifferentiated Mouse Embryonic Stem Cells," *Mol. Cell. Biol.* 21(22):7807-7816 (2001).
Yarney et al., "Molecular cloning and expression of the ovine testicular follicle stimulating hormone receptor," *Mol. Cell. Endroc.* 93:219-226 (1993).

Yee et al., "Prospects for Gene Therapy Using HIV-Based Vectors," *Somatic Cell and Molecular Genetics* 26(1/6):159-173 (2001).
Yu et al., "Progress towards gene therapy of HIV infection," *Gene Therap.* 1:13-26 (1994).
Zakharyan et al., "Stimulation of double-spiral RNA Transformation of Prokaryotic and eukaryotic cells," *Doklady Akadem: Nauk SSR* 288:1251-1253 (1986).
Zamore et al., "RNAi: Double-Stranded RNA Directs the ATP-Dependent Cleavage of mRNA at 21 to 23 Nucleotide Intervals," *Cell* 101:25-33 (2000).
Zernika-Goetz, "Jumping the gun on mouse gene expression," *Nature* 405:733 (Jun. 2000).
Zernicka-Goetz et al., "Following cell fate in the living mouse embryo," *Development* 124:1133-1137 (1997).
Zhao et al., "Generating loss-of-function phenotype of the *fushi tarazu* gene with a targeted ribozyme in *Drosophila*," *Nature* 365:446-451 (1993).
Zhenhua et al., "Expression of Firefly Luciferase Gene in *Xenopus laevis* oocyte," *Chinese J. Biotech.* 7:279-284 (1991).
Akusjarvi et al., Molecular and Cellular Biology, 549-551 (1987). "A mechanism by which adenovirus virus-associated RNAi controls translation in a transient expression assay."
Bridge et al., Nature Genetics, 34:263-264 (2003). "Induction of an interferon response by RNAi vectors in mammalian cells."
Cronin et al, *The Lac Operator-Repressor System is Functional in the Mouse*, Genes & Development, 2001, vol. 15, pp. 1506-1517.
Khlebnikov et al., *Regulatable Arabinose-Inducible Gene Expression System With Consistent Control in All Cells of a Culture*, Journal of Bacteriology, Dec. 2000, vol. 182 No. 24, pp. 7029-7034.
RheoGene, www.rheogene.com.
Wang et al., Development of Gene-Switch Transgenic Mice That Inducibly Express Transforming Growth Factor Beta β in the Epidermis, Proc. Natl. Acad. Sci. USA, Jul. 1999, vol. 96, pp. 8483-8488.
Rendahl et al., Tightly Regulated Long-Term Erythropoietin Expression In Vivo Using Tet-Inducible Recombinant Adeno-Associated Viral Vectors, Human Gene Therapy, Jan. 20, 2002, vol. 13, pp. 335-342.
Lamartina et al., Stringent Control of Gene Expression In Vivo by Using Novel Doxycycline-Dependent Trans-Activators, Human Gene Therapy, Jan. 20, 2002, vol. 13, pp. 199-210.
Jaramillo et al., The Interferon System: A Review With Emphasis on the Role of PKR in Growth Control, Cancer Investigation, 1995, vol. 13 (3), pp. 327-338.
Platet et al., A New Bioassay Using Transient Transfection for Invasion-Related Gene Analysis, Invasion & Metastasis, 1998/99, vol. 18, pp. 198-208.
Harper et al., Analysis of the Neurotrophic Effects of GPI-1046 on Neuron Survival and Regeneration in Culture and In Vivo, Neuroscience, 1999, vol. 88 No. 1, pp. 257-267.
Tomaselli et al., Interactions of a Neuronal Cell Line (PC12) With Laminin, Collagen IV, and Fibronectin: Identification of Integrin-Related Glycoproteins Involved in Attachment and Process Outgrowth, The Journal of Cell Biology, Nov. 1987, vol. 105, pp. 2347-2358.
Marrack et al., Genomic-Scale Analysis of Gene Expression in Resting and Activated T Cells, Current Opinion in Immunology, 2000, vol. 12, pp. 206-209.
Harkin et al., Uncovering Functionally Relevant Signaling Pathways Using Microarray-Based Expression Profiling, The Oncologist, 2000, vol. 5, pp. 501-507.
Pelizzari et al, Quantitative Analysis of DNA Array Autoradiographs, Nucleic Acids Research, 2000, vol. 28 No. 22, pp. 4577-4581.
Marx, DNA Arrays Reveal Cancer in its Many Forms, Science, Sep. 8, 2000, vol. 289, Issue 5485, pp. 1670-1672.
Satoh et al., Site-Specific Integration of an Adeno-Associated Virus Vector Plasmid Mediated by Regulated Expression of Rep Based on Cre-loxP Recombination, Journal of Virology, Nov. 2000, pp. 10631-10638.
Trinh et al., Site-Specific and Directional Gene Replacement Mediated by Cre Recombinase, Journal of Immunological Methods, 2000, vol. 244, pp. 185-193.

(56) References Cited

OTHER PUBLICATIONS

Serov et al., Genetic Modification of Mammalian Genome at Chromosome Level, An. Acad. Bras, Ci., 2000, vol. 72(3), pp. 389-398.
Grez et al., New Vectors for Gene Therapy, Stem Cells, 1998, vol. 16 (Suppl 1), pp. 235-243.
Haren et al., Intergrating DNA: Transposases and Retroviral Integrases, Annu. Rev. Microbiol., 1999, vol. 53, pp. 245-281.
Baer et al., Transcriptional Properties of Genomic Transgene Integration Sites Marked by Electroporation or Retroviral Infection, Biochemistry, 2000, vol. 39, pp. 7041-7049.
Follenzi et al., Gene Transfer by Lentiviral Vectors is Limited by Nuclear Translocation and Rescued by HIV-1 Pol Sequences, Nature Genetics, Jun. 2000, vol. 25, pp. 217-222.
Hindmarsh et al., Retroviral DNA Integration, Microbiology and Molecular Biology Reviews, Dec. 1999, vol. 63 No. 4, pp. 836-843.
Darquet et al., Minicircle: An Improved DNA Molecule for In Vitro and In Vivo Gene Transfer, Gene Therapy, 1999, vol. 6, pp. 209-218.
Yu et al., A New System to Place Single Copies of Genes, Sites and LacZ Fusions on the *Escherichia Coli* Chromosome, Gene, 1998, vol. 223, pp. 77-81.
Darquet et al., A New DNA Vehicle for Nonviral Gene Delivery: Supercoiled Minicircle, Gene Therapy, 1997, vol. 4, pp. 1341-1349.
Koch et al., Site-Specific Integration of Targeted DNA Into Animal Cell Genomes, Gene, 2000, vol. 249, pp. 135-144.
Liu et al., Efficient Cre-IoxP-Induced Mitotic Recombination in Mouse Embryonic Stem Cells, Nature Genetics, Jan. 2002, vol. 30, pp. 66-72.
Awatramani et al., An Flp Indicator Mouse Expressing Alkaline Phosphatase from the ROSA26 Locus, Nature Genetics, Nov. 2001, vol. 29, pp. 257-259.
Heidmann et al., Reduction of Cre Recombinase Toxicity in Proliferating *Drosophila* Cells by Estrogen-Dependent Activity Regulation, Dev. Genes Evol., 2001, vol. 211, pp. 458-465.
Schaft et al, Efficient FLP Recombination in Mouse ES Cells and Oocytes, Genesis, 2001, vol. 31, p. 6-10.
Lorbach et al., Site-Specific Recombination in Human Cells Catalyzed by Phage λ Integrase Mutants, Mol. Biol., 2000, vol. 296, pp. 1175-1181.
Bushman et al., Tethering Human Immunodeficiency Virus Type 1 Preintegration Complexes to Target DNA Promotes Integration at Nearby Sites, Journal of Virology, Jan. 1997, pp. 458-464.
Reik et al., Silence Across The Border, Nature, May 2000, vol. 405, pp. 408-409.
Berger et al., Chromatin Goes Global, Molecular Cell, Aug. 2001, vol. 8, pp. 263-268.
Shibata et al., Homologous Genetic Recombination as an Intrinsic Dynamic Property of a DNA Structure Induced by RecA/Rad51-Family Proteins: A Possible Advantage of DNA over RNA as Genomic Material, PNAS, Jul. 7, 2001, vol. 98 No. 15, pp. 8425-8432.
Muyrers et al., Techniques: Recombinogenic Engineering—New Options for Cloning and Manipulating DNA, TRENDS in Biochemical Sciences, May 2001, vol. 26 No. 5, pp. 325-331.
Paul et al., Expression of *E. Coli* RecA Targeted to Mitochondria of Human Cells, Mutation Research, 2001, vol. 486, pp. 11-19.
Shcherbakova et al., Overexpression of Bacterial RecA Protein Stimulates Homologous Recombination in Somatic Mammalian Cells, Mutation Research, 2000, vol. 459, pp. 65-71.
Forster et al., Tetracycline-Inducible Expression Systems With Reduced Basal Activity in Mammalian Cells, Nucleic Acids Research, 1999, vol. 27 No. 2, pp. 708-710.
Pachuk et al., Chain Reaction Cloning: A One-Step Method for Directional Ligation of Multiple DNA Fragments, Gene, 2000, vol. 243, pp. 19-25.
Romano et al., Inhibition of Double-Stranded RNA-Dependent Protein Kinase PKR by Vaccinia Virus E3: Role of Complex Formation and the E3 N-Terminal Domain, Molecular and Cellular Biology, Dec. 1998, vol. 18 No. 12, pp. 7304-7316.
Pachuk et al., DNA Vaccines—Challenges in Delivery, Current Opinion in Molecular Therapeutics, 2000, vol. 2(2), pp. 188-198.
Pachuk et al., Characterization of a New Class of DNA Delivery Complexes Formed by the Local Anesthetic Bupivacaine, Biochimica et Biophysica Acta, 2000, vol. 1468, pp. 20-30.
Ghislain et al., The Interferon-Inducible Stat2: Stat1 Heterodimer Preferentially Binds In Vitro to a Consensus Element Found in the Promoters of a Subset of Interferon-Stimulated Genes, Journal of Interferon and Cytokine Research, 2001, vol. 21, pp. 379-388.
Igoucheva et al., Targeted Single-Base Correction by RNA-DNA Oligonucleotides, Human Gene Therapy, Nov. 2000, vol. 11, pp. 2307-2312.
Woodhouse et al., General Mechanisms of Metastasis, Cancer Supplement, Oct. 1997, vol. 80, No. 8, pp. 1529-1537.
Zhang et al., Binding of Double-Stranded RNA to Protein Kinase PKR is Required for Dimerization and Promotes Critical Autophosphorylation Events in the Activation Loop, The Journal of Biological Chemistry, 2001, vol. 276 No. 27, pp. 24946-24958.

* cited by examiner

POST-TRANSCRIPTIONAL GENE SILENCING USING EXPRESSED DOUBLE STRANDED RNA

CROSS-REFERENCE TO RELATED APPLICATION

This application is a divisional of and claims priority benefits from U.S. patent application Ser. No. 10/062,707, filed Jan. 31, 2002 which in turn claims priority from U.S. Provisional Applications 60/265,805 filed Jan. 31, 2001 and 60/339,260 filed Oct. 26, 2001 wherein the disclosures of these prior applications are incorporated by reference in their entirety into the present application.

BACKGROUND OF THE INVENTION

The invention relates to methods for identifying nucleic acid sequences that modulate the function of a cell, by the use of post-transcriptional gene silencing.

Double stranded RNA (dsRNA) has been shown to induce sequence-specific gene silencing in a number of different organisms. Gene silencing can occur through various mechanisms, one of which is post-transcriptional gene silencing (PTGS). In post-transcriptional gene silencing, transcription of the target locus is not affected, but the RNA half-life is decreased. The mechanisms by which PTGS occurs are not yet clear. Exogenous dsRNA has been shown to act as a potent inducer of PTGS in nematodes, trypanosomes, and insects. In addition, studies in *C. elegans* and *Drosophila* show that a few molecules of dsRNA per cell are sufficient to trigger a PTGS response. Furthermore, studies in mice have demonstrated that dsRNA can interfere with the expression of genes in mouse embryos.

There exists a need to identify molecules that selectively regulate the expression of genes in vertebrate cells without the associated toxicity of the interferon response. Such regulation should allow the downregulation of expression from genes whose gene products are detrimental to the cells.

SUMMARY OF THE INVENTION

In general the invention features high throughput methods of using PTGS to identify a nucleic acid sequence that modulates the function of a cell, gene expression of a target nucleic acid, or the biological activity of a target polypeptide. The method involves the use of specially constructed cDNA libraries derived from a cell, for example, a primary cell or a cell line that has an observable phenotype or biological activity, (e.g., an activity mediated by a target polypeptide or altered gene expression), that are transfected into cells to inhibit gene expression. This inhibition of gene expression alters the function of a cell, gene expression of a target nucleic acid, or the biological activity of a target polypeptide, and the nucleic acid sequence responsible for the modulation can be readily identified. The method may also utilize randomized nucleic acid sequences or a given sequence for which the function is not known. Although the use of PTGS as a validation strategy is known in the art, its use in screening techniques, as described herein, is novel.

Accordingly, in a first aspect, the invention features a method for identifying a nucleic acid sequence that modulates the function of a cell. The method involves: (a) transforming a population of cells with a double stranded RNA expression library, where the library is derived from the cells, where at least two cells of the population of cells are each transformed with a different nucleic acid from the double stranded RNA expression library, and where the nucleic acid is capable of forming double stranded RNA; (b) optionally selecting for a cell in which the nucleic acid is expressed in the cell; and (c) assaying for a modulation in the function of the cell, wherein a modulation identifies a nucleic acid sequence that modulates the function of a cell.

In a desirable embodiment of the first aspect of the invention, assaying for a modulation in the function of a cell comprises measuring cell motility, apoptosis, cell growth, cell invasion, vascularization, cell cycle events, cell differentiation, cell dedifferentiation, neuronal cell regeneration, or the ability of a cell to support viral replication.

In a second aspect, the invention features a method for identifying a nucleic acid sequence that modulates expression of a target nucleic acid in a cell. The method involves: (a) transforming a population of cells with a double stranded RNA expression library, where the library is derived from the cells, where at least two cells of the population of cells are each transformed with a different nucleic acid from the double stranded RNA expression library, and where the nucleic acid is capable of forming double stranded RNA; (b) optionally selecting for a cell in which the nucleic acid is expressed in the cell; and (c) assaying for a modulation in the expression of a gene in the cell, where a modulation identifies a nucleic acid sequence that modulates expression of a target nucleic acid in a cell.

In a desirable embodiment of the second aspect of the invention, the target nucleic acid is assayed using DNA array technology.

In a third aspect, the invention features a method for identifying a nucleic acid sequence that modulates the biological activity of a target polypeptide in a cell. The method involves: (a) transforming a population of cells with a double stranded RNA expression library, where the library is derived from the cells, where at least two cells of the population of cells are each transformed with a different nucleic acid from the double stranded RNA expression library, and where the nucleic acid is capable of forming double stranded RNA; (b) optionally selecting for a cell in which the nucleic acid is expressed in the cell; and (c) assaying for a modulation in the biological activity of a target polypeptide in the cell, wherein a modulation identifies a nucleic acid sequence that modulates the biological activity of a target polypeptide.

In one embodiment of any of the above aspects of the invention, in transforming step (a), the nucleic acid is stably integrated into a chromosome of the cell. Integration of the nucleic acid may be random or site-specific. Desirably integration is mediated by recombination or retroviral insertion. In addition, desirably a single copy of the nucleic acid is integrated into the chromosome. In another embodiment of any of the above aspects of the invention, in step (a) at least 50, more desirably 100; 500; 1000; 10,000; or 50,000 cells of the population of cells are each transformed with a different nucleic acid from the double stranded RNA expression library. In other embodiments, the population of cells is transformed with at least 5%, more desirably at least 25%, 50%, 75%, or 90%, and most desirably at least 95% of the double stranded RNA expression library. In yet another embodiment, the method further involves: (d) identifying the nucleic acid sequence by amplifying and cloning the sequence. Desirably amplification of the sequence involves the use of the polymerase chain reaction (PCR).

In other embodiments of any of the above aspects of the invention, the double stranded RNA expression library contains cDNAs or randomized nucleic acids. The double stranded RNA expression library may be a nuclear double stranded RNA expression library, in which case the double stranded nucleic acid is made in the nucleus. Alternatively, the double stranded RNA expression library may be a cytoplasmic double stranded RNA expression library, in which case the double stranded nucleic acid is made in the cytoplasm. In addition, the nucleic acid from the double stranded RNA expression library may be made in vitro or in vivo. In addition, the identified nucleic acid sequence may be located in the cytoplasm of the cell.

In still another embodiment of any of the above aspects of the invention, the nucleic acid is contained in a vector, for example a double stranded RNA expression vector. The vector may then be transformed such that it is stably integrated into a chromosome of the cell, or it may function as an episomal (non-integrated) expression vector within the cell. In one embodiment, a vector that is integrated into a chromosome of the cell contains a promoter operably linked to a nucleic acid encoding a hairpin or double stranded RNA. In another embodiment, the vector does not contain a promoter operably linked to a nucleic acid encoding a double stranded RNA. In this later embodiment, the vector integrates into a chromosome of a cell such that an endogenous promoter is operably linked to a nucleic acid from the vector that, encodes a double stranded RNA. Desirably, the double stranded RNA expression vector comprises at least one RNA polymerase II promoter, for example, a human CMV-immediate early promoter (HCMV-IE) or a simian CMV (SCMV) promoter, at least one RNA polymerase I promoter, or at least one RNA polymerase III promoter. The promoter may also be a T7 promoter, in which case, the cell further comprises T7 polymerase. Alternatively, the promoter may be an SP6 promoter, in which case, the cell further comprises SP6 polymerase. The promoter may also be one convergent T7 promoter and one convergent SP6 promoter. A cell may be made to contain T7 or SP6 polymerase by transforming the cell with a T7 polymerase or an SP6 polymerase expression plasmid, respectively. In some embodiments, a T7 promoter or a RNA polymerase III promoter is operably linked to a nucleic acid that encodes a small double stranded RNA (e.g., a double stranded RNA that is less than 200, 150, 100, 75, 50, or 25 nucleotides in length). In other embodiments, the promoter is a mitochondrial promoter that allows cytoplasmic transcription of the nucleic acid in the vector (see, for example, the mitochondrial promoters described in WO 00/63364, filed Apr. 19, 2000). Alternatively, the promoter is an inducible promoter, such as a lac (Cronin et al. *Genes & Development* 15: 1506-1517, 2001), ara (Khlebnikov et al., J. Bacteriol. 2000 December; 182(24):7029-34), ecdysone (Rheogene, www.rheogene.com), RU48 (mefepristone) (corticosteroid antagonist) (Wang X J, Liefer K M, Tsai S, O'Malley B W, Roop D R, Proc Natl Acad Sci USA. 1999 Jul. 20; 96(15):8483-8), or tet promoter (Rendal et al., Hum Gene Ther. 2002 January; 13(2):335-42. and Lamartina et al., Hum Gene Ther. 2002 January; 13(2):199-210) or a promoter disclosed in WO 00/63364, filed Apr. 19, 2000. In desirable embodiments, the inducible promoter is not induced until all the episomal vectors are eliminated from the cell. The vector may also comprise a selectable marker. In addition, these vectors may be used in combination with methods that inhibit or prevent an interferon response or double stranded RNA stress response, as described herein.

Desirably in a vector for use in any of the above aspects of the invention, the sense strand and the antisense strand of the nucleic acid sequence are transcribed from the same nucleic acid sequence using two convergent promoters. In another desirable embodiment, in a vector for use in any of the above aspects of the invention, the nucleic acid sequence comprises an inverted repeat, such that upon transcription, the nucleic acid forms a double stranded RNA.

In still other embodiments of any of the above aspects of the invention, the cell and the vector each further comprise a loxP site and site-specific integration of the nucleic acid into a chromosome of the cell occurs through recombination between the loxP sites. In addition, step (b) of any of the above aspects of the invention further involves rescuing the nucleic acid through Cre-mediated double recombination.

In still further embodiments of any of the above aspects of the invention, the identified nucleic acid sequence is located in the nucleus of the cell. Alternatively, the identified nucleic acid sequence may be located in the cytoplasm of the cell.

In yet another embodiment of any of the above aspects of the invention, the nucleic acid from the double stranded RNA expression library is at least 100, 500, 600, or 1000 nucleotides in length. In other embodiments of any of the above aspects of the invention, the nucleic acid from the double stranded RNA expression library is at least 10, 20, 30, 40, 50, 60, 70, 80, or 90 nucleotides in length. In yet other embodiments, the number of nucleotides in the nucleic acid from the double stranded RNA expression library is between 5-100 nucleotides, 15-100 nucleotides, 20-95 nucleotides, 25-90 nucleotides, 35-85 nucleotides, 45-80 nucleotides, 50-75 nucleotides, or 55-70 nucleotides, inclusive. In still other embodiments, the number of nucleotides in the nucleic acid from the double stranded RNA expression library is contained in one of the following ranges: 5-15 nucleotides, 15-20 nucleotides, 20-25 nucleotides, 25-35 nucleotides, 35-45 nucleotides, 45-60-nucleotides, 60-70 nucleotides, 70-80 nucleotides, 80-90 nucleotides, or 90-100 nucleotides, inclusive. In other embodiments, the nucleic acid contains less than 50,000; 10,000; 5,000; or 2,000 nucleotides. In addition, the nucleic acid from the double stranded RNA expression library may contain a sequence that is less than a full length RNA sequence.

In still further embodiments of any of the above aspects of the invention, the cell is a plant cell or an animal cell. Desirably the animal cell is a vertebrate or mammalian cell, for example, a human cell. The cell may be ex vivo or in vivo. The cell may be a gamete or a somatic cell, for example, a cancer cell, a stem cell, a cell of the immune system, a neuronal cell, a muscle cell, or an adipocyte.

Transformation/transfection of the cell may occur through a variety of means including, but not limited to, lipofection, DEAE-dextran-mediated transfection, microinjection, protoplast fusion, calcium phosphate precipitation, viral or retroviral delivery, electroporation, or biolistic transformation. The RNA or RNA expression vector (DNA) may be naked RNA or DNA or local anesthetic complexed RNA or DNA (Pachuk et al., Biochim. Biophys. Acta 1468:20-30, 2000). In another embodiment, the cell is not a *C. elegans* cell. Desirably the vertebrate or mammalian cell has been cultured for only a small number of passages (e.g., less than 30 passages of a cell line that has been directly obtained from American Type Culture Collection), or are primary cells. Desirably, the vertebrate or mammalian cell is transformed with nucleic acids that are not complexed with cationic lipids.

In yet another embodiment of any of the above aspects of the invention, the cell is derived from a parent cell, and is generated by: (a) transforming a population of parent cells with a bicistronic plasmid expressing a selectable marker and a reporter gene, and comprising a loxP site; (b) selecting for a cell in which the plasmid is stably integrated; and (c) selecting for a cell in which one copy of the plasmid is stably integrated in a transcriptionally active locus. Desirably the selectable marker is G418 and the reporter gene is green fluorescent protein (GFP).

In still another embodiment of the above aspects of the invention, generation of the double stranded expression library comprises: (a) isolating RNA from a cell; (b) synthesizing cDNAs from the RNA of step (a); and (c) cloning each cDNA into a vector. Desirably cDNA synthesis is optimized and/or size selected for the generation and/or selection of cDNAs that are at least 100, 500, 600, or 1000 nucleotides in length. In other embodiments, the cDNAs are least 10, 20, 30, 40, 50, 60, 70, 80, or 90 nucleotides in length. In yet other embodiments, the number of nucleotides in the cDNAs is between 5-100 nucleotides, 15-100 nucleotides, 20-95 nucleotides, 25-90 nucleotides, 35-85 nucleotides, 45-80 nucleotides, 50-75 nucleotides, or 55-70 nucleotides, inclusive. In still other embodiments, the number of nucleotides in the cDNAs is contained in one of the following ranges: 5-15 nucleotides, 15-20 nucleotides, 20-25 nucleotides, 25-35 nucleotides, 35-45 nucleotides, 45-60 nucleotides, 60-70 nucleotides, 70-80 nucleotides, 80-90 nucleotides, or 90-100 nucleotides, inclusive. In other embodiments, the cDNAs contain less than 50,000; 10,000; 5,000; or 2,000 nucleotides. In addition, the cDNA may encode an RNA fragment that is less than full length. Desirably the vector comprises two convergent T7 promoters, two convergent SP6 promoters, or one convergent T7 promoter and one convergent SP6 promoter, a selectable marker, and/or a loxP site.

In an additional embodiment of any of the above aspects of the invention, the method is carried out under conditions that inhibit or prevent an interferon response or double stranded RNA stress response.

In a fourth aspect, the invention features a method for identifying a nucleic acid sequence that modulates the function of a cell, involving: (a) transforming a population of cells with a double stranded RNA that is derived from the cells; (b) optionally selecting for a cell in which the nucleic acid is expressed; and (c) assaying for a modulation in the function of the cell, wherein the modulation identifies a nucleic acid sequence that modulates the function of a cell, wherein the method is desirably carried out under conditions that inhibit or prevent an interferon response or double stranded RNA stress response.

In a desirable embodiment of the fourth aspect of the invention, assaying for a modulation in the function of a cell comprises measuring cell motility, apoptosis, cell growth, cell invasion, vascularization, cell cycle events, cell differentiation, cell dedifferentiation, neuronal cell regeneration, or the ability of a cell to support viral replication.

In a fifth aspect, the invention features a method for identifying a nucleic acid sequence that modulates expression of a target nucleic acid in a cell, involving: (a) transforming a population of cells with a double stranded RNA that is derived from the cells; (b) optionally selecting for a cell in which the nucleic acid is expressed; and (c) assaying for a modulation in the expression of the gene in the cell, wherein the modulation identifies a nucleic acid sequence that modulates expression of a target nucleic acid in a cell, wherein the method is desirably carried out under conditions that inhibit or prevent an interferon response or double stranded RNA stress response.

In a desirable embodiment of the fifth aspect of the invention, the target nucleic acid is assayed using DNA array technology.

In a sixth aspect, the invention features a method for identifying a nucleic acid sequence that modulates the biological activity of a target polypeptide in a cell, involving: (a) transforming a population of cells with a double stranded RNA that is derived from the cells; (b) optionally selecting for a cell in which the nucleic acid is expressed in the cell; and (c) assaying for a modulation in the biological activity of a target polypeptide in the cell, wherein the modulation identifies a nucleic acid sequence that modulates the biological activity of a target polypeptide in a cell, wherein the method is desirably carried out under conditions that inhibit or prevent an interferon response or double stranded RNA stress response.

In a seventh aspect, the invention features a method for identifying a nucleic acid sequence that modulates the function of a cell, involving: (a) transforming a population of cells with a double stranded RNA; (b) optionally selecting for a cell in which the nucleic acid is expressed; and (c) assaying for a modulation in the function of the cell. Desirably, the modulation identifies a nucleic acid sequence that modulates the function of a cell, wherein the method is desirably carried out under conditions that or prevent an interferon response or double stranded RNA stress response.

In a desirable embodiment of the seventh aspect of the invention, assaying for a modulation in the function of a cell comprises measuring cell motility, apoptosis, cell growth, cell invasion, vascularization, cell cycle events, cell differentiation, cell dedifferentiation, neuronal cell regeneration, or the ability of a cell to support viral replication.

In a eighth aspect, the invention features a method for identifying a nucleic acid sequence that modulates expression of a target nucleic acid in a cell, involving: (a) transforming a population of cells with a double stranded RNA; (b) optionally selecting for a cell in which the nucleic acid is expressed; and (c) assaying for a modulation in the expression of the gene in the cell, wherein the modulation identifies a nucleic acid sequence that modulates expression of a target nucleic acid in a cell. Desirably, the method is carried out under conditions that inhibit or prevent an interferon response or double stranded RNA stress response.

In a desirable embodiment of the eighth aspect of the invention, the target nucleic acid is assayed using DNA array technology.

In a ninth aspect, the invention features a method for identifying a nucleic acid sequence that modulates the biological activity of a target polypeptide in a cell, involving: (a) transforming a population of cells with a double stranded RNA; (b) optionally selecting for a cell in which the nucleic acid is expressed in the cell; and (c) assaying for a modulation in the biological activity of a target polypeptide in the cell, wherein the modulation identifies a nucleic acid sequence that modulates the biological activity of a target polypeptide in a cell. Desirably, the method is carried out under conditions that inhibit or prevent an interferon response double stranded RNA stress response.

In one embodiment of any of the above aspects of the invention, in step (a) at least 2, more desirably 50; 100; 500; 1000; 10,000; or 50,000 cells of the population of cells are each transformed with a different double stranded RNA from a double stranded RNA expression library. Desirably, at most one double stranded RNA is inserted into each cell. In other embodiments, the population of cells is transformed with at least 5%, more desirably at least 25%, 50%, 75%, or 90%, and most desirably, at least 95% of the double stranded RNA expression library. In still another embodiment of any of the fourth, fifth, or sixth aspects of the invention, the method further involves: (d) identifying the nucleic acid sequence by amplifying and cloning the sequence. Desirably amplification of the sequence involves the use of the polymerase chain reaction (PCR).

In a tenth aspect, the invention features a cell or a population of cells that expresses a double stranded RNA that (i) modulates a function of the cell, (ii) modulates the expression of a target nucleic acid (e.g., an endogenous or pathogen gene) in the cell, and/or (iii) modulates the biological activity of a target protein (e.g., an endogenous or pathogen protein) in the cell. Desirably, the cell contains only one molecular species of double stranded RNA or only one copy of a double stranded RNA expression vector (e.g., a stably integrated vector). Desirably, the cell or population of cells is produced using one or more methods of the invention. In other embodiments, the double stranded RNA is expressed under conditions that inhibit or prevent an interferon response or a double stranded RNA stress response.

In other embodiments of any of the fourth, fifth, sixth, seventh, eighth, ninth, or tenth aspects of the invention, the double stranded RNA is derived from cDNAs or randomized nucleic acids. In addition, the double stranded RNA may be a cytoplasmic double stranded RNA, in which case the double stranded nucleic acid is made in the cytoplasm. The double stranded RNA may be made in vitro or in vivo. In addition, the identified nucleic acid sequence may be located in the cytoplasm of the cell.

In still another embodiment of any of the fourth, fifth, sixth, seventh, eighth, ninth, or tenth aspects of the invention, the nucleic acid is contained in a vector, for example, a double stranded RNA expression vector that is capable of forming a double stranded RNA. Desirably the double stranded RNA expression vector comprises at least one promoter. The promoter may be a T7 promoter, in which case, the cell further comprises T7 polymerase. Alternatively, the promoter may be an SP6 promoter, in which case, the cell further comprises SP6 polymerase. The promoter may also be one convergent T7 promoter and one convergent SP6 promoter. A cell may be made to contain T7 or SP6 polymerase by transforming the cell with a T7 polymerase or an SP6 polymerase expression plasmid, respectively. The vector may also comprise a selectable marker, for example hygromycin.

Desirably in a vector for use in any of the fourth, fifth, sixth, seventh, eighth, ninth, or tenth aspects of the invention, the sense strand and the antisense strand of the nucleic acid sequence are transcribed from the same nucleic acid sequence using two convergent promoters. In another desirable embodiment, in a vector for use in any of the above aspects of the invention, the nucleic acid sequence comprises an inverted repeat, such that upon transcription, the nucleic acid forms a double stranded RNA.

In yet another embodiment of any of the fourth, fifth, sixth, seventh, eighth, ninth, or tenth aspects of the invention, the double stranded RNA is at least 100, 500, 600, or 1000 nucleotides in length. In other embodiments of any of the fourth, fifth, or sixth aspects of the invention, the double stranded RNA is at least 10, 20, 30, 40, 50, 60, 70, 80, or 90 nucleotides in length. In yet other embodiments, the number of nucleotides in the double stranded RNA is between 5-100 nucleotides, 15-100 nucleotides, 20-95 nucleotides, 25-90 nucleotides, 35-85 nucleotides, 45-80 nucleotides, 50-75 nucleotides, or 55-70 nucleotides, inclusive. In still other embodiments, the number of nucleotides in the double stranded RNA is contained in one of the following ranges: 5-15 nucleotides, 15-20 nucleotides, 20-25 nucleotides, 25-35 nucleotides, 35-45 nucleotides, 45-60 nucleotides, 60-70 nucleotides, 70-80 nucleotides, 80-90 nucleotides, or 90-100 nucleotides, inclusive. In other embodiments, the double stranded RNA contains less than 50,000; 10,000; 5,000; or 2,000 nucleotides. In addition, the double stranded RNA may contain a sequence that is less than a full length RNA sequence.

In still further embodiments of any of the fourth, fifth, sixth, seventh, eighth, ninth, or tenth aspects of the invention, the cell is a plant cell or an animal cell. Desirably the animal cell is a vertebrate or mammalian cell, for example, a human cell. The cell may be ex vivo or in vivo. The cell may be a gamete or a somatic cell, for example, a cancer cell, a stem cell, a cell of the immune system, a neuronal cell, a muscle cell, or an adipocyte.

In other embodiments of any of the first, second, third, seventh, eighth, ninth, or tenth aspects of the invention, the double stranded RNA is derived from a cell or a population of cells and used to transform another cell population of either the same cell type or a different cell type. In desirable embodiments, the transformed cell population contains cells of a cell type that is related to the cell type of the cells from which the double stranded RNA was derived (e.g., the transformation of cells of one neuronal cell type with the double stranded RNA derived from cells of another neuronal cell type). In yet other embodiments of any of these aspects, the double stranded RNA contains one or more contiguous or non-contiguous positions that are randomized (e.g., by chemical or enzymatic synthesis using a mixture of nucleotides that may be added at the randomized position). In still other embodiments, the double stranded RNA is a randomized nucleic acid in which segments of ribonucleotides and/or deoxyribonucleotides are ligated to form the double stranded RNA.

In other embodiments of any of various aspects of the invention, the double stranded RNA specifically hybridizes to a target nucleic acid but does not substantially hybridize to non-target molecules, which include other nucleic acids in the cell or biological sample having a sequence that is less than 99, 95, 90, 80, or 70% identical or complementary to that of the target nucleic acid. Desirably, the amount of the these non-target molecules hybridized to, or associated with, the double stranded RNA, as measured using standard assays, is 2-fold, desirably 5-fold, more desirably 10-fold, and most desirably 50-fold lower than the amount of the target nucleic acid hybridized to, or associated with, the double stranded RNA. In other embodiments, the amount of a target nucleic acid hybridized to, or associated with, the double stranded RNA, as measured using standard assays, is 2-fold, desirably 5-fold, more desirably 10-fold, and most desirably 50-fold greater than the amount of a control nucleic acid hybridized to, or associated with, the double stranded RNA. Desirably, the double stranded RNA only hybridizes to one target nucleic acid from a cell under denaturing, high stringency hybridization conditions. In certain embodiments, the double stranded RNA is substantially homologous (e.g., at least 80, 90, 95, 98, or 100% homologous) to only one target nucleic acid from a cell. In other embodiments, the double stranded RNA is homologous to multiple RNAs, such as RNAs from the same gene family. In yet other embodiments, the double stranded RNA is homologous to distinctly different mRNA sequences from genes that are similarly regulated (e.g., developmental, chromatin remodeling, or stress response induced). In other embodiments, the double stranded RNA is homologous to a large number of RNA molecules, such as a double stranded RNA designed to induce a stress response or apoptosis. In other embodiments, the percent decrease in the expression of a target nucleic acid is at least 2, 5, 10, 20, or 50 fold greater than the percent decrease in the expression of a non-target or control nucleic acid. Desirably, the double stranded RNA inhibits the expression of a target nucleic acid but has negligible, if any, effect on the expression of other nucleic acids in the cell. Examples of control nucleic acids include nucleic acids with a random sequence or nucleic acids known to have little, if any, affinity for the double stranded RNA.

In other embodiments of any of various aspects of the invention, at most one molecular species of double stranded RNA is inserted into each cell. In other embodiments, at most one vector is stably integrated into the genome of each cell. In various embodiments, the double stranded RNA is active in the nucleus of the transformed cell and/or is active in the cytoplasm of the transformed cell. In various embodiments, at least 1, 10, 20, 50, 100, 500, or 1000 cells or all of the cells in the population are selected as cells that contain or express a double stranded RNA. In some embodiments, at least 1, 10, 20, 50, 100, 500, or 1000 cells or all of the cells in the population are assayed for a modulation in the function of the cell, a modulation in the expression of a target nucleic acid (e.g., an endogenous or pathogen gene) in the cell, and/or a modulation in the biological activity of a target protein (e.g., an endogenous or pathogen protein) in the cell.

In other embodiments, the double stranded RNA or double stranded RNA expression vector is complexed with one or more cationic lipids or cationic amphiphiles, such as the compositions disclosed in U.S. Pat. No. 4,897,355 (Eppstein et al., filed Oct. 29, 1987), U.S. Pat. No. 5,264,618 (Felgner et al., filed Apr. 16, 1991) or U.S. Pat. No. 5,459,127 (Felgner et al., filed Sep. 16, 1993). In other embodiments, the double stranded RNA or double stranded RNA expression vector is complexed with a liposomes/liposomic composition that includes a cationic lipid and optionally includes another component such as a neutral lipid (see, for example, U.S. Pat. No. 5,279,833 (Rose), U.S. Pat. No. 5,283,185 (Epand), and U.S. Pat. No. 5,932,241). In yet other embodiments, the double stranded RNA or double stranded RNA expression vector is complexed with any other composition that is devised by one of ordinary skill in the fields of pharmaceutics and molecular biology.

Desirably, the double stranded RNA specifically hybridizes to a target nucleic acid but does not substantially hybridize to non-target molecules, which include other nucleic acids in the cell or biological sample having a sequence that is less than 99, 95, 90, 80, or 70% identical to or complementary to that of the target nucleic acid. In other embodiments, the percent decrease in the expression of a target nucleic acid is at least 2, 5, 10, 20, or 50 fold greater than the percent decrease in the expression of a non-target or control nucleic acid. Desirably, the double stranded RNA inhibits the expression of the target nucleic acid but has negligible, if any, effect on the expression of other nucleic acids in the cell.

Transformation/transfection of the cell may occur through a variety of means including, but not limited to, lipofection, DEAE-dextran-mediated transfection, microinjection, protoplast fusion, calcium phosphate precipitation, viral or retroviral delivery, electroporation, or biolistic transformation. The RNA or RNA expression vector (DNA) may be naked RNA or DNA or local anesthetic complexed RNA or DNA (Pachuk et al., supra). In yet another embodiment, the cell is not a C. elegans cell. Desirably the vertebrate or mammalian cell has been cultured for only a small number of passages (e.g., less than 30 passages of a cell line that has been directly obtained from American Type Culture Collection), or are primary cells. In addition, desirably the vertebrate or mammalian cell is transformed with double stranded RNA that is not complexed with cationic lipids.

The transcription systems described herein provide advantages to other double stranded expression systems. Following transformation of the double stranded RNA library, cells contain hundreds to thousands of double stranded RNA expression cassettes, with concomitant expression of that many expression cassettes. In the double stranded RNA expression system of the present invention, double stranded RNA (dsRNA) expression cassettes contained within the expression vector integrate into the chromosome of the transfected cell. Desirably, every transformed cell integrates one of the double stranded expression cassettes. Through expansion of the transformed cell, episomal (non-integrated) expression vectors are diluted out of the cell over time. Desirably no transcription occurs until the episomal expression vectors are diluted out of the cell, such that not more than 5 episomal vectors remain in the cell. Most desirably, no transcription occurs until all of the episomal vectors have been diluted out of the cell, and only the integrated expression cassette remains. The time it takes for all episomal vectors to be removed from the cell is proportional to the replication rate of the transformed cell, and is generally on the order of two to several weeks of cell culture and growth. The numbers of copies of a dsRNA molecule in a transformed cell can be determined using, for example, standard PCR techniques, and thereby, the number of episomal vectors in a given cell can be monitored.

Once a stable integrant containing five or fewer, and desirably no episomal expression vectors, transcription is induced, allowing dsRNA to be expressed in the cells. This method ensures that, if desired, only one species or not more than about five species of dsRNA is expressed per cell, as opposed to other methods that express hundreds to thousands of double stranded species.

Another problem that can occur in other double stranded expression systems or dsRNA delivery systems is that some dsRNA sequences, possibly in certain cell types and through certain delivery methods, may result in an interferon response (Jaramillo et al., Cancer Invest. 13:327-338, 1995). During the induction of post-transcriptional gene silencing events, induction of an interferon response is not desired, as this could lead to cell death and possibly to the prevention of gene silencing. An additional advantage of the present invention is that the dsRNA delivery methods described herein are performed such that an interferon response is inhibited or prevented.

One of the components of an interferon response is the induction of the interferon-induced protein kinase PKR (Jaramillo et al., supra). Suppression of the interferon response and/or the PKR response, using techniques described herein, is desired in the cells targeted for a PTGS event in those instances where an interferon response would otherwise be induced. Methods for suppressing an interferon response or dsRNA stress response can be used in combination with any of the methods for identifying a nucleic acid sequence that modulates the function of a cell, gene expression in a cell, or the biological activity of a target polypeptide.

The methods of the present invention provide a means for high throughput identification of nucleic acid sequences involved in modulating the function of a cell, the expression of a target nucleic acid in a cell, or the biological activity of a target polypeptide in a cell. By transforming a population of cells with a double stranded RNA expression library, the effects of many PTGS events on cell function, expression of a target nucleic acid in a cell, or the biological activity of a target polypeptide in a cell can be evaluated simultaneously, thereby allowing for rapid identification of the nucleic acid sequence involved in a cell function, target nucleic acid expression, or biological activity of a target polypeptide of interest.

By "nucleic acid," "nucleic acid sequence," "double stranded RNA nucleic acid sequence," or "double stranded RNA nucleic acid" is meant a nucleic acid or a portion thereof that is free of the genes that, in the naturally-occurring genome of the organism from which the nucleic acid sequence of the invention is derived, flank the gene. The term therefore includes, for example, a recombinant DNA, with or without 5' or 3' flanking sequences that is incorporated into a vector, for example, a double stranded RNA expression vector; into an autonomously replicating plasmid or virus; or into the genomic DNA of a prokaryote or eukaryote; or which exists as a separate molecule (e.g., a cDNA or a genomic or cDNA fragment produced by PCR or restriction endonuclease digestion) independent of other sequences.

By "double stranded RNA" is meant a nucleic acid containing a region of two or more nucleotides that are in a double stranded conformation. In various embodiments, the double stranded RNA consists entirely of ribonucleotides or consists of a mixture of ribonucleotides and deoxynucleotides, such as the RNA/DNA hybrids disclosed, for example, by WO 00/63364, filed Apr. 19, 2000 or U.S. S. No. 60/130,377, filed Apr. 21, 1999. The double stranded RNA may be a single molecule with a region of self-complimentarity such that nucleotides in one segment of the molecule base pair with nucleotides in another segment of the molecule. In various embodiments, a double stranded RNA that consists of a single molecule consists entirely of ribonucleotides or includes a region of ribonucleotides that is complimentary to a region of deoxyribonucleotides. Alternatively, the double stranded RNA may include two different strands that have a region of complimentarity to each other. In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. Desirably, the regions of complimentarity are at least 70, 80, 90, 95, 98, or 100% complimentary. Desirably, the region of the double stranded RNA that is present in a double stranded conformation includes at least 5, 10, 20, 30, 50, 75, 100, 200, 500, 1000, 2000 or 5000 nucleotides or includes all of the nucleotides in a cDNA being represented in the double stranded RNA. In some embodiments, the double stranded RNA does not contain any single stranded regions, such as single stranded ends, or the double stranded RNA is a hairpin. Desirable RNA/DNA hybrids include a DNA strand or region that is an antisense strand or region (e.g, has at least 70, 80, 90, 95, 98, or 100% complimentary to a target nucleic acid) and an RNA strand or region that is an sense strand or region (e.g, has at least 70, 80, 90, 95, 98, or 100% identity to a target nucleic acid). In various embodiments, the RNA/DNA hybrid is made in vitro using enzymatic or chemical synthetic methods such as those described herein or those described in WO 00/63364, filed Apr. 19, 2000 or U.S. S. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the double stranded RNA is a single circular nucleic acid containing a sense and an antisense region, or the double stranded RNA includes a circular nucleic acid and either a second circular nucleic acid or a linear nucleic acid (see, for example, WO 00/63364, filed Apr. 19, 2000 or U.S. S. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the double stranded RNA includes one or more modified nucleotides in which the 2' position in the sugar contains a halogen (such as flourine group) or contains an alkoxy group (such as a methoxy group) which increases the half-life of the double stranded RNA in vitro or in vivo compared to the corresponding double stranded RNA in which the corresponding 2' position contains a hydrogen or an hydroxyl group. In yet other embodiments, the double stranded RNA includes one or more linkages between adjacent nucleotides other than a naturally-occurring phosphodiester linkage. Examples of such linkages include phosphoramide, phosphorothioate, and phosphorodithioate linkages. In other embodiments, the double stranded RNA contains one or two capped strands, as disclosed, for example, by WO 00/63364, filed Apr. 19, 2000 or U.S. S. No. 60/130,377, filed Apr. 21, 1999. In other embodiments, the double stranded RNA contains coding sequence or non-coding sequence, for example, a regulatory sequence (e.g., a transcription factor binding site, a promoter, or a 5' or 3' untranslated region (UTR) of an mRNA). Additionally, the double stranded RNA can be any of the at least partially double-stranded RNA molecules disclosed in WO 00/63364, filed Apr. 19, 2000 (see, for example, pages 8-22). Any of the double stranded RNAs may be expressed in vitro or in vivo using the methods described herein or standard methods, such as those described in WO 00/63364, filed Apr. 19, 2000 (see, for example, pages 16-22).

By "double stranded RNA expression library" or "dsRNA expression library" is meant a collection of nucleic acid expression vectors containing nucleic acid sequences, for example, cDNA sequences or randomized nucleic acid sequences that are capable of forming a double stranded RNA (dsRNA) upon expression of the nucleic acid sequence. Desirably the double stranded RNA expression library contains at least 10,000 unique nucleic acid sequences, more desirably at least 50,000; 100,000; or 500,000 unique nucleic acid sequences, and most desirably, at least 1,000,000 unique nucleic acid sequences. By a "unique nucleic acid sequence" is meant that a nucleic acid sequence of a double stranded RNA expression library has desirably less than 50%, more desirably less than 25% or 20%, and most desirably less than 10% nucleic acid identity to another nucleic acid sequence of a double stranded RNA expression library when the full length sequence are compared. Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications.

The preparation of cDNAs for the generation of double stranded RNA expression libraries is described herein. A randomized nucleic acid library may also be generated as described in detail below. The double stranded RNA expression library may contain nucleic acid sequences that are transcribed in the nucleus or that are transcribed in the cytoplasm of the cell. A double stranded RNA expression library may be generated using techniques described herein.

By "target nucleic acid" is meant a nucleic acid sequence whose expression is modulated as a result of post-transcriptional gene silencing. As used herein, the target nucleic acid may be in the cell in which the PTGS event occurs or it may be in a neighboring cell, or in a cell contacted with media or other extracellular fluid in which the cell that has undergone the PTGS event is contained. Exemplary target nucleic acids include nucleic acids associated with cancer or abnormal cell growth, such as oncogenes, and nucleic acids associated with an autosomal dominant or recessive disorder. Desirably, the double stranded RNA inhibits the expression of an allele of a nucleic acid that has a mutation associated with a dominant disorder and does not substantially inhibit the other allele of the nucleic acid (e.g, an allele without a mutation associated with the disorder). Other exemplary target nucleic acids include host cellular nucleic acids or pathogen nucleic acids required for the infection or propagation of a pathogen, such as a virus, bacteria, yeast, protozoa, or parasite.

By "target polypeptide" is meant a polypeptide whose biological activity is modulated as a result of post-transcriptional gene silencing. As used herein, the target polypeptide may be in the cell in which the PTGS event occurs or it may be in a neighboring cell, or in a cell contacted with media or other extracellular fluid in which the cell that has undergone the PTGS event is contained.

As used herein, by "randomized nucleic acids" is meant nucleic acids, for example, those that are at least 100, 500, 600, or 1000 nucleotides in length, constructed from RNA isolated from a particular cell type. In other embodiments, the nucleic acids are at least 10, 20, 30, 40, 50, 60, 70, 80, or 90 nucleotides in length. In yet other embodiments, the number of nucleotides in the nucleic acids is between 5-100 nucleotides, 15-100 nucleotides, 20-95 nucleotides, 25-90 nucleotides, 35-85 nucleotides, 45-80 nucleotides, 50-75 nucleotides, or 55-70 nucleotides, inclusive. In still other embodiments, the number of nucleotides in the nucleic acids is contained in one of the following ranges: 5-15 nucleotides, 15-20 nucleotides, 20-25 nucleotides, 25-35 nucleotides, 35-45 nucleotides, 45-60 nucleotides, 60-70 nucleotides, 70-80 nucleotides, 80-90 nucleotides, or 90-100 nucleotides, inclusive. In other embodiments, the nucleic acids contain less than 50,000; 10,000; 5,000; or 2,000 nucleotides. A randomized nucleic acid library may be constructed in a number of ways. For example, it may be constructed from existing cDNA libraries. In one example, the cDNA libraries are shuffled using the "Gene Shuffling" technology of Maxygen Corp. The cDNA sequences are amplified using inefficient PCR either by restricting elongation time or through the use of manganese. A library of recombinants is created, and the library is finally amplified by PCR and cloned into vectors. In a second method, existing cDNA libraries are digested with an endonuclease to generate fragments of 10 to 300 base pairs. Alternatively, the cDNA libraries are digested to generate shorter fragments of, for example, 5 to 50 base pairs, 5 to 40 base pairs, 5 to 20 base pairs, 5 to 10 base pairs, or 10 to 20 base pairs, inclusive. If the fragments are to contain 5' OH and 3' $PO_4$ groups, they are dephosphorylated using alkaline phosphatase and phosphorylated using polynucleotide kinase. These dsDNA fragments are then ligated to form larger molecules, and are size selected. In a third example, randomized nucleic acid libraries are created by using random priming of cDNA libraries (using random hexamers and Klenow) to generate short fragments of 20 to 100 nucleotides. Alternatively, shorter fragments are generated that contain, for example, 5 to 50 nucleotides, 5 to 40 nucleotides, 5 to 20 nucleotides, 5 to 10 nucleotides, or 10 to 20 nucleotides, inclusive. These fragments are then ligated randomly to give a desired sized larger fragment.

Alternatively, a randomized nucleic acid library can be generated from random sequences of oligonucleotides. For example, DNA or RNA oligonucleotides may be prepared chemically. Random DNA sequences may also be prepared enzymatically using terminal transferase in the presence of all dNTPs. Random RNA molecules may be prepared using NDPs and NDP phosphorylase. The random sequences may be 10 to 300 bases in length. Alternatively, shorter random sequences are used that contain, for example, 5 to 50 bases, 5 to 40 bases, 5 to 20 bases, 5 to 10 bases, or 10 to 20 bases, inclusive. The sequences are ligated to form the desired larger sequence using RNA ligase. Alternatively these sequences may be ligated chemically. The oligonucleotides are phosphorylated at the 5' position using polynucleotide kinase or by chemical methods, prior to ligation enzymatically. Chemical ligations can utilize a 5' $PO_4$ and a 3'OH group or a 5' OH and a 3' $PO_4$ group.

Alternatively, a randomized nucleic acid library can be generated by converting the random DNA sequences into dsDNA sequences using DNA polymerase (Klenow), dNTP and random heteromeric primers, and the RNA sequences are converted into dsDNA sequences by reverse transcriptase and Klenow. After converting into DNA (ss or ds) the sequences are then amplified by PCR. The dsDNA fragments can also be ligated to give larger fragments of a desired size.

The randomized nucleic acids may be cloned into a vector, for example, an expression vector, as a double stranded RNA transcription cassette. The sequence of the nucleic acid may not be known at the time the vector is generated. The randomized nucleic acid may contain coding sequence or non-coding sequence, for example, a regulatory sequence (e.g., a transcription factor binding site, a promoter, or a 5' or 3' untranslated region (UTR) of an mRNA).

By "Cre-mediated double recombination" is meant two nucleic acid recombination events involving loxP sites that are mediated by Cre recombinase. A Cre-mediated double recombination event can occur, for example, as illustrated in FIG. 1.

By "function of a cell" is meant any cell activity that can be measured or assessed. Examples of cell function include, but are not limited to, cell motility, apoptosis, cell growth, cell invasion, vascularization, cell cycle events, cell differentiation, cell dedifferentiation, neuronal cell regeneration, and the ability of a cell to support viral replication. The function of a cell may also be to affect the function, gene expression, or the polypeptide biological activity of another cell, for example, a neighboring cell, a cell that is contacted with the cell, or a cell that is contacted with media or other extracellular fluid that the cell is contained in.

By "apoptosis" is meant a cell death pathway wherein a dying cell displays a set of well-characterized biochemical hallmarks that include cytolemmal membrane blebbing, cell soma shrinkage, chromatin condensation, nuclear disintegration, and DNA laddering. There are many well-known assays for determining the apoptotic state of a cell, including, and not limited to: reduction of MTT tetrazolium dye, TUNEL staining, Annexin V staining, propidium iodide staining, DNA laddering, PARP cleavage, caspase activation, and assessment of cellular and nuclear morphology. Any of these or other known assays may be used in the methods of the invention to determine whether a cell is undergoing apoptosis.

By "polypeptide biological activity" is meant the ability of a target polypeptide to modulate cell function. The level of polypeptide biological activity may be directly measured using standard assays known in the art. For example, the relative level of polypeptide biological activity may be assessed by measuring the level of the mRNA that encodes the target polypeptide (e.g., by reverse transcription-polymerase chain reaction (RT-PCR) amplification or Northern blot analysis); the level of target polypeptide (e.g., by ELISA or Western blot analysis); the activity of a reporter gene under the transcriptional regulation of a target polypeptide transcriptional regulatory region (e.g., by reporter gene assay, as described below); the specific interaction of a target polypeptide with another molecule, for example, a polypeptide that is activated by the target polypeptide or that inhibits the target polypeptide activity (e.g., by the two-hybrid assay); or the phosphorylation or glycosylation state of the target polypeptide. A compound, such as a dsRNA, that increases the level of the target polypeptide, mRNA encoding the target polypeptide, or reporter gene activity within a cell, a cell extract, or other experimental sample is a compound that stimulates or increases the biological activity of a target polypeptide. A compound, such as a dsRNA, that decreases the level of the target polypeptide, mRNA encoding the target polypeptide, or reporter gene activity within a cell, a cell extract, or other experimental sample is a compound that decreases the biological activity of a target polypeptide.

By "assaying" is meant analyzing the effect of a treatment, be it chemical or physical, administered to whole animals, cells, tissues, or molecules derived therefrom. The material being analyzed may be an animal, a cell, a tissue, a lysate or extract derived from a cell, or a molecule derived from a cell. The analysis may be, for example, for the purpose of detecting altered cell function, altered gene expression, altered endogenous RNA stability, altered polypeptide stability, altered polypeptide levels, or altered polypeptide biological activity. The means for analyzing may include, for example, antibody labeling, immunoprecipitation, phosphorylation assays, glycosylation assays, and methods known to those skilled in the art for detecting nucleic acids. In some embodiments, assaying is conducted under selective conditions.

By "modulates" is meant changing, either by a decrease or an increase. As used herein, desirably a nucleic acid sequence decreases the function of a cell, the expression of a target nucleic acid in a cell, or the biological activity of a target polypeptide in a cell by least 20%, more desirably by at least 30%, 40%, 50%, 60% or 75%, and most desirably by at least 90%. Also as used herein, desirably a nucleic acid sequence increases the function of a cell, the expression of a target nucleic acid in a cell, or the biological activity of a target polypeptide in a cell by at least 1.5-fold to 2-fold, more desirably by at least 3-fold, and most desirably by at least 5-fold.

By "a decrease" is meant a lowering in the level of: a) protein (e.g., as measured by ELISA or Western blot analysis); b) reporter gene activity (e.g., as measured by reporter gene assay, for example, β-galactosidase, green fluorescent protein, or luciferase activity); c) mRNA (e.g., as measured by RT-PCR or Northern blot analysis relative to an internal control, such as a "housekeeping" gene product, for example, β-actin or glyceraldehyde 3-phosphate dehydrogenase (GAPDH)); or d) cell function, for example, as assayed by the number of apoptotic, mobile, growing, cell cycle arrested, invasive, differentiated, or dedifferentiated cells in a test sample. In all cases, the lowering is desirably by at least 20%, more desirably by at least 30%, 40%, 50%, 60%, 75%, and most desirably by at least 90%. As used herein, a decrease may be the direct or indirect result of PTGS.

By "an increase" is meant a rise in the level of: a) protein (e.g., as measured by ELISA or Western blot analysis); b) reporter gene activity (e.g., as measured by reporter gene assay, for example, β-galactosidase, green fluorescent protein, or luciferase activity); c) mRNA (e.g., as measured by RT-PCR or Northern blot analysis relative to an internal control, such as a "housekeeping" gene product, for example, β-actin or glyceraldehyde 3-phosphate dehydrogenase (GAPDH)); or d) cell function, for example, as assayed by the number of apoptotic, mobile, growing, cell cycle arrested, invasive, differentiated, or dedifferentiated cells in a test sample. Desirably, the increase is by at least 1.5-fold to 2-fold, more desirably by at least 3-fold, and most desirably by at least 5-fold. As used herein, an increase may be the indirect result of PTGS. For example, the double stranded RNA may inhibit the expression of a protein, such as a suppressor protein, that would otherwise inhibit the expression of another nucleic acid.

By "alteration in the level of gene expression" is meant a change in transcription, translation, or mRNA or protein stability such that the overall amount of a product of the gene, i.e., mRNA or polypeptide, is increased or decreased.

By "reporter gene" is meant any gene that encodes a product whose expression is detectable and/or able to be quantitated by immunological, chemical, biochemical, or biological assays. A reporter gene product may, for example, have one of the following attributes, without restriction: fluorescence (e.g., green fluorescent protein), enzymatic activity (e.g., β-galactosidase, luciferase, chloramphenicol acetyltransferase), toxicity (e.g., ricin A), or an ability to be specifically bound by an additional molecule (e.g., an unlabeled antibody, followed by a labelled secondary antibody, or biotin, or a detectably labelled antibody). It is understood that any engineered variants of reporter genes that are readily available to one skilled in the art, are also included, without restriction, in the foregoing definition.

By "protein" or "polypeptide" or "polypeptide fragment" is meant any chain of more than two amino acids, regardless of post-translational modification (e.g., glycosylation or phosphorylation), constituting all or part of a naturally occurring polypeptide or peptide, or constituting a non-naturally occurring polypeptide or peptide.

By "promoter" is meant a minimal sequence sufficient to direct transcription of a gene. Also included in this definition are those transcription control elements (e.g., enhancers) that are sufficient to render promoter-dependent gene expression controllable in a cell type-specific, tissue-specific, or temporal-specific manner, or that are inducible by external signals or agents; such elements, which are well-known to skilled artisans, may be found in a 5' or 3' region of a gene or within an intron. Desirably a promoter is operably linked to a nucleic acid sequence, for example, a cDNA or a gene in such a way as to permit expression of the nucleic acid sequence.

By "operably linked" is meant that a gene and one or more transcriptional regulatory sequences, e.g., a promoter or enhancer, are connected in such a way as to permit gene expression when the appropriate molecules (e.g., transcriptional activator proteins) are bound to the regulatory sequences.

By "expression vector" is meant a DNA construct that contains at least one promoter operably linked to a downstream gene or coding region (e.g., a cDNA or genomic DNA fragment that encodes a protein, optionally, operatively linked to sequence lying outside a coding region, an antisense RNA coding region, or RNA sequences lying outside a coding region). Transfection or transformation of the expression vector into a recipient cell allows the cell to express RNA encoded by the expression vector. An expression vector may be a genetically engineered plasmid, virus, or artificial chromosome derived from, for example, a bacteriophage, adenovirus, retrovirus, poxvirus, or herpesvirus.

By "transformation" or "transfection" is meant any method for introducing foreign molecules into a cell (e.g., a bacterial, yeast, fungal, algal, plant, insect, or animal cell, particularly a vertebrate or mammalian cell). The cell may be in an animal. Lipofection, DEAE-dextran-mediated transfection, microinjection, protoplast fusion, calcium phosphate precipitation, viral or retroviral delivery electroporation, and biolistic transformation are just a few of the transformation/transfection methods known to those skilled in the art. The RNA or RNA expression vector (DNA) may be naked RNA or DNA or local anesthetic complexed RNA or DNA (Pachuk et al, supra). Other standard transformation/transfection methods and other RNA and/or DNA delivery agents (e.g., a cationic lipid, liposome, or bupivacaine) are described in WO 00/63364, filed Apr. 19, 2000 (see, for example, pages 18-26). Commercially available kits can also be used to deliver RNA or DNA to a cell. For example, the Transmessenger Kit from Qiagen, an RNA kit from Xeragon Inc., and an RNA kit from DNA Engine Inc. (Seattle, Wash.) can be used to introduce single or double stranded RNA into a cell.

By "transformed cell" or "transfected cell" is meant a cell (or a descendent of a cell) into which a nucleic acid molecule, for example, a double stranded RNA or double stranded expression vector has been introduced, by means of recombinant nucleic acid techniques. Such cells may be either stably or transiently transfected.

By "selective conditions" is meant conditions under which a specific cell or group of cells can be selected for. For example, the parameters of a fluorescence-activated cell sorter (FACS) can be modulated to identify a specific cell or group of cells. Cell panning, a technique known to those skilled in the art, is another method that employs selective conditions.

As use herein, by "optimized" is meant that a nucleic acid fragment is generated through inefficient first strand synthesis (e.g., reverse transcription (RT) and/or RT/second strand synthesis (RT-SSS) using Klenow or other enzymes and/or RT-PCR or PCR, to be of a particular length. Desirably the length of the nucleic acid fragment is less than a full length cDNA or is 100, 500, 600, or 1000 nucleotides in length. In other embodiments, the nucleic acid fragment is at least 10, 20, 30, 40, 50, 60, 70, 80, or 90 nucleotides in length. In yet other embodiments, the number of nucleotides in the nucleic acid fragment is between 5-100 nucleotides, 15-100 nucleotides, 20-95 nucleotides, 25-90 nucleotides, 35-85 nucleotides, 45-80 nucleotides, 50-75 nucleotides, or 55-70 nucleotides, inclusive. In still other embodiments, the number of nucleotides in the nucleic acid fragment is contained in one of the following ranges: 5-15 nucleotides, 15-20 nucleotides, 20-25 nucleotides, 25-35 nucleotides, 35-45 nucleotides, 45-60 nucleotides, 60-70 nucleotides, 70-80 nucleotides, 80-90 nucleotides, or 90-100 nucleotides, inclusive. In other embodiments, the nucleic acid fragment contains less than 50,000; 10,000; 5,000; or 2,000 nucleotides. Optimization of the length of a nucleic acid can be achieved during first strand or second strand synthesis of a desired nucleic acid by lowering $Mg^{++}$ concentrations to no less than the nucleotide concentrations; by adding $Mn^{++}$ to the reaction to achieve the desired size selection (e.g., by replacing $Mg^{++}$ completely, or by adding $Mn^{++}$ at varying concentrations along with $Mg^{++}$); by decreasing and/or limiting concentrations of dNTP(s) to effect the desired fragment size; by using various concentrations of ddNTP(s) along with standard or optimal concentrations of dNTP(s), to achieve varying ratios, to obtain the desired fragment size; by using limited and controlled exonuclease digestion of the fragment following RT, RT-SSS, RT-PCR, or PCR; or by a combination of any of these methods.

As used herein, by "sized selected" is meant that a nucleic acid of a particular size is selected for use in the construction of dsRNA expression libraries as described herein. Desirably the size selected nucleic acid is less than a full length cDNA sequence or at least 100, 500, 600, or 1000 nucleotides in length. In other embodiments, the nucleic acid is at least 10, 20, 30, 40, 50, 60, 70, 80, or 90 nucleotides in length. In yet other embodiments, the number of nucleotides in the nucleic acid is between 5-100 nucleotides, 15-100 nucleotides, 20-95 nucleotides, 25-90 nucleotides, 35-85 nucleotides, 45-80 nucleotides, 50-75 nucleotides, or 55-70 nucleotides, inclusive. In still other embodiments, the number of nucleotides in the nucleic acid is contained in one of the following ranges: 5-15 nucleotides, 15-nucleotides, 20-25 nucleotides, 25-35 nucleotides, 35-45 nucleotides, 45-60 nucleotides, 60-70 nucleotides, 70-80 nucleotides, 80-90 nucleotides, or 90-100 nucleotides, inclusive. In other embodiments, the nucleic acid contains less than 50,000; 10,000; 5,000; or 2,000 nucleotides. For example, a nucleic acid may be size selected using size exclusion chromatography (e.g., as size exclusion Sepharose matrices) according to standard procedures (see, for example, Sambrook, Fritsch, and Maniatis, *Molecular Cloning: A Laboratory Manual* (2d ed.), Cold Spring Harbor Laboratory Press, Cold Spring Harbor, N.Y., 1989).

By "under conditions that inhibit or prevent an interferon response or a dsRNA stress response" is, meant conditions that prevent or inhibit one or more interferon responses or cellular RNA stress responses involving cell toxicity, cell death, an anti-proliferative response, or a decreased ability of a dsRNA to carry out a PTGS event. These responses include, but are not limited to, interferon induction (both Type 1 and Type II), induction of one or more interferon stimulated genes, PKR activation, 2'5'-OAS activation, and any downstream cellular and/or organismal sequelae that result from the activation/induction of one or more of these responses. By "organismal sequelae" is meant any effect(s) in a whole animal, organ, or more locally (e.g., at a site of injection) caused by the stress response. Exemplary manifestations include elevated cytokine production, local inflammation, and necrosis. Desirably the conditions that inhibit these responses are such that not more than 95%, 90%, 80%, 75%, 60%, 40%, or 25%, and most desirably not more than 10% of the cells undergo cell toxicity, cell death, or a decreased ability to carry out a PTGS event, compared to a cell not exposed to such interferon response inhibiting conditions, all other conditions being equal (e.g., same cell type, same transformation with the same dsRNA expression library.

Apoptosis, interferon induction, 2'5' OAS activation/induction, PKR induction/activation, anti-proliferative responses, and cytopathic effects are all indicators for the RNA stress response pathway. Exemplary assays that can be used to measure the induction of an RNA stress response as described herein include a TUNEL assay to detect apoptotic cells, ELISA assays to detect the induction of alpha, beta and gamma interferon, ribosomal RNA fragmentation analysis to detect activation of 2'5'OAS, measurement of phosphorylated eIF2a as an indicator of PKR (protein kinase RNA inducible) activation, proliferation assays to detect changes in cellular proliferation, and microscopic analysis of cells to identify cellular cytopathic effects (see, e.g., Example 11). Desirably, the level of an interferon response or a dsRNA stress response in a cell transformed with a double stranded RNA or a double strand RNA expression vector is less than 20, 10, 5, or 2-fold greater than the corresponding level in a mock-transfected control cell under the same conditions, as measured using one of the assays described herein. In other embodiments, the level of an interferon response or a dsRNA stress response in a cell transformed with a double stranded RNA or a double strand RNA expression vector using the methods of the present invention is less than 500%, 200%, 100%, 50%, 25%, or 10% greater than the corresponding level in a corresponding transformed cell that is not exposed to such interferon response inhibiting conditions, all other conditions being equal. Desirably, the double strand RNA does not induce a global inhibition of cellular transcription or translation.

By "specifically hybridizes" is meant a double stranded RNA that hybridizes to a target nucleic acid but does not substantially hybridize to other nucleic acids in a sample (e.g., a sample from a cell) that naturally includes the target nucleic acid, when assayed under denaturing conditions. In one embodiment, the amount of a target nucleic acid hybridized to, or associated with, the double stranded RNA, as measured using standard assays, is 2-fold, desirably 5-fold, more desirably 10-fold, and most desirably 50-fold greater than the amount of a control nucleic acid hybridized to, or associated with, the double stranded RNA.

By "high stringency conditions" is meant hybridization in 2×SSC at 40° C. with a DNA probe length of at least 40 nucleotides. For other definitions of high stringency conditions, see F. Ausubel et al., *Current Protocols in Molecular Biology*, pp. 6.3.1-6.3.6, John Wiley & Sons, New York, N.Y., 1994, hereby incorporated by reference.

Conditions and techniques that can be used to prevent an interferon response or dsRNA stress response during the screening methods of the present invention are described herein.

DETAILED DESCRIPTION OF THE INVENTION

Figure 1:
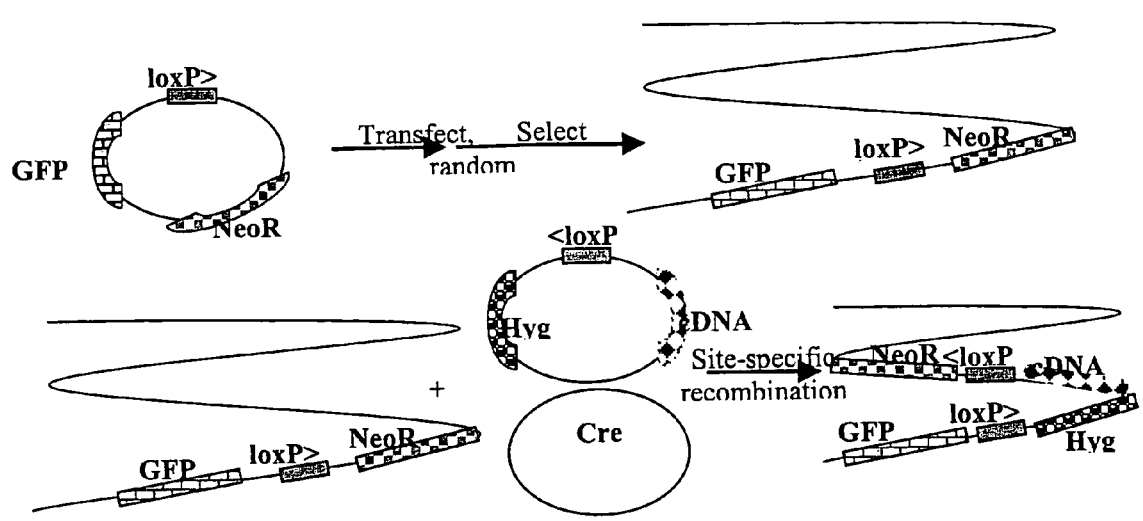
FIG. 1 is a schematic representation of a strategy to isolate clonally pure stable integrants that contain a single expression unit isolated from cells transfected with a double-stranded RNA encoding a cDNA library.

Post-transcriptional gene silencing (PTGS) can be used as a tool to identify and validate specific unknown genes involved in cell function, gene expression, and polypeptide biological activity. Although the use of PTGS as a validation strategy is well documented in invertebrates and plants, its use in identification of genes that modulate cell function, gene expression, or polypeptide biological activity, as described below, is novel. Since novel genes are likely to be identified through the methods of the present invention, PTGS is developed for use in validation and to identify novel targets for use in therapies for diseases, for example, cancer, neurological disorders, obesity, leukemia, lymphomas, and other disorders of the blood or immune system.

The present invention features methods to identify unknown targets that result in the modulation of a particular phenotype, an alteration of gene expression in a cell, or an alteration in polypeptide biological activity in a cell, using either a library based screening approach or a non-library based approach to identify nucleic acids that induce gene silencing. The present invention also allows the determination of function of a given sequence. These methods involve the direct delivery of in vitro transcribed double stranded RNA (dsRNA), as well as plasmid-based systems that direct the cell to make its own dsRNA. To avoid problems associated with transfection efficiency, plasmids are designed to contain a selectable marker to ensure the survival of only those cells that have taken up plasmid DNA. One group of plasmids directs the synthesis of dsRNA that is transcribed in the cytoplasm, while another group directs the synthesis of dsRNA that is transcribed in the nucleus.

Identification of Genes by Assaying for a Modulation in Cell Function

Functional identification of novel genes can be accomplished through the use of a number of different assays. For example, cells may be assayed for cell motility, apoptosis, cell growth, cell invasion, vascularization, cell cycle events, cell differentiation, cell dedifferentiation, neuronal cell regeneration, or the ability to support viral replication, as well as other cell functions known in the art. Methods for carrying out such functional assays are well known and are described, for example, in Platet and Garcia (Invasion Metastasis 18:198-208, 1998-1999); Harper et al. (Neuroscience 88:257-267, 1999); and Tomaselli et al. (J. Cell Biol. 105: 2347-2358, 1987), and are also described below.

Functional identification of nucleic acid sequences involved in modulating a particular cell function may be carried out by comparing cells transfected with a dsRNA to control cells that have not been transformed with a dsRNA or that have been mock-transfected, in a functional assay. A cell that has taken up sequences unrelated to a particular function will perform in the particular assay in a manner similar to the control cell. A cell experiencing PTGS of a gene involved in the particular function will exhibit an altered ability to perform in the functional assay compared to the control.

The percent modulation of a particular cell function that identifies a nucleic acid sequence that modulates the function of a cell will vary depending on the assay, phenotype, and the particular nucleic acid affected by PTGS. For each assay, the percent modulation can readily be determined by one skilled in the art, when used in conjunction with controls, as described herein. Desirably the modulation is at least 20%, more desirably at least 30%, 40%, 50%, 60%, 75%, and most desirably at least 90% compared to the control. An increase in the function of a cell can also be measured in terms of fold increase, where desirably, the increase is at least 1.5-fold to 5-fold compared to the control.

Alternatively, the function of a cell may be to affect the function, gene expression, or polypeptide biological activity of another cell, for example, a neighboring cell, a cell that is contacted with the cell in which a PTGS event occurs, or a cell that is contacted with media or other extracellular fluid that the cell in which a PTGS event occurs is contained in. For example, a cell experiencing PTGS of a gene may modulate cell motility, apoptosis, cell growth, cell invasion, vascularization, cell cycle events, cell differentiation, cell dedifferentiation, neuronal cell regeneration, or the ability to support viral replication of a nearby cell, or a cell that is exposed to media or other extracellular fluid in which the transfected cell in which a PTGS event occurs was once contained. This can be tested by removing the media in which a cell experiencing a PTGS event is occurring and placing it on a separate cell or population of cells. If the function of the separate cell or population of cells is modulated, compared to a cell or population of cells receiving media obtained from cells that had been mock transfected, then one or more of the cells experiencing a PTGS event can affect the function of another cell. The identity of the nucleic acid sequence that causes the modulation can be identified with repeated rounds of selection.

In another method, a single cell experiencing a PTGS event can be placed in proximity of a cell or a population of cells that was not transfected with dsRNA, and the effect of this placement is evaluated for a modulation in the function of the cell or population of cells. If the function of the non-transfected cell or population of cells is modulated, compared to a cell or population of cells in proximity of a cell that was mock transfected, then the cell experiencing a PTGS event contains a nucleic acid sequence that can affect the function of another cell. This nucleic acid sequence can be identified using techniques described herein.

Identification of Genes Using Differential Gene Expression

Differential gene expression analysis can be used to identify a nucleic acid sequence that modulates the expression of a target nucleic acid in a cell. Alterations in gene expression induced by gene silencing can be monitored in a cell into which a dsRNA has been introduced. For example, differential gene expression can be assayed by comparing nucleic acids expressed in cells into which dsRNA has been introduced to nucleic acids expressed in control cells that were not transfected with dsRNA or that were mock-transfected. Gene array technology can be used in order to simultaneously examine the expression levels of many different nucleic acids. Examples of methods for such expression analysis are described by Marrack et al. (Current Opinions in Immunology 12:206-209, 2000); Harkin (Oncologist 5:501-507, 2000); Pelizzari et al. (Nucleic Acids Res. 28:4577-4581, 2000); and Marx (Science 289:1670-1672, 2000).

Identification of Genes by Assaying Polypeptide Biological Activity

Novel nucleic acid sequences that modulate the biological activity of a target polypeptide can also be identified by examining polypeptide biological activity. Various polypeptide biological activities can be evaluated to identify novel genes according to the methods of the invention. For example, the expression of a target polypeptide(s) may be examined. Alternatively, the interaction between a target polypeptide(s) and another molecule(s), for example, another polypeptide or a nucleic acid may be assayed. Phosphorylation or glycosylation of a target polypeptide(s) may also be assessed, using standard methods known to those skilled in the art.

Identification of nucleic acid sequences involved in modulating the biological activity of a target polypeptide may be carried out by comparing the polypeptide biological activity of a cell transfected with a dsRNA to a control cell that has not been transfected with a dsRNA or that has been mock-transfected. A cell that has taken up sequences unrelated to a particular polypeptide biological activity will perform in the particular assay in a manner similar to the control cell. A cell experiencing PTGS of a gene involved in the particular polypeptide biological activity will exhibit an altered ability to perform in the biological assay, compared to the control.

Insertion of Single Units Into the Chromosome and Generation of a Cell Line Containing a Single dsRNA Expression Library Integrant The present invention involves the generation of a target cell line in which the dsRNA expression library is subsequently introduced. Through the use of site-specific recombination, single integrants of dsRNA expression cassettes are generated at the same locus of all cells in the target cell line, allowing uniform expression of the dsRNA in all of the integrants. A dsRNA expression library derived from various cell lines is used to create a representative library of stably integrated cells, each cell within the target cell line containing a single integrant. Cre/lox, Lambda-Cro repressor, and Flp recombinase systems or retroviruses are used to generate these singular integrants of dsRNA expression cassettes in the target cell line (Satoh et al., J. Virol. 74:10631-10638, 2000; Trinh et al., J. Immunol. Methods 244:185-193, 2000; Serov et al., An. Acad. Bras. Cienc. 72:389-398, 2000; Grez et al., Stem Cells. 16:235-243, 1998; Habu et al., Nucleic Acids Symp. Ser. 42:295-296, 1999; Haren et al., Annu. Rev. Microbiol. 53:245-281, 1999; Baer et al., Biochemistry 39:7041-7049, 2000; Follenzi et al., Nat. Genet. 25:217-222, 2000; Hindmarsh et al., Microbiol. Mol. Biol. Rev. 63:836-843, 1999; Darquet et al., Gene Ther. 6:209-218, 1999; Darquet et al., Gene Ther. 6:209-218, 1999; Yu et al., Gene 223:77-81, 1998; Darquet et al., Gene Ther. 4:1341-1349, 1997; and Koch et al., Gene 249:135-144, 2000). These systems are used singularly to generate singular insertion clones, and also in combination.

The following exemplary sequence specific integrative systems use short target sequences that allow targeted recombination to be achieved using specific proteins: FLP recombinase, bacteriophage Lambda integrase, HIV integrase, and pilin recombinase of Salmonella (Seng et al. Construction of a Flp "exchange cassette" contained vector and gene targeting in mouse ES cell] A book chapter PUBMED entry 11797223—Sheng Wu Gong Cheng Xue Bao. 2001 September; 17(5):566-9., Liu et al., Nat Genet. 2001 Jan. 1; 30(1):66-72., Awatramani et al., Nat Genet. 2001 November; 29(3):257-9., Heidmann and Lehner, Dev Genes Evol. 2001 September; 211(8-9):458-65, Schaft et al., Genesis. 2001 September; 31(1):6-10, Van Duyne, Annu Rev Biophys Biomol Struct. 2001; 30:87-104., Lorbach et al., J Mol. Biol. 2000 Mar. 10; 296(5):1175-81., Darquet et al., Gene Ther. 1999 February; 6(2):209-18., Bushman and Miller, J. Virol. 1997 January; 71(1):458-64., Fulks et al., J. Bacteriol. 1990 January; 172(1):310-6). A singular integrant is produced by randomly inserting the specific sequence (e.g., loxp in the cre recombinase system) and selecting or identifying the cell that contains a singular integrant that supports maximal expression. For example, integrants that show maximal expression following random integration can be identified through the use of reporter gene sequences associated with the integrated sequence. The cell can be used to specifically insert the expression cassette into the site that contains the target sequence using the specific recombinase, and possibly also remove the expression cassette that was originally placed to identify the maximally expressing chromosomal location. A skilled artisan can also produce singular integrants using retroviral vectors, which integrate randomly and singularly into the eukaryotic genome. In particular, singular integrants can be produced by inserting retroviral vectors that have been engineered to contain the desired expression cassette into a naïve cell and selecting for the chromosomal location that results in maximal expression (Michael et al., EMBO Journal, vol 20: pages 2224-2235, 2001; Reik and Murrell., Nature, vol. 405, page 408-409, 2000; Berger et al., Molecular Cell, vol. 8, pages 263-268). One may also produce a singular integrant by cotransfecting the bacterial RecA protein with or without nuclear localization signal along with sequences that are homologous to the target sequence (e.g., a target endogenous sequence or integrated transgene sequence). Alternatively, a nucleic acid sequence that encodes a RecA protein with nuclear localization signals can be cotransfected (Shibata et al., Proc Natl Acad Sci USA. 2001 Jul. 17; 98(15): 8425-32. Review., Muyrers et al., Trends Biochem Sci. 2001 May; 26(5):325-31., Paul et al., Mutat Res. 2001 Jun. 5; 486(1):11-9., Shcherbakova et al., Mutat Res. 2000 Feb. 16; 459(1):65-71., Lantsov. Mol Biol (Mosk). 1994 May-June; 28(3):485-95).

An example utilizing such methods is detailed below.

Creation of the Target Cell Line

Target cell lines are the same cell lines as the ones from which the dsRNA expression libraries will be derived. Target cells are created by transfecting the selected cell line with a bicistronic plasmid expressing a selectable marker, such as G418 and the reporter gene GFP. The plasmid also bears a loxP site. Plasmids integrate randomly into the chromosome through the process of illegitimate recombination at a frequency of $10^{-4}$. Following transfection, cells containing integrants are selected by culturing the cells in the presence of G418 at a concentration determined earlier in a kill curve analysis. About a dozen G418-resistant colonies are expanded and relative GFP expression levels are determined using flow cytometry. DNA from the cells is analyzed by Southern blot analysis to determine integrant copy number. Several single copy integrants exhibiting the highest GFP expression levels are then selected as the target cell lines. GFP expression is monitored because dsRNA encoding templates are then integrated into the loci containing the loxP, GFP, and G418 cassettes in a site-specific fashion, and it is important to ensure that these loci are transcriptionally active. Since cells are selected on the basis of G418 resistance and GFP expression, integration of the plasmid DNA can occur at the loxP site, destroying its function. Several cell lines are therefore chosen to reasonably ensure that at least one integrant has an intact loxP site.

Double Stranded RNA Expression Library Construction and Site-Specific Recombination into the Target Cell Line A cDNA library or a randomized library is constructed from RNA isolated from selected cell lines. cDNAs or randomized nucleic acids in the size range of at least 100 to 1000 nucleotides, for example, 500 to 600 nucleotides are optimized during synthesis or are size-selected prior to cloning. In other embodiments, the nucleic acids are at least 10, 20, 30, 40, 50, 60, 70, 80, or 90 nucleotides in length. In yet other embodiments, the number of nucleotides in the nucleic acids is between 5-100 nucleotides, 15-100 nucleotides, 20-95 nucleotides, 25-90 nucleotides, 35-85 nucleotides, 45-80 nucleotides, 50-75 nucleotides, or 55-70 nucleotides, inclusive. In still other embodiments, the number of nucleotides in the nucleic acids is contained in one of the following ranges: 5-15 nucleotides, 15-20 nucleotides, 20-25 nucleotides, 25-35 nucleotides, 35-45 nucleotides, 45-60 nucleotides, 60-70 nucleotides, 70-80 nucleotides, 80-90 nucleotides, or 90-100 nucleotides, inclusive. In other embodiments, the nucleic acid contains less than 50,000; 10,000; 5,000; or 2,000 nucleotides. Each cDNA or randomized nucleic acid is then cloned into a plasmid vector as a dsRNA transcription cassette flanked by two convergent promoters (such as T7 promoters as described herein). The promoters are transcriptionally regulated such that they are off until induced, for example, using a tet ON/OFF system (Forster et al., Nucleic Acids Res. 27:7708-710, 1999; Liu et al., Biotechniques 24:624-628, 6,30-632, 1998; and Gatz, Methods Cell Biol. 50:411-424, 1995). The plasmid also contains the hygromycin resistance gene and an inverted loxP site. The cDNA plasmid library or randomized plasmid library is then cotransfected into the target cell line with a plasmid expressing Cre recombinase, which catalyzes site-specific recombination of the transfected cDNA plasmid or randomized nucleic acid plasmid at the inverted loxP site into the chromosomal locus containing the GFP gene and loxP site (see FIG. 1). The use of the Cre/lox system allows the efficient integration of a plasmid into the chromosome (every transfected cell is predicted to undergo a plasmid integration event). Other site-specific recombination strategies can also be utilized. This results in having every integration to occur at the same site, thereby obviating potential problems with loci dependent expression.

Two days following transfection, cells are incubated in the presence of hygromycin to kill untransfected cells and to select for stable integrants. Transcription of dsRNA is induced, and selected cells are assayed for an alteration in cell function, the biological activity of a target polypeptide, or differential gene expression. Cells expressing dsRNA corresponding to a target nucleic acid exhibit an altered function, for example, increased or decreased cell invasion, motility, apoptosis, growth, differentiation, dedifferentiation, or regeneration, or the ability of the cell to support viral replication. Cells exhibiting altered function are then expanded and the sequence of the integrant is determined. Targets are identified and validated using dsRNA specific for the identified target, or other non-PTGS mediated methods, for example antisense technology.

The regulated transcription system of the present invention provides an advantage to other double stranded expression systems. Following transfection of the dsRNA library, cells contain hundreds to thousands of dsRNA expression cassettes, with concomitant expression of that many expression cassettes. In the dsRNA expression system of the present invention, dsRNA expression cassettes contained within the expression vector integrate into the chromosome of the transfected cell. As described in detail below, every transfected cell integrates one of the double stranded expression cassettes. Desirably no transcription occurs until the episomal (non-integrated) expression vectors are diluted out of the cell such that not more than 5 episomal vectors remain in the cell. Most desirably no transcription occurs until all of the episomal (non-integrated) expression vectors are diluted out of the cell and only the integrated expression cassette remains (a process usually taking about two to several weeks of cell culture). At this time transcription is induced, allowing dsRNA to be expressed in the cells. This method ensures that only one species of dsRNA is expressed per cell, as opposed to other methods that express hundreds to thousands of double stranded species. The use of the above-described system results in the loss of all but one expression cassette, which in turn, permits the rapid screening of libraries without requiring screening multiple pools of libraries to identify the target gene.

Non-Library Approaches for the Identification of a Nucleic Acid Sequence that Modulates Cell Function, Gene Expression in a Cell, or the Biological Activity of a Target Polypeptide in a Cell Through PTGS Nucleic acid sequences that modulate cell function, gene expression in a cell, or the biological activity of a target polypeptide in a cell may also be identified using non-library based approaches involving PTGS. For example, a single known nucleic acid sequence encoding a polypeptide with unknown function or a single nucleic acid fragment of unknown sequence and/or function can be made into a double stranded RNA molecule. This dsRNA is then transfected into a desired cell type and the cell is assayed for modulations in cell function, gene expression of a target nucleic acid in the cell, or the biological activity of a target polypeptide in the cell, using methods described herein. A modulation in cell function, gene expression in the cell, or the biological activity of a target polypeptide in the cell identifies the nucleic acid of the dsRNA as a nucleic acid the modulates the specific cell function, gene expression, or the biological activity of a target polypeptide. As a single dsRNA species is transfected into the cells, the nucleic acid sequence responsible for the modulation is readily identified. This non-library based approach to nucleic acid identification is desirably used under conditions that inhibit an interferon response or dsRNA stress response. Such conditions are described in detail herein.

The discovery of novel genes through the methods of the present invention may lead to the generation of novel therapeutics. For example, genes that decrease cell invasion may be used as targets for drug development, such as for the development of cytostatic therapeutics for use in the treatment of cancer. Development of such therapeutics is important because currently available cytotoxic anticancer agents are also toxic for normal rapidly dividing cells. In contrast, a cytostatic agent may only need to check metastatic processes, and by inference, slow cell growth, in order to stabilize the disease. In another example, genes that increase neuronal regeneration may be used to develop therapeutics for the treatment, prevention, or control of a number of neurological diseases, including Alzheimer's disease and Parkinson's disease. Genes that are involved in the ability to support viral replication and be used as targets in anti-viral therapies. Such therapies may be used to treat, prevent, or control viral diseases involving human immunodeficiency virus (HIV), hepatitis C virus (HCV), hepatitis B virus (HBV), and human papillomavirus (HPV). The efficacies of therapeutics targeting the genes identified according to the present invention can be further tested in cell culture assays, as well as in animal models.

The Use of Vertebrate or Mammalian Cell Lines for Identification of Nucleic Acid Sequences that Modulate Cell Function, Expression of a Target Nucleic Acid, or Biological Activity of a Target Polypeptide While the use of the present invention is not limited to vertebrate or mammalian cells, such cells can be used to carry out the nucleic acid identification methods described herein. Desirably the vertebrate or mammalian cells used to carry out the present invention are cells that have been cultured for only a small number of passages (e.g., less than 30 passages of a cell line that has been obtained directly from American Type Culture Collection), or are primary cells. In addition, vertebrate or mammalian cells can be used to carry out the present invention when the dsRNA being transfected into the cell is not complexed with cationic lipids.

The following examples are to illustrate the invention. They are not meant to limit the invention in any way. For example, it is noted that any of the following examples can be used with double stranded RNAs of any length. The methods of the present invention can be readily adapted by one skilled in the art to utilize double stranded RNAs of any desired length.

Example 1

Design and Delivery of Vectors for Intracellular Synthesis of dsRNA for Library Based Screening Approaches to Nucleic Acid Identification Using PTGS PTGS is induced when dsRNA is made intracellularly. The library based screening approaches to nucleic acid identification through PTGS may require that dsRNA reside in certain cellular compartments in order to exert its effect. Therefore, expression plasmids that transcribe dsRNA in the cytoplasm and in the nucleus are utilized. There are two classes of nuclear transcription vectors: one that is designed to express polyadenylated dsRNA (for example, a vector containing an RNA polymerase II promoter and a poly A site) and one that expresses non-adenylated dsRNA (for example, a vector containing an RNA polymerase II promoter and no poly A site, or a vector containing a T7 promoter). Different cellular distributions are predicted for the two species of RNA; both vectors are transcribed in the nucleus, but the ultimate destinations of the RNA species are different intracellular locations. Intracellular transcription may also utilize bacteriophage T7 and SP6 RNA polymerase, which may be designed to transcribe in the cytoplasm or in the nucleus. Alternatively, Qbeta replicase RNA-dependent RNA polymerase may be used to amplify dsRNA. Viral RNA polymerases, either DNA and RNA dependent, may also be used. Alternatively, dsRNA replicating polymerases can be used. Cellular polymerases such as RNA Polymerase I, II, or III or mitochondrial RNA polymerase may also be utilized. Both the cytoplasmic and nuclear transcription vectors contain an antibiotic resistance gene to enable selection of cells that have taken up the plasmid. Cloning strategies employ chain reaction cloning (CRC), a one-step method for directional ligation of multiple fragments (Pachuk et al., Gene 243:19-25, 2000). Briefly, the ligations utilize bridge oligonucleotides to align the DNA fragments in a particular order and ligation is catalyzed by a heat-stable DNA ligase, such as Ampligase, available from Epicentre.

Inducible or Repressible Transcription Vectors for the Generation of a dsRNA Expression Library If desired, inducible and repressible transcription systems can be used to control the timing of the synthesis of dsRNA. Inducible and repressible regulatory systems involve the use of promoter elements that contain sequences that bind prokaryotic or eukaryotic transcription factors upstream of the sequence encoding dsRNA. In addition, these factors also carry protein domains that transactivate or transrepress the RNA polymerase II. The regulatory system also has the ability to bind a small molecule (e.g., a coinducer or a corepressor). The binding of the small molecule to the regulatory protein molecule (e.g., a transcription factor) results in either increased or decreased affinity for the sequence element. Both inducible and repressible systems can be developed using any of the inducer/transcription factor combinations by positioning the binding site appropriately with respect to the promoter sequence. Examples of previously described inducible/repressible systems include lac, ara, Steroid-RU486, and ecdysone—Rheogene, Lac (Cronin et al. *Genes & Development* 15: 1506-1517, 2001), ara (Khlebnikov et al., J. Bacteriol. 2000 December; 182(24):7029-34), ecdysone (Rheogene, www.rheogene.com), RU48 (steroid, Wang X J, Liefer K M, Tsai S, O'Malley B W, Roop D R., Proc Natl Acad Sci USA. 1999 Jul. 20; 96(15):8483-8), tet promoter (Rendal et al., Hum Gene Ther. 2002 January; 13(2):335-42. and Lamartina et al., Hum Gene Ther. 2002 January; 13(2):199-210), or a promoter disclosed in WO 00/63364, filed Apr. 19, 2000.

Nuclear Transcription Vectors for the Generation of a Nuclear dsRNA Expression Library Nuclear transcription vectors for use in library based screening approaches to identify nucleic acids that modulate cell function, gene expression, or the biological activity of a target polypeptide are designed such that the target sequence is flanked on one end by an RNA polymerase II promoter (for example, the HCMV-IE promoter) and on the other end by a different RNA polymerase II promoter (for example, the SCMV promoter). Other promoters that can be used include other RNA polymerase II promoters, an RNA polymerase I promoter, an RNA polymerase III promoter, a mitochondrial RNA polymerase promoter, or a T7 or SP6 promoter in the presence of T7 or SP6 RNA polymerase, respectively, containing a nuclear localization signal. Bacteriophage or viral promoters may also be used. The promoters are regulated transcriptionally (for example, using a tet ON/OFF system (Forster et al., supra; Liu et al., supra; and Gatz, supra) such that they are only active in either the presence of a transcription-inducing agent or upon the removal of a repressor. A single chromosomal integrant is selected for, and transcription is induced in the cell to produce the nuclear dsRNA.

Those vectors containing a promoter recognized by RNA Pol I, RNA Pol II, or a viral promoter in conjunction with co-expressed proteins that recognize the viral promoter, may also contain optional sequences located between each promoter and the inserted cDNA. These sequences are transcribed and are designed to prevent the possible translation of a transcribed cDNA. For example, the transcribed RNA is synthesized to contain a stable stem-loop structure at the 5' end to impede ribosome scanning. Alternatively, the exact sequence is irrelevant as long as the length of the sequence is sufficient to be detrimental to translation initiation (e.g., the sequence is 200 nucleotides or longer). The RNA sequences can optionally have sequences that allow polyA addition, intronic sequences, an HIV REV binding sequence, Mason-Pfizer monkey virus constitutive transport element (CTE) (U.S. Pat. No. 5,880,276, filed Apr. 25, 1996), and/or self splicing intronic sequences.

To generate dsRNA, two promoters can be placed on either side of the target sequence, such that the direction of transcription from each promoter is opposing each other. Alternatively, two plasmids can be cotransfected. One of the plasmids is designed to transcribe one strand of the target sequence while the other is designed to transcribe the other strand. Single promoter constructs may be developed such that two units of the target sequence are transcribed in tandem, such that the second unit is in the reverse orientation with respect to the other. Alternate strategies include the use of filler sequences between the tandem target sequences.

Cytoplasmic Transcription Vectors for the Generation of a Cytoplasmic dsRNA Expression Library Cytoplasmic transcription vectors for use in library based screening approaches to identifying nucleic acids that modulate cell function, gene expression, or the biological activity of a target polypeptide in a cell using PTGS are made according to the following method. This approach involves the transcription of a single stranded RNA template (derived from a library) in the nucleus, which is then transported into the cytoplasm where it serves as a template for the transcription of dsRNA molecules. The DNA encoding the ssRNA is integrated at a single site in the target cell line as described for the nuclear RNA expression library, thereby ensuring the synthesis of only one species of dsRNA in a cell, each cell expressing a different dsRNA species.

A desirable approach is to use endogenous polymerases such as the mitochondrial polymerase in animal cells or mitochondrial and chloroplast polymerases in plant cells for cytoplasmic and mitochondrial (e.g., chloroplast) expression to make dsRNA in the cytoplasm. These vectors are formed by designing expression constructs that contain mitochondrial or chloroplast promoters upstream of the target sequence. As described above for nuclear transcription vectors, dsRNA can be generated using two such promoters placed on either side of the target sequence, such that the direction of transcription from each promoter is opposing each other. Alternatively, two plasmids can be cotransfected. One of the plasmids is designed to transcribe one strand of the target sequence while the other is designed to transcribe the other strand. Single promoter constructs may be developed such that two units of the target sequence are transcribed in tandem, such that the second unit is in the reverse orientation with respect to the other. Alternate strategies include the use of filler sequences between the tandem target sequences.

Alternatively, cytoplasmic expression of dsRNA for use in library based screening approaches is achieved by a single subgenomic promoter opposite in orientation with respect to the nuclear promoter. The nuclear promoter generates one RNA strand that is transported into the cytoplasm, and the singular subgenomic promoter at the 3' end of the transcript is sufficient to generate its antisense copy by an RNA dependent RNA polymerase to result in a cytoplasmic dsRNA species.

Target Cell Line Development for use with Cytoplasmic dsRNA Expression Libraries The target cell line, using the vector containing the G418 cassette, GFP, and loxP site is designed as described above.

Development of a Cytoplasmic dsRNA Expression Library

Double stranded RNA expression libraries are generated by inserting cDNA or randomized sequences (as described herein) into an expression vector containing a single nuclear promoter (RNA polymerase I, RNA polymerase II, or RNA polymerase III), which allows transcription of the insert sequence. It is desirable that this nuclear promoter activity is regulated transcriptionally (for example, using a tet ON/OFF system described, for example, by Forster et al, supra; Liu et al., supra; and Gatz, supra), such that the promoters are only active in either the presence of a transcription-inducing agent or upon the removal of a repressor. This ensures that transcription is not induced until episomal copies of the vector(s) are diluted out. Vectors also contain a selectable marker, such as the hygromycin resistance gene, and a loxP site. The expression vectors are integrated into the target cell line by methods previously described in this application using Cre recombinase (other site-specific recombinative strategies can be employed, as described previously).

At two days post-transfection, cells are subjected to hygromycin selection using concentrations established in kill curve assays. Surviving cells are cultured in hygromycin to select for cells bearing integrated vectors and to dilute out episomal copies of the vector(s). At this point transcription is induced, and a single stranded RNA (ssRNA) species derived from the insert sequence is transcribed in the nucleus from the nuclear promoter in the inserted vector. The insert is designed such that the insert sequences in the transcript are flanked by bi-directional promoters of RNA bacteriophages (for example, Qbeta or MS2, RNA dependent RNA polymerase promoters) or cytoplasmic viral RNA-dependent RNA polymerase promoter sequences (for example, those of Sindbis or VEEV subgenomic promoters). The nuclear transcript is translocated to the cytoplasm where it acts as a template for dsRNA by an RNA dependent RNA polymerase, which may be provided through co-transfection of a vector that encodes an RNA-dependent RNA polymerase. Alternatively, an integrated copy of the polymerase may be used.

Example 2

Generation of Templates for In Vitro Transcription of dsRNA for Non-Library Based Approaches for Identification of Nucleic Acids Using PTGS Nucleic acid sequences that modulate cell function, gene expression in a cell, or the biological activity of a target polypeptide in a cell may also be identified using non-library based approaches involving PTGS. A single known nucleic acid sequence encoding a polypeptide with unknown function or a single nucleic acid fragment of unknown sequence and/or function can be made into a double stranded RNA molecule. This dsRNA is then transfected into a desired cell type and assayed for modulations in cell function, gene expression in the cell, or the biological activity of a target polypeptide in the cell, using methods described herein. A modulation in cell function, gene expression in the cell, or the biological activity of a target polypeptide in the cell identifies the nucleic acid of the dsRNA as a nucleic acid the modulates the specific cell function, gene expression, or the biological activity of a target polypeptide. This non-library based approach to nucleic acid identification is desirably used under conditions that inhibit an interferon response or dsRNA stress response. Such conditions are described in detail below.

Nucleic acid fragments generated, for example, by PCR or restriction endonuclease digestion, encoding the respective target sequences were used as templates for in vitro transcription reactions. PCR fragments are superior to plasmid templates for the synthesis of discrete sized RNA molecules. The PCR fragments encoded at least 20-50 or 100 to 1000, for example, 500 to 600 nucleotides (nts) of the target sequence and were derived from the target mRNA. Known target sequences were obtained from GenBank and or other DNA sequence databases. Target sequences were also obtained from cellular RNAs that were generated into cDNAs to create a number of different dsRNA molecules. Accordingly, it is possible that the sequence and/or function of the target sequence was not known at the time the dsRNA was generated.

Templates for sense target RNAs were generated by placing the bacteriophage T7 promoter at the 5' end of the target coding strand while antisense RNA templates contained the T7 promoter at the 5' end of the non-coding strand. This was achieved by encoding the T7 promoter at the 5' ends of the respective PCR primers. Alternatively SP6 promoters, or a combination of SP6 and T7 promoters may be used.

PCR was performed by conventional methods. The use of both PCR templates in equimolar amounts in an in vitro transcription reaction resulted in primarily dsRNA. The use of two separate fragments has been found to be superior- to the use of one PCR fragment containing two T7 promoters, one located at each end of the target sequence, presumably due to transcription interference that occurs during transcription of the dual promoter template. Following PCR amplification, the DNA was subjected to Proteinase K digestion and phenol-chloroform extraction to remove contaminating RNases. Following ethanol precipitation, the DNA was resuspended in RNase-free water at a concentration of 1 to 3 µg/µl.

As an alternative to phenol-chloroform extraction, DNA can be purified in the absence of phenol using standard methods such as those described by Li et al. (WO 00/44914, filed Jan. 28, 2000). Alternatively, DNA that is extracted with phenol and/or chloroform can be purified to reduce or eliminate the amount of phenol and/or chloroform. For example, standard column chromatography can be used to purify the DNA (WO 00/44914, filed Jan. 28, 2000).

Example 3

In Vitro RNA Transcription and RNA Analysis

In vitro transcription reactions are carried out using the Riboprobe Kit (Promega Corp.), according to the manufacturer's directions. The template DNA is as described above. Following synthesis, the RNA is treated with RQ1 DNase (Promega Corp.) to remove template DNA. The RNA is then treated with Proteinase K and extracted with phenol-chloroform to remove contaminating RNases. The RNA is ethanol precipitated, washed with 70% ethanol, and resuspended in RNase-free water. Aliquots of RNA are removed for analysis and the RNA solution is flash frozen by incubating in an ethanol-dry ice bath. The RNA is stored at −80° C.

As an alternative to phenol-chloroform extraction, RNA can be purified in the absence of phenol using standard methods such as those described by Li et al. (WO 00/44914, filed Jan. 28, 2000). Alternatively, RNA that is extracted with phenol and/or chloroform can be purified to reduce or eliminate the amount of phenol and/or chloroform. For example, standard column chromatography can be used to purify the RNA (WO 00/44914, filed Jan. 28, 2000).

dsRNA is made by combining equimolar amounts of PCR fragments encoding antisense RNA and sense RNA, as described above, in the transcription reaction. Single stranded antisense or sense RNA is made by using a single species of PCR fragment in the reaction. The RNA concentration is determined by spectrophotometric analysis, and RNA quality is assessed by denaturing gel electrophoresis and by digestion with RNase T1, which degrades single stranded RNA.

An mRNA library is produced using Qbeta bacteriophage, by ligating the nRNAs to the flank sequences that are required for Qbeta replicase function (Qbeta flank or Qbeta flank plus P1), using RNA ligase. The ligated RNAs are then transformed into bacteria that express Qbeta replicase and the coat protein. Single plaques are then inoculated into fresh bacteria. All plaques are expected to carry transgene sequences. Each plaque is grown in larger quantities in bacteria that produce the Qbeta polymerase, and RNA is isolated from the bacteriophage particles. Alternatively, if the Qbeta flank plus P1 is used to generate the library (e.g., P1=MS2, VEEV, or Sindbis promoter sequences), these vectors can be used to carry out the in vitro transcription along with the cognate polymerase. The in vitro made dsRNA is then used to transfect cells.

RNA Delivery

In vitro made dsRNA is directly added to the cell culture medium at concentrations ranging from 50 µg/ml to 500 µg/ml. Uptake of dsRNA is also facilitated by electroporation using those conditions required for DNA uptake by the desired cell type. RNA uptake is also mediated by lipofection using any of a variety of commercially available and proprietary cationic lipids, DEAE-dextran-mediated transfection, microinjection, protoplast fusion, calcium phosphate precipitation, viral or retroviral delivery, or biolistic transformation. The RNA is naked RNA or a local anesthetic RNA complex. Modulation of cell function, gene expression, or polypeptide biological activity is then assessed in the transfected cells.

Some dsRNA sequences, possibly in certain cell types and through certain delivery methods, may result in an interferon response. During the screening methods of the present invention, induction of an interferon response is not desired, as this would lead to cell death and possibly to the prevention of gene silencing.

One of the components of an interferon response is the induction of the interferon-induced protein kinase PKR. Suppression of the interferon response and/or the PKR response is desired in the target cells. The dsRNA delivery methods described herein are performed such that an interferon response or dsRNA stress response is not included. It is recognized, however, that certain conditions might present with an induction of the interferon response. To prevent such a response, a number of other strategies may be employed with any of the above described screening methods to identify a nucleic acid that modulates cell function, gene expression, or the polypeptide biological activity of a cell, as described herein.

To prevent an interferon response, interferon and PKR responses are silenced in the target cells using a dsRNA species directed against the mRNAs that encode proteins involved in the response. Desirably interferon response promoters are silenced using dsRNA. Alternatively, the expression of proteins that bind the interferon response element is abolished using dsRNA techniques.

In an alternative strategy, interferon and PKR knockout cell lines are created through approaches utilizing expression cassettes that encode an antisense RNA and ribozymes directed to the cellular mRNAs that encode the proteins involved in the response. Knockout cells are created by standard gene knockout technologies using homologous recombination to alter target sequences, using homologous DNA alone, or as complexes of RecA protein and single stranded DNA homologous to the target sequence(s). Interferon response element (IRE) sequences, sequences that encode transcription factors that bind IRE sequences, the promoter and/or gene sequences that encode proteins in the PKR and interferon response pathways are molecules that are targeted for knockout.

If desired, proteins involved in gene silencing such as Dicer or Argonaut can be overexpressed or activated to increase the amount of inhibition of gene expression (Beach et al., WO 01/68836, filed Mar. 16, 2001).

Example 4

Cytoplasmic Transcription Vectors for Non-Library Based Approaches to Nucleic Acid Identification Using PTGS Double stranded RNA molecules for use in non-library based methods for the identification of nucleic acids that modulate cell function, gene expression of a target nucleic acid, or target polypeptide biological activity in a cell can also be generated through the use of cytoplasmic transcription vectors. Such vectors are generated as now described.

The PCR fragments generated for in vitro transcription templates, as described above, are inserted into a cloning vector containing one T7 promoter located just outside the polylinker region. Such a vector is pZERO blunt (Promega Corp.). The PCR fragment is cloned into a restriction site in the polylinker in such a way that the fragment's T7 promoter is distal to the vector's promoter. The resulting vector contains the target sequence flanked by two T7 promoters; transcription from this vector occurs in converging directions. Convergent transcription is desired for these intracellular vectors, due to the uncertainty of getting sense and antisense vectors into the same cell in high enough and roughly equivalent amounts. In addition, the local concentration of antisense and sense RNAs with respect to each other is high enough to enable dsRNA formation when the dual promoter construct is used.

A hygromycin resistance cassette is cloned into the pZERO blunt vector as well. The hygromycin resistance cassette contains the hygromycin resistance gene under the control of the Herpes Simplex Virus (HSV) thymidine kinase promoter and the SV40 polyadenlyation signal. The cassette is in a plasmid vector and is flanked at both ends by a polylinker region enabling ease of removal and subsequent cloning. Hygromycin selection was chosen because of the rapidity of death induced by hygromycin as well as extensive in-house experience with hygromycin selection. Alternatively, other selection methods known to those skilled in the art may be used.

The vectors are transfected into the desired cells using standard transformation or transfection techniques described herein, and the cells are assayed for the ability of the dsRNA molecules encoded by the vectors to modulate cell function, gene expression of a target nucleic acid, or the biological activity of a target polypeptide, as described herein.

Example 5

Analysis of RNA from Transfected Cells

Regardless of whether a library based screening approach or a non-library based approach was used to identify nucleic acid sequences, in order to measure the level of dsRNA effector molecule within the cell, as well as the amount of target mRNA within the cell, a two-step reverse transcription PCR reaction was performed with the ABI PRISM™7700 Sequence Detection System. Total RNA was extracted from cells transfected with dsRNA or a plasmid from a dsRNA expression library using Trizol and DNase. Two to three different cDNA synthesis reactions were performed per sample; one for human GAPDH (a housekeeping gene that should be unaffected by the effector dsRNA), one for the target mRNA, and/or one for the sense strand of the expected dsRNA molecule (effector molecule). Prior to cDNA synthesis of dsRNA sense strands, the RNA sample was treated with T1 RNase. The cDNA reactions were performed in separate tubes using 200 ng of total RNA and primers specific for the relevant RNAs. The cDNA products of these reactions were used as templates for subsequent PCR reactions to amplify GAPDH, the target cDNA, and/or the sense strand copied from the dsRNA. All RNA was quantified relative to the internal control, GAPDH.

Example 6

Target Sequence Identification

To identify the target sequence affected by a dsRNA, using any of the above-described methods, DNA is extracted from expanded cell lines (or from the transfected cells if using a non-integrating dsRNA system) according to methods well known to the skilled artisan. The dsRNA encoding sequence of each integrant (or non-integrated dsRNA molecule if using a non-library based method) is amplified by PCR using primers containing the sequence mapping to the top strand of the T7 promoter (or any other promoter used to express the dsRNA). Amplified DNA is then cloned into a cloning vector, such as pZERO blunt (Promega Corp.), and then sequenced. Sequences are compared to sequences in GenBank and/or other DNA databases to look for sequence identity or homology using standard computer programs. If the target mRNA remains unknown, the mRNA is cloned from the target cell line using primers derived from the cloned dsRNA by established techniques (Sambrook et al., supra). Target validation is then carried out as described herein.

In the stably integrated dsRNA expression system described above, despite efforts to reduce negative position effects, inefficient dsRNA synthesis by PCR methods may occur. This can be circumvented by rescuing the integrated cDNA or randomized nucleic sequences into replicating plasmids. Rescued plasmids are amenable to amplification in bacteria and to sequencing. Rescue is achieved by re-transfecting the population of cells transfected with the dsRNA expression library with the rescue plasmid and a plasmid encoding Cre recombinase. The rescue plasmid carries a bacterial origin of replication, a bacterial antibiotic selection marker, an SV40 origin of replication, and an SV40 T antigen expression cassette, as well as loxP sites positioned as an inverted repeat to allow Cre-mediated double recombination. The SV40-based origin of replication in the rescue plasmid allows amplification of rescued sequences in the integrated cells. Following rescue, higher levels of transcription are anticipated, thereby favoring dsRNA formation. The cells are then screened for modulations in cell function, target nucleic acid expression, or target polypeptide biological activity changes as described herein.

Example 7

Prevention of an Interferon Response During Gene Silencing

As discussed above, during the above-described screening methods, induction of an interferon response is not desired, as this would lead to cell death, anti-proliferative responses, and possibly to prevention of gene silencing. One of the components of an interferon response is the induction of the interferon-induced protein kinase PKR. Suppression of the interferon response and/or the PKR response is desired in the target cells. The dsRNA delivery methods described herein are performed such that an interferon response is not included. It is recognized, however, that certain conditions might present with an induction of the interferon response. To prevent such a response, a number of other strategies may be employed with any of the above described screening methods to identify a nucleic acid that modulates cell function, gene expression, or the polypeptide biological activity of a cell, as described herein.

To prevent an interferon response in a system involving stable integration of the nucleic acid containing the dsRNA expression cassette, the vectors used to generate either the loxP integrant or the vector that encodes the dsRNA expression cassette are designed to contain sequences that encode proteins that block the PKR response, such as the Vaccinia virus protein E3 (Romano et al., Molecular and Cellular Biology 18:7304-7316, 1998; Accession No. M36339), or a cellular protein P58$^{IPK}$, which the influenza virus mobilizes to block PKR (Gale et al., Microbiology and Molecular Biology Reviews 64:239-280, 2000; Accession No. XM_032882). Several other viral proteins have also been identified (e.g., Hepatitis C E2; Accession No. S72725) and may be similarly used. These proteins can be expressed in the desired cell types or in animals through the use of any of a number of commercially available mammalian expression vectors or vertebrate expression vectors. Such vectors can be obtained from a number of different manufacturers including Invitrogen (Carlsbad, Calif.) Promega ((Madison, Wis.), or Clontech (Palo Alto, Calif.). An example of such a vector is the pCI-neo Mammalian Expression Vector from Promega.

Regardless of whether nucleic acid encoding a dsRNA is stably integrated into a chromosome or is not integrated into a chromosome, the following methods may be used to prevent an interference response in any of the screening methods of the present invention. In one example of an interferon avoidance strategy, interferon and PKR responses are silenced in the target cells using a dsRNA species directed against the mRNAs that encode proteins involved in the response. Desirably interferon response promoters are silenced using dsRNA. Alternatively, the expression of proteins that bind the interferon response element is abolished using dsRNA techniques.

In an alternative strategy, interferon and PKR knockout cell lines are created through approaches utilizing expression cassettes that encode an antisense RNA and ribozymes directed to the cellular mRNAs that encode the proteins involved in the response. Knockout cells are created by standard gene knockout technologies using homologous recombination to alter target sequences, using homologous DNA alone, or as complexes of RecA protein and single stranded DNA homologous to the target sequence(s). Interferon response element (IRE) sequences, sequences that encode transcription factors that bind IRE sequences, the promoter and/or gene sequences that encode proteins in the PKR and interferon response pathways are molecules that are targeted for knockout.

In yet another alternative, chimeric oligonucleotides may be used to alter target sequences. Methods for inhibiting expression of polypeptides through chimeric oligonucleotides are well known in the art (Igoucheva and Yoon, Human Gene Therapy 11:2307-2312, 2000).

Example 8

Functional Screening for Cell Invasion

Cell invasion is one cell function that may be evaluated in the search for novel genes that are modulated using the methods described herein. Matrigel, a biological extracellular matrix, has properties similar to that of a reconstituted basement membrane and has been used to measure the invasive potential of tumor cells (Platet and Garcia, supra). Cells transfected with randomized or cDNA libraries that have been cloned into PTGS vectors are monitored for their capacity to invade matrigel invasion chambers. Cells that have taken up sequences unrelated to invasion invade the matrigel as efficiently as vector-transfected control cells. Cells experiencing PTGS of genes that are involved in cell invasion invade much less efficiently. If the dsRNA expression cassette is stably integrated in a chromosome, these cells are retrieved and second and third rounds of selection are carried out in order to isolate specific nucleic acid sequences relevant to cell invasion. The effect of these sequences on invasion is ultimately confirmed by their ability to block the formation of tumors in animal models.

Several human cell lines, for example, MDA-MB-231, used by Platet and Garcia (supra), SKBr3, and MCF-7ADR, a more metastatic variant of MCF-7. MDA-MB-231 breast cancer cells (obtained from the American Type Culture Collection) are also transfected with cDNA libraries or randomized nucleic acid libraries constructed into the vectors described above. Desirably all cells in this assay contain a single copy of a transfected gene, as described above.

Cells cultured in commercially available 24- or 96-well formatted systems are used to carry out the cell invasion assay. As this screening protocol relies-upon repeated rounds of selection, it may be desirable to keep the cell numbers in each well low enough that enrichment is seen in each succeeding round, yet high enough to recover sufficient cells to culture within a reasonable time period. Therefore, culture conditions that result in invasion by greater than 50% of the cells and that still permit recovery from the surface of the matrigel are made optimal. Non-invasive (NIH3T3 cells) or poorly invasive (MCF7) cell lines are analyzed in parallel as negative controls for invasion.

Initially, triplicate cultures of half-log order dilutions from $10^2$ to $10^6$ cells per well are plated. Cells are then recovered by "scrubbing" with a sterile cotton swab in fresh culture media and are seeded into 96-well plates. The number of invasive cells in the matrigel is quantified using either an MTT-based assay (Sasaki and Passaniti, Biotechniques 24:1038-1043, 1998) or a fluorescent indicator (Gohla et al., Clin. Exp. Metastasis 14:451-458, 1996).

Once the appropriate cell densities for the assay have been empirically determined, stable transfected cells are plated in the matrigel cell invasion chambers. Each experiment includes the following controls: a sample of untransfected cells as a reference culture; untransfected cells treated with anti-invasive chemotherapeutic agents, such as taxol or doxorubicin, as a positive control for inhibition of invasion; cells transfected with empty vectors to confirm that the vector alone had no effects on invasion; and cells transfected cells with genes that are known to block invasion in this assay, such as estrogen receptor-α or TIMP-2 (Kohn et al., Cancer Research 55:1856-1862, 1995; and Woodhouse et al., Cancer (Supplement) 80:1529-1536, 1997).

Cells that fail to invade the matrigel are removed from each well to the corresponding wells of a 96-well plate and cultured until macroscopic colonies are visible. It is important to collect cells at more than one time point after plating, since the time it takes for PTGS to be effective may vary, and it may be that different genes are active at different times after plating. Once the cells are transferred to 96-well plates, they are diluted out and taken through successive rounds of re-screening in the invasion assay in order to expand and isolate cell lines with altered invasive ability. As the population becomes more and more enriched for cells with a non-invasive phenotype, the reduction in invasive cells in the matrigel can be better quantified via MTT or fluorescence assays. Ultimately, a large panel of cloned double-stable cell lines is generated.

This assay can also be carried out with cells into which a dsRNA is not stably integrated into a chromosome. The assay is conducted essentially as described above except that multiple rounds of selection and re-screening are not necessary since the cell is transfected with only one dsRNA species. Thus, the target(s) of the PTGS event is readily identifiable using the cloning and sequencing techniques described above.

Example 9

Downregulation of HIV Using HIV-Derived dsRNA and Inhibitors of the Interferon Response Pathway During the course of HIV infection, the viral genome is reverse transcribed into a DNA template that is integrated into the host chromosome of infected dividing cells. The integrated copy is now a blueprint from which more HIV particles are made. Several cell lines that contain integrated copies of a defective HIV genome, HIVgpt (strain HXB2) have been created. The HIVgpt genome contains a deletion of the HIV envelope gene; all other HIV proteins are encoded. The plasmid used to create these cell lines, HIVgpt, was obtained from the AIDS Research and Reference Reagent Program Catalog. Stably integrated cell lines were made with human rhabdomyosarcoma (RD) cells. The lines were made by transfecting cells with the plasmid followed by selection of cells in mycophenolic acid. The HIVgpt genome encodes a mycophenolic acid (MPA) resistance gene in place of the envelope gene and thereby confers resistance to MPA. Cells resistant to MPA were clonally amplified. The media from the cultured clonally expanded cells was assayed for the presence of p24 (an HIV gag polypeptide that is secreted extracellularly). All cell lines were positive for p24, as assessed using a p24 ELISA assay kit (Coulter, Fullerton, Calif.). The cell lines also make non-infectious particles which can be rescued into infectious particles by co-expression of an HIV envelope protein.

The HIVgpt cell lines are used as a model system with which to downregulate HIV expression via PTGS. Plasmids encoding a 600 nt sense RNA, a 600 nt antisense RNA, or a 600 bp double stranded RNA (dsRNA), mapping to the same coordinates of the gag gene of HIV strain HXB2 are used to transfect cells (the map from which the coordinates are based is found at GenBank Accession number K03455, HIV (HXB2), complete genome, and the gag RNAs used in this study map to coordinates 901-1500). Expression of the RNAs is from T7 RNA polymerase promoter(s) located at the 5' end of the gag sense strand, at the 5' end of the antisense strand, or at converging positions at the 5' ends of both the sense and anti-sense strands, respectively. These encoded RNAs are not designed to be able to make protein (i.e., they do not have a cap, a poly A tail, or the native initiation codon). Transcription of the RNAs is catalyzed by T7 RNA polymerase, provided from a second co-transfected T7 RNA polymerase expression plasmid. Control plasmids expressing a similar sized sense RNA, antisense RNA, and dsRNA derived from the gD gene of an HSV2 genome are included as experimental controls (the map from which the coordinates are based is found at GenBank Accession number K01408, HSVgD2 gene, and the HSVgD RNAs used in this study map to coordinates 313-872).

Cells used in these studies are transfected with an expression plasmid encoding a gene product known to interfere with the dsRNA induced interferon response or with the PKR response, as described above. The cells are transfected with lipofectamine (Gibco-BRL) as a transfecting agent according to the manufacturer's instructions.

Two days after transfection, the cells are harvested and seeded into six-well plates and cultured to approximately 80 to 90% confluence. Cells are co-transfected with the T7 RNA polymerase expression plasmid and one of the RNA expression plasmids, such that one well of cells receives the T7 RNA polymerase expression plasmid and the gag sense RNA expression plasmid; one well of cells receives the T7 RNA polymerase expression plasmid and the gag antisense RNA expression plasmid; one well of cells receives the T7 RNA polymerase expression plasmid and the gag dsRNA expression plasmid; one well of cells receives the T7 RNA polymerase expression plasmid and the HSVgd sense RNA expression plasmid; one well of cells receives the T7 RNA polymerase expression plasmid and the HSVgd antisense RNA expression plasmid; and one well of cells receives the T7 RNA polymerase expression plasmid and the HSVgD dsRNA expression plasmid. Transfection is again mediated through lipofectamine (Gibco-BRL). There also is a control group of cells receiving no RNA. The cells are monitored for p24 synthesis over the course of several weeks. The cells are assayed both by measuring p24 in the media of cells (using the p24 ELISA kit from Coulter, according to the manufacturer's instructions) and by immunostaining fixed cells for p24 using a rabbit polyclonal anti-p24 sera and anti-rabbit IgG that is FITC conjugated (Sigma). None of the gD RNAs specifically shut down p24 synthesis. The double stranded gag RNA significantly down regulates p24. The sense and antisense have only a modest effect on p24 synthesis and some of the effect is predicted to be through the ability of the sense and antisense gag RNAs to generate low levels of dsRNA species.

Example 10

Downregulation of PSA Expression in Human Rhabdomyosarcoma Cells Using Intracellular Expression of dsRNA RD cells transiently expressing prostate specific antigen (PSA) were transfected with a T7 RNA polymerase expression vector and T7 RNA expression vectors expressing PSA dsRNA, PSA sense RNA, PSA antisense RNA, or control RNAs. The ability of the expressed RNAs to downregulate PSA expression was assessed, as described further below.

Creation of a Transient PSA Expression Line

Figure 2:
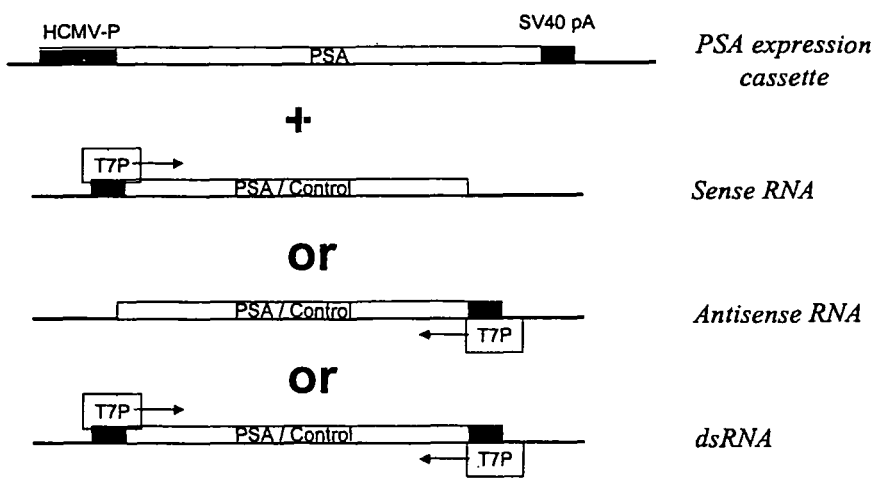
FIG. 2 is a schematic illustration of the production of effector RNAs in cells expressing PSA. The PSA expression cassette used to create the transient PSA expression cell line is depicted at the top of the figure. Expression of PSA is driven by the HCMV IE promoter and the SV40 polyadenylation signal (pA). Only sequences 3' of the PSA initiation codon have been used in these vectors. The effector RNA expression cassettes are shown below the PSA expression cassette and are designed to express PSA sense RNA, PSA antisense RNA, and PSA dsRNA. Expression of the effector RNAs is under the control of the T7 promoter (T7p). Transcription from T7p is catalyzed by T7 RNA polymerase, which is supplied by co-transfecting a T7 RNA polymerase expression plasmid (not shown). Control effector RNA cassettes expressing irrelevant RNAs derived from the Herpes simplex virus glycoprotein D gene were included as controls. The 600 base pair sequence from the Herpes simplex gD gene is from Herpes Simplex virus 2 strain 12 and maps to the coding region downstream of the gD initiation codon.

The ability to downregulate expression of PSA following the expression of a PSA specific double-stranded RNA (dsRNA) was demonstrated in a human rhabdomyosarcoma cell line. Since available PSA cell lines are difficult to work with (i.e., they are hard to transfect, and the cells tend to clump), a human cell line transiently expressing PSA was created. To create these cells, human rhabdomyosarcoma cells were transiently transfected with a PSA plasmid-based expression vector, under conditions that result in transfection of greater than 95% of the cells. Transfection was mediated with lipofectamine transfecting reagent (Gibco-BRL) according to the manufacturer's instructions. Expression of PSA was directed by the HCMV-IE promoter and the SV40 polyadenylation signal (FIG. 2). PSA expression was measured in the supernatant of transfected cells using a PSA ELISA kit (Oncogene Science Diagnostics, Cambridge, Mass.). No PSA was detected in the untransfected parental cells while PSA was abundantly expressed in cells receiving the PSA expression vector.

Downregulation of PSA Expression

The PSA expressing cell line was used as a model system with which to demonstrate the downregulation of PSA protein levels by PTGS. In these studies, plasmids encoding an approximately 600 nt sense RNA, a 600 nt antisense RNA or a 600 nt dsRNA derived from a PSA cDNA were used to transfect the PSA expressing cell line (FIG. 2). Expression of the RNAs was from a T7 RNA polymerase promoter(s) located at the 5' end of the PSA sense strand, at the 5' end of the PSA antisense strand, or at converging positions at the 5' ends of both the sense and antisense strands respectively (FIG. 2). These encoded RNAs are not designed to be able to make protein (they do not have a cap, or a poly A tail). Transcription of the RNAs was catalyzed by T7 RNA polymerase, provided by a co-transfected T7 RNA expression plasmid. Control plasmids expressing similar sized sense RNA, antisense RNA, and dsRNA derived from the glycoprotein D (gD) gene of an Herpes simplex 2 (HSV-2) genome, as described above were included as experimental controls.

Cells used in these studies can optionally be transfected with an expression plasmid encoding a gene product known to interfere with the dsRNA induced interferon response or with the PKR response, as described above. The cells are transfected with lipofectamine (Gibco-BRL) as a transfecting agent according to the manufacturer's instructions.

Human rhabdomyosarcoma cells were seeded into six-well plates and cultured to approximately 80 to 90% confluence. The cells were co-transfected with (A) the PSA expression plasmid; (B) one of the T7 RNA expression plasmids; and (C) the T7 RNA polymerase expression plasmid, such that all PSA expressing cells were transfected with the T7 RNA polymerase expression plasmid and one of the following: the T7 sense PSA RNA expression construct, the T7 antisense PSA RNA expression construct, the T7 dsRNA PSA expression construct, the sense HSVgD RNA expression construct, the antisense HSVgD expression construct, or the dsRNA HSVgd expression construct. Cells received identical amounts of the PSA expression plasmid and the T7 RNA expression plasmid. The amounts of the T7 RNA expression plasmids were also constant amongst the transfected cells. Total DNA per transfection was held constant at 2.5 μg DNA per one well of a six-well plate. In those transfections where there was no T7 RNA expression plasmid, an inert plasmid DNA was used as filler DNA. Transfection was mediated by lipofectamine (Gibco-BRL) according to the manufacturer's instructions. There was also a control group of untransfected cells, as well as an untreated PSA control group of cells transfected with only the PSA expression plasmid in combination with the T7 RNA polymerase expression plasmid.

Figure 3:
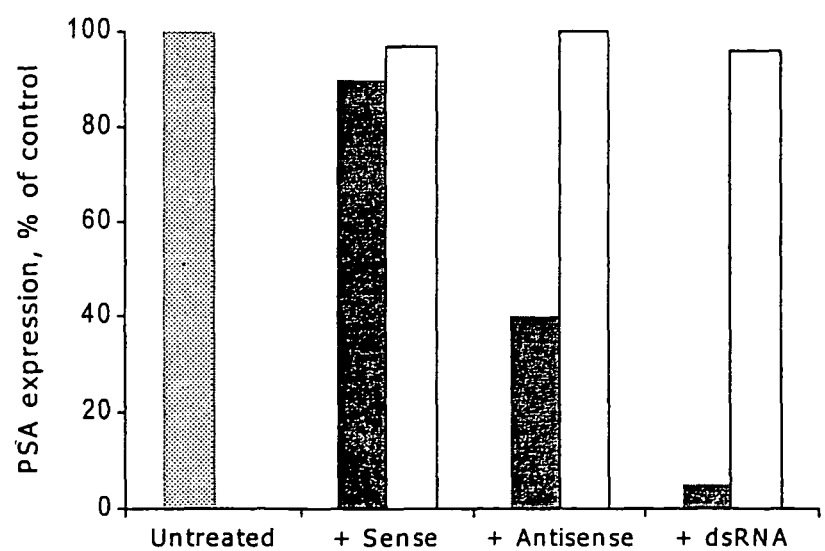
FIG. 3 is a bar graph illustrating silencing of PSA expression by dsRNA. PSA levels in the supernates of transfected cells were determined by ELISA and are plotted as percent expression of the PSA untreated control. The PSA untreated control shown at the left is normalized to 100%. PSA levels in the supernates of cells transfected with the various effector PSA or control RNAs are shown by the shaded and open bars respectively. All data shown is from day two post-transfection. Data from later time points were similar to the day two time point.

PSA-expressing cells that were not transfected with the T7 RNA expression plasmid, as well as cells transfected with the T7 HSV2-gDRNA expression plasmid all expressed PSA abundantly and at comparable levels. Cells transfected with the sense, antisense, and ds PSA RNA expression plasmids all exhibited varying degrees of inhibition of PSA expression. A 5%-10% reduction in expression was seen in cells expressing the PSA sense RNA, a 50% reduction was seen in cells expressing the PSA antisense RNA and greater than 95% reduction was seen in the cells expressing the PSA dsRNA (FIG. 3). The inhibition was seen within two days after transfection and continued up until the last time point taken (one month later) at which point PSA levels were beginning to decline in the untreated cells and the experiment was terminated. The untreated PSA controls as well as cells transfected with the T7 HSV2-gD control RNA expression plasmids all expressed PSA abundantly and at comparable levels (FIG. 3), indicating the specificity of dsRNA effectors to silence gene expression. During the one of month culture, cells were expanded into larger cultures at routine intervals.

Although the PSA specific dsRNA induced significant inhibition of PSA expression, antisense and sense PSA RNAs also induced some level of inhibition. Antisense PSA RNA has the potential to form dsRNA by annealing with PSA mRNA. Therefore the inhibition seen with antisense RNA may be explained by both an antisense mechanism and a dsRNA induced inhibition. A critical intracellular concentration of both antisense RNA and mRNA is required to generate dsRNA. Since much less dsRNA is made in the antisense RNA expressing cells relative to those cells designed to make dsRNA, a lesser inhibition of PSA in the antisense RNA expressing cells is expected if the threshold dsRNA levels required for efficient silencing have not been reached in those cells. We have also demonstrated that a small amount of antisense RNA can be found in cells transfected with our expression vectors (approximately 0.2% the amount of mRNA steady state levels). Antisense expression is presumably driven by cryptic promoters on the non-coding plasmid DNA strand. The observed sense RNA inhibition could therefore also involve a dsRNA molecule. RNA from transfected but untreated cells could also be analyzed to determine if the low level expression of antisense RNAs in these cells results in the production of detectable dsRNA species. Some low level expression of PSA occurred in cells expressing PSA dsRNA. It is likely that some percentage of cells did not take up the dsRNA expression cassette or that the threshold levels of dsRNA were not reached in some cells. No cellular toxicity was seen with any of the dsRNAs generated by the RNA expression vectors suggesting that cytoplasmic expression of dsRNA does not induce the interferon response. In contrast, cell death is induced when certain concentrations of in vitro produced dsRNA is delivered to cells via transfection with certain cationic lipids.

In summary, these results indicate that (i) PSA derived dsRNA is much more efficient than PSA antisense RNA in down-regulating PSA expression, (ii) the down-regulation is sequence specific; only the PSA derived dsRNA and not the control HSV-2 derived dsRNA induced down-regulation of PSA, and (iii) there is no toxicity associated with the cytoplasmic expression of long (600 bp) dsRNA molecules. Additionally, these experiments are the first demonstration of dsRNA mediated down-regulation of gene expression in a human cell line.

Example 11

Intracellular Expression of dsRNA Does not Induce the Type 1 Interferon Response (RNA Stress Response)

Human rhabdomyosarcoma (RD) cells were transfected with various dsRNA expression vectors such that dsRNA was transcribed in the transfected cells as described in Example 10. Transcription of dsRNA occurred in the cells within 24 hours after transfection and continued for the duration of the thirty day experiment. Cells and the supernatants from transfected cells were analyzed during the course of the experiment for any evidence of RNA stress response induction. No evidence of RNA stress response induction by intracellular expressed dsRNA was observed. RD cells have been shown by us to be responsive to type 1 interferon, both alpha and beta, and thus RD cells are capable of mounting an RNA stress response. In addition, positive controls were included in these experiments. A positive control for these experiments is a method of delivering dsRNA which induces the RNA stress response. All positive controls induced the RNA stress response. These experiments are described further below.

Assays Performed to Identify RNA Stress Response Induction

The following assays were performed to measure the induction of an RNA stress response: TUNEL assay to detect apoptotic cells, ELISA assays to detect the induction of alpha, beta and gamma interferon, ribosomal RNA fragmentation analysis to detect activation of 2'5'OAS, measurement of phosphorylated eIF2a as an indicator of PKR (protein kinase RNA inducible) activation, proliferation assays to detect changes in cellular proliferation, and microscopic analysis of cells to identify cellular cytopathic effects. Apoptosis, interferon induction, 2'5' OAS activation, PKR activation, antiproliferative responses, and cytopathic effects are all indicators for the RNA stress response pathway.

Transfection of Cells

Approximately $7 \times 10^5$ RD cells were seeded into individual wells of six-well plates. Cells were transfected when they reached about 90% confluency. Cells were transfected with a T7 RNA polymerase expression construct and a T7 dsRNA expression construct. The T7 dsRNA expression constructs encode converging T7 promoters located on either side of a 600 bp sequence (FIG. 2). Controls included cells transfected with the T7 RNA expression construct alone so that no dsRNA is made in these cells. Total DNA per transfection was held constant at 2.5 µg DNA per one well of a six-well plate. When the T7 RNA polymerase and T7 dsRNA expression vectors were both used, 1.25 µg of each DNA was used per transfection. In those transfections where there was no T7 dsRNA expression construct, inert filler DNA was used to bring the total DNA to 2.5 µg per transfection. Transfection was mediated using Lipofectamine (InVitrogen) according to the manufacturer's directions. The positive control transfections included poly(I)(C)RNA and in vitro transcribed dsRNA of 600 bp that were both complexed with Lipofectamine and transfected into cells. The cells were transfected with in vitro transcribed ssRNA complexed with Lipofectamine. 2.5 µg of each RNA was used per transfection. Other controls included untreated cells. Cells were kept in culture for one month by expanding into larger flasks as the cell numbers increased.

ELISA Assays

Supernatants were removed from the transfected and untreated cells at time points of 1, 2, 7, 17, and 48 hours and every several days for up to one month after the 48 hour time point. Collected supernatants were stored at −80° C. until they were analyzed for the presence of alpha, beta, and gamma interferon using commercially available ELISA kits. The Interferon-alpha ELISA kit was obtained from ENDOGEN (Rockford, Ill.), the Interferon-Beta ELISA kit was obtained from RD 1 (Flanders, N.J.), and the Interferon-gamma ELISA kit was obtained from R&D Systems (Minneapolis, Minn.). ELISAs were all performed according to the manufacturer's directions. Alpha, beta, and gamma interferon were not detected at increased levels in cells expressing intracellular dsRNA compared to the corresponding levels in untreated cells. However, considerable levels of beta interferon were found in cells transfected with poly (I)(C) or with in vitro transcribed dsRNA and ssRNA. Alpha and beta interferon induction are associated with induction of the RNA stress response.

TUNEL Assay

Cells were stained for the presence of apoptotic nuclei using a commercially available kit, TdT FragEL, DNA Fragmentation Detection Kit, In Situ Apoptosis Assay from Oncogene (Boston, Mass.). Cells were stained according the manufacturer's directions. Cells were stained at 2 hours, 7 hours, 17 hours, 2 days, 3 days, 4 days, and 5 days after transfection. There was no evidence of apoptosis induced by intracellular expressed dsRNA at any of the time points analyzed. However, the majority of cells transfected with poly (I)(C) or with the in vitro transcribed dsRNA were apoptotic by 17 hours after transfection. No evidence of apoptosis was observed in the untreated cells or in cells transfected with ssRNA. Apoptosis is an end result of the induction of the RNA stress response pathway.

2'5'OAS Activation

The activation of 2'5' OAS was determined by performing ribosomal RNA fragmentation analysis. Briefly, following transfection, total RNA was extracted from cells using standard procedures. RNA was extracted at the following time points: 2 hours, 7 hours, 17 hours, 48 hours, 3 days, 4 days, and 5 days after transfection. 5-10 µg RNA was analyzed for each sample. RNA samples were first denatured in formaldehyde/formamide RNA sample buffer at 65° C. for 10 minutes prior to being electrophoresed through 0.5×TBE agarose gels. Ribosomal RNA was visualized by staining with ethidium bromide followed by ultraviolet transillumination. Ribosomal RNA fragmentation was observed in cells transfected with poly (I)(C) and with the in vitro transcribed dsRNA. No fragmentation was observed in the untreated control cells, cells transfected with ssRNA, or in cells expressing intracellular dsRNA. These results indicate that 2'5'OAS was not activated by dsRNA when it was made intracellularly. 2'5'OAS activation is associated with induction/activation of the RNA stress response pathway.

PKR Activation

The activation of PKR was determined by measuring the levels of eIF2alpha phosphorylation. Briefly, cells were lysed at various times after transfection (2 hours, 7 hours, 19 hours, 48 hours, 3 days, 4 days, and 5 days after transfection) and analyzed for levels of phosphorylated and non-phosphorylated eIF2 alpha. The protocol for lysing cells can be found in the following reference: Zhang F. et al., J. Biol. Chem. 276 (27):24946-58, 2001. This analysis was performed as described for detecting PKR phosphorylation except that antibodies specific for phosphorylated and non-phosphorylated eIF2alpha were used. These antibodies are available from Cell Signaling Technology (Beverly, Mass.).

Cytopathic effect and Antiproliferative Responses

Cytopathic effect was assayed by analyzing cells microscopically using a light microscope. Cells were analyzed at daily intervals throughout the course of the experiment. Cytopathic effect is defined as any or all of the following: cells detaching from surface of well/flask, cells rounding up, an increased number of vacuoles in transfected cells with respect to the control untreated cells, or differences in morphology of cells with respect to the untreated control cells. No cytopathic effect was seen in those cells expressing dsRNA intracellularly. Severe cytopathic effects were seen in cells transfected with Poly (I)(C) or with dsRNA made in vitro. Cytopathic effect is associated with the RNA stress response.

Antiproliferative responses were assayed by measuring the division rate of cells. The division rate is determined by counting cell numbers using standard procedures. Cells were counted every few days for the duration of the experiment. No antiproliferative responses were seen in cells expressing dsRNA intracellulary. Antiproliferative responses are associated with the RNA stress response.

SUMMARY OF RESULTS

The results of the above assays indicate that intracellular expression of dsRNA does not induce the RNA stress response. The cells that were used for these experiments were competent for RNA stress response induction as was demonstrated by the ability of cationic lipid complexed poly(I)(C) and in vitro transcribed RNA to induce/activate all tested components of this response. In addition, the cells were found to be responsive to exogenously added interferon. These results imply that the cells used for these experiments are not defective in their ability to mount an RNA stress response and therefore can be used as predictors for other cells, both in cell culture and in vivo in animal models. This method described here, which does not induce the interferon stress response, has been found to induce PTGS. This method therefore provides a method to induce PTGS without inducing an undesired RNA stress response.

Although these results were generated using a vector that utilizes a T7 transcription system and therefore expresses dsRNA in the cytoplasm, the vector system can be changed to other systems that express dsRNA intracellularly. Similar results are expected with these expression systems. These systems include, but are not limited to, systems that express dsRNA or hairpin RNAs in the nucleus, in the nucleus followed by transport of the RNAs to the cytoplasm, or in the cytoplasm using non-T7 RNA polymerase based expression systems.

Example 12

Optimization of the Concentrations and Relative Ratios of In Vitro or In Vivo Produced dsRNA and Delivery Agent The optimal concentrations and ratios of dsRNA to a delivery agent such as a cationic lipid, cationic surfactant, or local anesthetic can be readily determined to achieve low toxicity and to efficiently induce gene silencing using in vitro or in vivo produced dsRNA.

Summary of Factors Effecting Nucleic Acid/Cationic Lipid Interactions

Cationic lipid DNA interactions are electrostatic. Electrostatic interactions are highly influenced by the ionic components of the medium. The ability to form stable complexes is also dependent upon the intermolecular interactions between the lipid molecules. At low concentrations, certain inter-lipid interactions are preferred; at higher lipid concentrations, rapid condensates are formed due to higher order interactions. Although local interactions are similar in both of these instances (e.g., phosphoryl groups in the DNA and the charged cationic head group), the long range and inter-lipid interactions are substantially different. Similarly, structurally diverse variants can be obtained simply by changing the charge ratio of the complex by mixing varying amounts of cationic lipid with fixed concentrations of the nucleic acid or vice versa. This variation in the structure of the complexes is evidenced by altered physical properties of the complexes (e.g., differences in octanol partitioning, mobility on density gradients, charge density of the particle, particle size, and transfectability of cells in culture and in vivo) (Pachuk et al. DNA Vaccines—Challenges in Delivery, Current Opinion in Molecular Therapeutics, 2(2) 188-198, 2000 and Pachuk et al., BBA, 1468, 20-30, (2000)). Furthermore, different lipids, local anesthetics, and surfactants differ in their interactions between themselves, and therefore novel complexes can be formed with differing biophysical properties by using different lipids singularly or in combination. For each cell type, the following titration can be carried out to determine the optimal ratio and concentrations that result in complexes that do not induce the stress response or interferon response. At several of these concentrations PTGS is predicted to be induced; however, PTGS is most readily observed under conditions that result in highly diminished cytotoxicity.

Complex Formation dsRNA is either produced by in vitro transcription using the T7 promoter and polymerase or another RNA polymerase, such as an *E. coli* RNA polymerase. dsRNA can also be produced in an organism or cell using endogenous polymerases.

Concentrations of dsRNA, such as PSA-specific dsRNA, are varied from 1 pg to 10 µg. In some instances, 150 ng of a plasmid that encodes a reporter of interest (PSA) to be silenced may be comixed at a concentration between 10 ng and 10 µg. The concentration of cationic lipid, cationic surfactant, local anesthetic, or any other transfection facilitating agent that interacts with the nucleic acid electrostatically are varied at each of the dsRNA concentrations to yield charge ratios of 0.1 to 1000 (positive/negative) (i.e., the ratio of positive charge from lipids or other delivery agents to negative charge from DNA or RNA). The complexes are prepared in water or in buffer (e.g., phosphate, HEPES, citrate, Tris- HCl, Tris-glycine, malate, etc. at pH values that range from 4.0 to 8.5), may contain salt (e.g., 1-250 mM), and may contain glycerol, sucrose, trehalose, xylose, or other sugars (e.g., mono-, di-, or polysaccharide). The mixture is allowed to sit at room temperature, desirably for 30 minutes, and may be stored indefinitely. The complexes are premixed in serum free media. The nucleic acid and the transfecting reagent may be mixed either through direct addition or through a slow mixing process, such as across a dialyzing membrane or through the use of a microporous particle or a device that brings the two solutions together at a slow rate and at low concentrations. In some instances, the two interacting components are mixed at low concentrations, and the final complex is concentrated using a diafilteration or any other concentrating device. Alternatively, if the complexes are formed at high concentrations of either or both of the interacting components, the complexes may be diluted to form an ideal transfection mixture.

Transfection Protocol and Analysis of dsRNA Stress Response

Complexes are added to cells that are ~60-80% confluent in serum free media. The complexes are incubated for various times (e.g., 10 minutes to 24 hours) with the cells at 37° C. and diluted with serum containing media or washed and replated in serum free media. The cells are monitored for toxicity and analyzed at various times for signs of dsRNA response (e.g., TUNNEL assay to detect nicked DNA, phosphorylation of EIF2alpha, induction and activation of 2'5' OAS, or interferon-alpha and beta). Transfection conditions that result in less than 50%, 25%, 10%, or 1% cytotoxicity or that result in a less than 20, 10, 5, 2, or 1.5-fold induction of a stress response are analyzed to determine if PTGS was efficiently induced.

Determining Induction of PTGS

PSA protein levels are determined in cell culture media using standard methods. The data is normalized to the number of live cells in culture to determine the concentrations required to induce PTGS.

Results

Using the above method, cationic lipid complexes of dsRNA induced toxicity at certain ranges. With lipofectamine as the cationic lipid, positive to negative charge ratios greater than 10 did not produce any detectable toxicity at any of the concentrations of dsRNA tested and induced a high level of PTGS, resulting in highly decreased levels of PSA in the culture medium. The RNA concentration ranges tested were 1 pg to 100 ng with a constant amount of lipofectamine (10 uL of a 2 mg/mL solution from GIBCO-BRL Life Technologies, Bethesda, Md.).

Example 13

Method to Avoid dsRNA Mediated Activation of the RNA Stress Response Pathway

Figure 4:
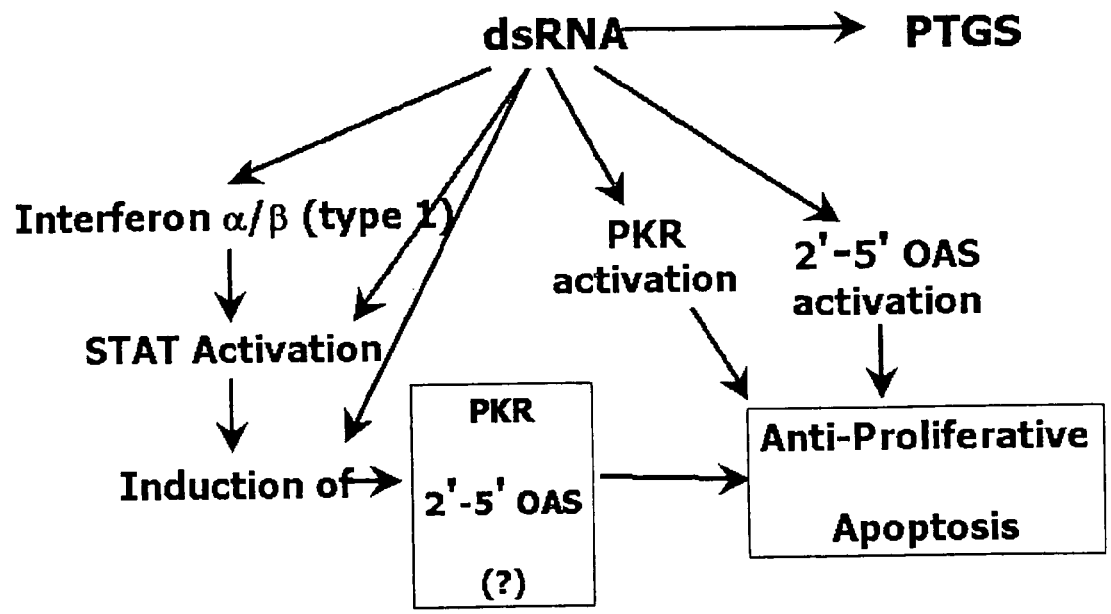
FIG. 4 is a schematic illustration of the RNA stress response pathway, also known as the Type 1 interferon response.

One or more components of the RNA stress response pathway can be mutated or inactivated to avoid induction/activation of the component(s) by dsRNA that is delivered to the cell or animal for the purpose of inducing PTGS. These components, such as those illustrated in FIG. 4, can be knocked out singularly or in combination.

Various standard methods can be used to knockout components of the RNA stress response pathway, such as PKR, human beta interferon Accession No. M25460), and/or 2'5'OAS (Accession No. NM_003733). Alternatively or additionally, one or more interferon response element (IRE) sequences can be mutated or deleted using a knockout construct designed based on the IRE consensus sequence (Ghislain, et al., J Interferon Cytokine Res. 2001 Jun. 21(6):379-88.), and/or one or more transcription factors that bind IRE sequences, such as STAT1 (Accession number XM_010893), can be mutated or deleted. These methods include the use of antisense DNA/RNA, ribozymes, or targeted gene knockout technology mediated by homologous recombination. One skilled in the art is able to design the appropriate antisense sequences, ribozymes, and vectors for targeted knockouts. For example, targeted knockouts may be prepared by any of the following standard methods: Shibata et al., Proc Natl Acad Sci USA. 2001 Jul. 17; 98(15):8425-32. Review., Muyrers et al., Trends Biochem Sci. 2001 May; 26(5):325-31., Paul et al., Mutat Res. 2001 Jun. 5; 486(1):11-9., Shcherbakova et al., Mutat Res. 2000 Feb. 16; 459(1):65-71., Lantsov. Ideal gene therapy: approaches and prospects Mol Biol (Mosk). 1994 May-June; 28(3):485-95., in Gene Transfer and Expression—A Laboratory Manual editor: Michael Kriegler, Publisher—WH Freeman & Co, New York, N.Y., pages 56-60, 1990).

Knockout cells can be readily identified either through the use of an antibiotic resistance marker which when transferred to the chromosome confers 1 resistance to the cell or through the use of dsRNA itself. In particular, dsRNA (e.g., a high concentration of dsRNA) induces apoptosis in wild-type cells while mutant cells survive dsRNA treatment because they cannot mount a stress response. Yet another approach involves performing the dsRNA-induced PTGS experiment in the presence of large concentrations of IRE (dsDNA) oligo, which is expected to titrate activated STAT proteins. These oligos can be delivered intracellularly using transfecting agents or electroporation.

In another method of preventing the interferon response, cells (e.g., RD cells) are transfected with a T7 RNA polymerase expression vector and a T7 dsRNA expression vector encoding dsRNA homologous to the human protein kinase PKR cDNA (accession number M35663) or homologous to the coding sequence of any other component in the RNA stress response pathway. In one particular example, dsRNA corresponding to nucleotides 190-2000 is encoded by the T7dsRNA expression vector. The expression vectors are similar to those described in Example 10 and shown in FIG. 2, except that the dsRNA encoding sequence is derived from the human protein kinase PKR cDNA. Transfection in RD cells is performed as described in Example 10. Within 2-5 days post-transfection, the cells are functionally PKR negative.

Other Embodiments

From the foregoing description, it will be apparent that variations and modifications may be made to the invention described herein to adopt it to various usages and conditions. Such embodiments are also within the scope of the following claims.

All publication, patents, and patent applications mentioned in this specification are herein incorporated by reference to the same extent as if each individual publication, patent, or patent application was specifically and individually indicated to be incorporated by reference.

What is claimed is:

1. A method comprising:
 introducing into a population of RNA stress response-competent cells an expression vector comprising a promoter sequence operably linked to a coding sequence for a nucleic acid less than 50 nucleotides in length for expression of a double stranded hairpin RNA, wherein one strand of the double stranded portion of the hairpin RNA is complementary to a target gene mRNA in the cell, and wherein the hairpin RNA downregulates expression of the target RNA when expressed from the introduced expression vector, wherein the level of apoptosis in the population of cells in which the hairpin RNA is expressed is lower than the level of apoptosis in a population of cells transfected with the same double stranded hairpin RNA produced outside the cell.

2. The method of claim 1, wherein said target gene is a pathogen gene.

3. The method of claim 1, wherein said RNA stress response-competent cell is a vertebrate cell.

4. The method of claim 3, wherein said vertebrate RNA stress response-competent cell is a mammalian cell.

5. The method of claim 1, wherein said double stranded hairpin RNA is expressed as a single transcript that contains an inverted repeat.

6. The method of claim 1, wherein expression of said target gene is decreased at least 50%.

7. The method of claim 6, wherein expression of said target gene is decreased 90%.

8. The method of claim 1, wherein the population of RNA stress response-competent cells is ex vivo.

* * * * *